(12) United States Patent
Wu et al.

(10) Patent No.: US 6,734,173 B1
(45) Date of Patent: May 11, 2004

(54) HSP DNA VACCINES

(75) Inventors: Tzyy-Choou Wu, Stevenson, MD (US); Chien-Fu Hung, Brookeville, MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/501,097

(22) Filed: Feb. 9, 2000

Related U.S. Application Data

(63) Continuation-in-part of application No. 09/421,608, filed on Oct. 20, 1999, now abandoned.
(51) Int. Cl.$^7$ .................. A01N 43/04; A61K 31/70; C07H 21/04
(52) U.S. Cl. ........................... 514/44; 536/23.5
(58) Field of Search ............................ 514/44

(56) References Cited

PUBLICATIONS

LA Babiuk et al., Veterinary Immunology and Immunopathology, "Immunization of animals: from DNA to the dinner plate," 1999, 72, pp. 189–202.*

F Breitburd et al., Cancer Biology, "Human papillomavirus vaccines," 1999, vol. 9, pp. 431–445.*

UA Hasan et al., Journal of Immunological Methods, "Nucleic acid immunization: concepts and techniques associated with third generation vaccines," 1999, 229, pp. 1–22.*

* cited by examiner

*Primary Examiner*—Anne-Marie Falk
(74) *Attorney, Agent, or Firm*—Venable LLP; Shmuel Livnat

(57) ABSTRACT

The invention provides compositions and methods of vaccination that enhance the potency of DNA vaccines. The immunogenic composition contains a DNA encoding a carboxyterminal fragment of a heat shock protein operably linked to a second DNA encoding a MHC class I restricted antigen.

34 Claims, 24 Drawing Sheets

```
1/1                                    31/11
atg cat gga gat aca cct aca ttg cat gaa tat atg tta gat ttg caa cca gag aca act
Met His Gly Asp Thr Pro Thr Leu His Glu Tyr Met Leu Asp Leu Gln Pro Glu Thr Thr
61/21                                  91/31
gat ctc tac tgt tat gag caa tta aat gac agc tca gag gag gag gat gaa ata gat ggt
Asp Leu Tyr Cys Tyr Glu Gln Leu Asn Asp Ser Ser Glu Glu Glu Asp Glu Ile Asp Gly
121/41                                 151/51
cca gct gga caa gca gaa ccg gac aga gcc cat tac aat att gtt acc ttt tgt tgc aag
Pro Ala Gly Gln Ala Glu Pro Asp Arg Ala His Tyr Asn Ile Val Thr Phe Cys Cys Lys
181/61                                 211/71
tgt gac tct acg ctt cgg ttg tgc gta caa agc aca cac gta gac att cgt act ttg gaa
Cys Asp Ser Thr Leu Arg Leu Cys Val Gln Ser Thr His Val Asp Ile Arg Thr Leu Glu
241/81                                 271/91
gac ctg tta atg ggc aca cta gga att gtg tgc ccc atc tgt tct caa gga tcc atg gct
Asp Leu Leu Met Gly Thr Leu Gly Ile Val Cys Pro Ile Cys Ser Gln Gly Ser Met Ala
301/101                                331/111
cgt gcg gtc ggg atc gac ctc ggg acc acc aac tcc gtc gtc tcg gtt ctg gaa ggt ggc
Arg Ala Val Gly Ile Asp Leu Gly Thr Thr Asn Ser Val Val Ser Val Leu Glu Gly Gly
361/121                                391/131
gac ccg gtc gtc gtc gcc aac tcc gag ggc tcc agg acc acc ccg tca att gtc gcg ttc
Asp Pro Val Val Val Ala Asn Ser Glu Gly Ser Arg Thr Thr Pro Ser Ile Val Ala Phe
421/141                                451/151
gcc cgc aac ggt gag gtg ctg gtc ggc cag ccc gcc aag aac cag gca gtg acc aac gtc
Ala Arg Asn Gly Glu Val Leu Val Gly Gln Pro Ala Lys Asn Gln Ala Val Thr Asn Val
481/161                                511/171
gat cgc acc gtg cgc tcg gtc aag cga cac atg ggc agc gac tgg tcc ata gag att gac
Asp Arg Thr Val Arg Ser Val Lys Arg His Met Gly Ser Asp Trp Ser Ile Glu Ile Asp
541/181                                571/191
ggc aag aaa tac acc gcg ccg gag atc agc gcc cgc att ctg atg aag ctg aag cgc gac
Gly Lys Lys Tyr Thr Ala Pro Glu Ile Ser Ala Arg Ile Leu Met Lys Leu Lys Arg Asp
601/201                                631/211
gcc gag gcc tac ctc ggt gag gac att acc gac gcg gtt atc acg acg ccc gcc tac ttc
Ala Glu Ala Tyr Leu Gly Glu Asp Ile Thr Asp Ala Val Ile Thr Thr Pro Ala Tyr Phe
661/221                                691/231
aat gac gcc cag cgt cag gcc acc aag gac gcc ggc cag atc gcc ggc ctc aac gtg ctg
Asn Asp Ala Gln Arg Gln Ala Thr Lys Asp Ala Gly Gln Ile Ala Gly Leu Asn Val Leu
721/241                                751/251
cgg atc gtc aac gag ccg acc gcg gcc gcg ctg gcc tac ggc ctc gac aag ggc gag aag
Arg Ile Val Asn Glu Pro Thr Ala Ala Ala Leu Ala Tyr Gly Leu Asp Lys Gly Glu Lys
781/261                                811/271
gag cag cga atc ctg gtc ttc gac ttg ggt ggt ggc act ttc gac gtt tcc ctg ctg gag
Glu Gln Arg Ile Leu Val Phe Asp Leu Gly Gly Gly Thr Phe Asp Val Ser Leu Leu Glu
841/281                                871/291
atc ggc gag ggt gtg gtt gag gtc cgt gcc act tcg ggt gac aac cac ctc ggc ggc gac
Ile Gly Glu Gly Val Val Glu Val Arg Ala Thr Ser Gly Asp Asn His Leu Gly Gly Asp
901/301                                931/311
gac tgg gac cag cgg gtc gtc gat tgg ctg gtg gac aag ttc aag ggc acc agc ggc atc
Asp Trp Asp Gln Arg Val Val Asp Trp Leu Val Asp Lys Phe Lys Gly Thr Ser Gly Ile
```

FIG. 13-1

```
961/321                             991/331
gat ctg acc aag gac aag atg gcg atg cag cgg ctg cgg gaa gcc gcc gag aag gca aag
Asp Leu Thr Lys Asp Lys Met Ala Met Gln Arg Leu Arg Glu Ala Ala Glu Lys Ala Lys
1021/341                            1051/351
atc gag ctg agt tcg agt cag tcc acc tcg atc aac ctg ccc tac atc acc gtc gac gcc
Ile Glu Leu Ser Ser Ser Gln Ser Thr Ser Ile Asn Leu Pro Tyr Ile Thr Val Asp Ala
1081/361                            1111/371
gac aag aac ccg ttg ttc tta gac gag cag ctg acc cgc gcg gag ttc caa cgg atc act
Asp Lys Asn Pro Leu Phe Leu Asp Glu Gln Leu Thr Arg Ala Glu Phe Gln Arg Ile Thr
1141/381                            1171/391
cag gac ctg ctg gac cgc act cgc aag ccg ttc cag tcg gtg atc gct gac acc ggc att
Gln Asp Leu Leu Asp Arg Thr Arg Lys Pro Phe Gln Ser Val Ile Ala Asp Thr Gly Ile
1201/401                            1231/411
tcg gtg tcg gag atc gat cac gtt gtg ctc gtg ggt ggt tcg acc cgg atg ccc gcg gtg
Ser Val Ser Glu Ile Asp His Val Val Leu Val Gly Gly Ser Thr Arg Met Pro Ala Val
1261/421                            1291/431
acc gat ctg gtc aag gaa ctc acc ggc ggc aag gaa ccc aac aag ggc gtc aac ccc gat
Thr Asp Leu Val Lys Glu Leu Thr Gly Gly Lys Glu Pro Asn Lys Gly Val Asn Pro Asp
1321/441                            1351/451
gag gtt gtc gcg gtg gga gcc gct ctg cag gcc ggc gtc ctc aag ggc gag gtg aaa gac
Glu Val Val Ala Val Gly Ala Ala Leu Gln Ala Gly Val Leu Lys Gly Glu Val Lys Asp
1381/461                            1411/471
gtt ctg ctg ctt gat gtt acc ccg ctg agc ctg ggt atc gag acc aag ggc ggg gtg atg
Val Leu Leu Leu Asp Val Thr Pro Leu Ser Leu Gly Ile Glu Thr Lys Gly Gly Val Met
1441/481                            1471/491
acc agg ctc atc gag cgc aac acc acg atc ccc acc aag cgg tcg gag act ttc acc acc
Thr Arg Leu Ile Glu Arg Asn Thr Thr Ile Pro Thr Lys Arg Ser Glu Thr Phe Thr Thr
1501/501                            1531/511
gcc gac gac aac caa ccg tcg gtg cag atc cag gtc tat cag ggg gag cgt gag atc gcc
Ala Asp Asp Asn Gln Pro Ser Val Gln Ile Gln Val Tyr Gln Gly Glu Arg Glu Ile Ala
1561/521                            1591/531
gcg cac aac aag ttg ctc ggg tcc ttc gag ctg acc ggc atc ccg ccg gcg ccg cgg ggg
Ala His Asn Lys Leu Leu Gly Ser Phe Glu Leu Thr Gly Ile Pro Pro Ala Pro Arg Gly
1621/541                            1651/551
att ccg cag atc gag gtc act ttc gac atc gac gcc aac ggc att gtg cac gtc acc gcc
Ile Pro Gln Ile Glu Val Thr Phe Asp Ile Asp Ala Asn Gly Ile Val His Val Thr Ala
1681/561                            1711/571
aag gac aag ggc acc ggc aag gag aac acg atc cga atc cag gaa ggc tcg ggc ctg tcc
Lys Asp Lys Gly Thr Gly Lys Glu Asn Thr Ile Arg Ile Gln Glu Gly Ser Gly Leu Ser
1741/581                            1771/591
aag gaa gac att gac cgc atg atc aag gac gcc gaa gcg cac gcc gag gag gat cgc aag
Lys Glu Asp Ile Asp Arg Met Ile Lys Asp Ala Glu Ala His Ala Glu Glu Asp Arg Lys
1801/601                            1831/611
cgt cgc gag gag gcc gat gtt cgt aat caa gcc gag aca ttg gtc tac cag acg gag aag
Arg Arg Glu Glu Ala Asp Val Arg Asn Gln Ala Glu Thr Leu Val Tyr Gln Thr Glu Lys
1861/621                            1891/631
ttc gtc aaa gaa cag cgt gag gcc gag ggt ggt tcg aag gta cct gaa gac acg ctg aac
Phe Val Lys Glu Gln Arg Glu Ala Glu Gly Gly Ser Lys Val Pro Glu Asp Thr Leu Asn
```

FIG. 13-2

```
1921/641                              1951/651
aag gtt gat gcc gcg gtg gcg gaa gcg aag gcg gca ctt ggc gga tcg gat att tcg gcc
Lys Val Asp Ala Ala Val Ala Glu Ala Lys Ala Ala Leu Gly Gly Ser Asp Ile Ser Ala
1981/661                              2011/671
atc aag tcg gcg atg gag aag ctg ggc cag gag tcg cag gct ctg ggg caa gcg atc tac
Ile Lys Ser Ala Met Glu Lys Leu Gly Gln Glu Ser Gln Ala Leu Gly Gln Ala Ile Tyr
2041/681                              2071/691
gaa gca gct cag gct gcg tca cag gcc act ggc gct gcc cac ccc ggc ggc gag ccg ggc
Glu Ala Ala Gln Ala Ala Ser Gln Ala Thr Gly Ala Ala His Pro Gly Gly Glu Pro Gly
2101/701                              2131/711
ggt gcc cac ccc ggc tcg gct gat gac gtt gtg gac gcg gag gtg gtc gac gac ggc cgg
Gly Ala His Pro Gly Ser Ala Asp Asp Val Val Asp Ala Glu Val Val Asp Asp Gly Arg
2161/721
gag gcc aag tga (SEQ ID. NO. 19)
Glu Ala Lys OPA (SEQ ID. NO. 20)
```

FIG. 13-3

GM-ETA(dII)-E7

```
1/1 GM-CSF                                            31/11
atg tgg ctg cag aat tta ctt ttc ctg ggc att gtg gtc tac agc ctc tca gca ccc acc
Met Trp Leu Gln Asn Leu Leu Phe Leu Gly Ile Val Val Tyr Ser Leu Ser Ala Pro Thr
61/21                                                 91/31
cgc tca ccc atc act gtc acc cgg cct tgg aag cat gta gag gcc atc aaa gaa gcc ctg
Arg Ser Pro Ile Thr Val Thr Arg Pro Trp Lys His Val Glu Ala Ile Lys Glu Ala Leu
121/41                                                151/51
aac ctc ctg gat gac atg cct gtc aca ttg aat gaa gag gta gaa gtc gtc tct aac gag
Asn Leu Leu Asp Asp Met Pro Val Thr Leu Asn Glu Glu Val Glu Val Val Ser Asn Glu
181/61                                                211/71
ttc tcc ttc aag aag cta aca tgt gtg cag acc cgc ctg aag ata ttc gag cag ggt cta
Phe Ser Phe Lys Lys Leu Thr Cys Val Gln Thr Arg Leu Lys Ile Phe Glu Gln Gly Leu
241/81                                                271/91
cgg ggc aat ttc acc aaa ctc aag ggc gcc ttg aac atg aca gcc agc tac tac cag aca
Arg Gly Asn Phe Thr Lys Leu Lys Gly Ala Leu Asn Met Thr Ala Ser Tyr Tyr Gln Thr
301/101                                               331/111
tac tgc ccc cca act ccg gaa acg gac tgt gaa aca caa gtt acc acc tat gcg gat ttc
Tyr Cys Pro Pro Thr Pro Glu Thr Asp Cys Glu Thr Gln Val Thr Thr Tyr Ala Asp Phe
361/121                                               391/131
ata gac agc ctt aaa acc ttt ctg act gat atc ccc ttt gaa tgc aaa aaa cca gtc caa
Ile Asp Ser Leu Lys Thr Phe Leu Thr Asp Ile Pro Phe Glu Cys Lys Lys Pro Val Gln
421/141                                               451/151
                 ┌─ETA(dII)
aag aat tct │cgc ctg cac ttt ccc gag ggc ggc agc ctg gcc gcg ctg acc gcg cac cag
Lys Asn Ser │Arg Leu His Phe Pro Glu Gly Gly Ser Leu Ala Ala Leu Thr Ala His Gln 481/161                                               511/171
gct tgc cac ctg ccg ctg gag act ttc acc cgt cat cgc cag ccg cgc ggc tgg gaa caa
Ala Cys His Leu Pro Leu Glu Thr Phe Thr Arg His Arg Gln Pro Arg Gly Trp Glu Gln
541/181                                               571/191
ctg gag cag tgc ggc tat ccg gtg cag cgg ctg gtc gcc ctc tac ctg gcg gcg cgg ctg
Leu Glu Gln Cys Gly Tyr Pro Val Gln Arg Leu Val Ala Leu Tyr Leu Ala Ala Arg Leu
601/201                                               631/211
tcg tgg aac cag gtc gac cag gtg atc cgc aac gcc ctg gcc agc ccc ggc agc ggc ggc
Ser Trp Asn Gln Val Asp Gln Val Ile Arg Asn Ala Leu Ala Ser Pro Gly Ser Gly Gly
661/221                                               691/231
gac ctg ggc gaa gcg atc cgc gag cag ccg gag cag gcc cgt ctg gcc ctg acc ctg gcc
Asp Leu Gly Glu Ala Ile Arg Glu Gln Pro Glu Gln Ala Arg Leu Ala Leu Thr Leu Ala
721/241                                               751/251
gcc gcc gag agc gag cgc ttc gtc cgg cag ggc acc ggc aac gac gag gcc ggc gcg gcc
Ala Ala Glu Ser Glu Arg Phe Val Arg Gln Gly Thr Gly Asn Asp Glu Ala Gly Ala Ala
781/261                                               811/271
aac gcc gac gtg gtg agc ctg acc tgc ccg gtc gcc gcc ggt gaa tgc gcg ggc ccg gcg
Asn Ala Asp Val Val Ser Leu Thr Cys Pro Val Ala Ala Gly Glu Cys Ala Gly Pro Ala
841/281                                               871/291
gac agc ggc gac gcc ctg ctg gag cgc aac tat ccc act ggc gcg gag ttc ctc ggc gac
Asp Ser Gly Asp Ala Leu Leu Glu Arg Asn Tyr Pro Thr Gly Ala Glu Phe Leu Gly Asp
```

FIG. 14-1

901/301                                        931/311
                                                          ⎤      ⎡─E7
ggc ggc gac gtc agc ttc agc acc cgc ggc acg cag aac tgg│atc ctc│atg cat gga gat
Gly Gly Asp Val Ser Phe Ser Thr Arg Gly Thr Gln Asn Trp│Ile Leu│Met His Gly Asp 961/321                                        991/331
aca cct aca ttg cat gaa tat atg tta gat ttg caa cca gag aca act gat ctc tac tgt
Thr Pro Thr Leu His Glu Tyr Met Leu Asp Leu Gln Pro Glu Thr Thr Asp Leu Tyr Cys 1021/341                                       1051/351
tat gag caa tta aat gac agc tca gag gag gag gat gaa ata gat ggt cca gct gga caa
Tyr Glu Gln Leu Asn Asp Ser Ser Glu Glu Glu Asp Glu Ile Asp Gly Pro Ala Gly Gln 1081/361                                       1111/371
gca gaa ccg gac aga gcc cat tac aat att gta acc ttt tgt tgc aag tgt gac tct acg
Ala Glu Pro Asp Arg Ala His Tyr Asn Ile Val Thr Phe Cys Cys Lys Cys Asp Ser Thr 1141/381                                       1171/391
ctt cgg ttg tgc gta caa agc aca cac gta gac att cgt act ttg gaa gac ctg tta atg
Leu Arg Leu Cys Val Gln Ser Thr His Val Asp Ile Arg Thr Leu Glu Asp Leu Leu Met 1201/401                                       1231/411
ggc aca cta gga att gtg tgc ccc atc tgt tct cag gat aag ctt ggc tgt ttt ggc gga
Gly Thr Leu Gly Ile Val Cys Pro Ile Cys Ser Gln Asp Lys Leu Gly Cys Phe Gly Gly tga (SEQ ID. NO. 21)
OPA (SEQ ID. NO. 22)

FIG. 14-2

ETA SEQUENCE WITHOUT SIGNAL PEPTIDE

```
1/1                                     31/11
gcc gag gaa gcc ttc gac ctc tgg aac gaa tgc gcc aaa gcc tgc gtg ctc gac ctc aag
Ala Glu Glu Ala Phe Asp Leu Trp Asn Glu Cys Ala Lys Ala Cys Val Leu Asp Leu Lys
61/21                                   91/31
gac ggc gtg cgt tcc agc cgc atg agc gtc gac ccg gcc atc gcc gac acc aac ggc cag
Asp Gly Val Arg Ser Ser Arg Met Ser Val Asp Pro Ala Ile Ala Asp Thr Asn Gly Gln
121/41                                  151/51
ggc gtg ctg cac tac tcc atg gtc ctg gag ggc ggc aac gac gcg ctc aag ctg gcc atc
Gly Val Leu His Tyr Ser Met Val Leu Glu Gly Gly Asn Asp Ala Leu Lys Leu Ala Ile
181/61                                  211/71
gac aac gcc ctc agc atc acc agc gac ggc ctg acc atc cgc ctc gaa ggc ggc gtc gag
Asp Asn Ala Leu Ser Ile Thr Ser Asp Gly Leu Thr Ile Arg Leu Glu Gly Gly Val Glu
241/81                                  271/91
ccg aac aag ccg gtg cgc tac agc tac acg cgc cag gcg cgc ggc agt tgg tcg ctg aac
Pro Asn Lys Pro Val Arg Tyr Ser Tyr Thr Arg Gln Ala Arg Gly Ser Trp Ser Leu Asn
301/101                                 331/111
tgg ctg gta ccg atc ggc cac gag aag ccc tcg aac atc aag gtg ttc atc cac gaa ctg
Trp Leu Val Pro Ile Gly His Glu Lys Pro Ser Asn Ile Lys Val Phe Ile His Glu Leu
361/121                                 391/131
aac gcc ggc aac cag ctc agc cac atg tcg ccg atc tac acc atc gag atg ggc gac gag
Asn Ala Gly Asn Gln Leu Ser His Met Ser Pro Ile Tyr Thr Ile Glu Met Gly Asp Glu
421/141                                 451/151
ttg ctg gcg aag ctg gcg cgc gat gcc acc ttc ttc gtc agg gcg cac gag agc aac gag
Leu Leu Ala Lys Leu Ala Arg Asp Ala Thr Phe Phe Val Arg Ala His Glu Ser Asn Glu
481/161                                 511/171
atg cag ccg acg ctc gcc atc agc cat gcc ggg gtc agc gtg gtc atg gcc cag acc cag
Met Gln Pro Thr Leu Ala Ile Ser His Ala Gly Val Ser Val Val Met Ala Gln Thr Gln
541/181                                 571/191
ccg cgc cgg gaa aag cgc tgg agc gaa tgg gcc agc ggc aag gtg ttg tgc ctg ctc gac
Pro Arg Arg Glu Lys Arg Trp Ser Glu Trp Ala Ser Gly Lys Val Leu Cys Leu Leu Asp
601/201                                 631/211
ccg ctg gac ggg gtc tac aac tac ctc gcc cag caa cgc tgc aac ctc gac gat acc tgg
Pro Leu Asp Gly Val Tyr Asn Tyr Leu Ala Gln Gln Arg Cys Asn Leu Asp Asp Thr Trp
661/221                                 691/231
gaa ggc aag atc tac cgg gtg ctc gcc ggc aac ccg gcg aag cat gac ctg gac atc aaa
Glu Gly Lys Ile Tyr Arg Val Leu Ala Gly Asn Pro Ala Lys His Asp Leu Asp Ile Lys
721/241                  ┌247
ccc acg gtc atc agt cat│cgc ctg cac ttt ccc gag ggc ggc agc ctg gcc gcg ctg acc
Pro Thr Val Ile Ser His│Arg Leu His Phe Pro Glu Gly Gly Ser Leu Ala Ala Leu Thr
                        └
781/261                                 811/271
gcg cac cag gct tgc cac ctg ccg ctg gag act ttc acc cgt cat cgc cag ccg cgc ggc
Ala His Gln Ala Cys His Leu Pro Leu Glu Thr Phe Thr Arg His Arg Gln Pro Arg Gly
841/281                                 871/291
tgg gaa caa ctg gag cag tgc ggc tat ccg gtg cag cgg ctg gtc gcc ctc tac ctg gcg
Trp Glu Gln Leu Glu Gln Cys Gly Tyr Pro Val Gln Arg Leu Val Ala Leu Tyr Leu Ala
```

FIG. 15-1

901/301
gcg cgg ctg tcg tgg aac cag gtc gac cag
Ala Arg Leu Ser Trp Asn Gln Val Asp Gln
931/311
gtg atc cgc aac gcc ctg gcc agc ccc ggc
Val Ile Arg Asn Ala Leu Ala Ser Pro Gly
961/321
agc ggc ggc gac ctg ggc gaa gcg atc cgc
Ser Gly Gly Asp Leu Gly Glu Ala Ile Arg
991/331
gag cag ccg gag cag gcc cgt ctg gcc ctg
Glu Gln Pro Glu Gln Ala Arg Leu Ala Leu
1021/341
acc ctg gcc gcc gcc gag agc gag cgc ttc
Thr Leu Ala Ala Ala Glu Ser Glu Arg Phe
1051/351
gtc cgg cag ggc acc ggc aac gac gag gcc
Val Arg Gln Gly Thr Gly Asn Asp Glu Ala
1081/361
ggc gcg gcc aac gcc gac gtg gtg agc ctg
Gly Ala Ala Asn Ala Asp Val Val Ser Leu
1111/371
acc tgc ccg gtc gcc gcc ggt gaa tgc gcg
Thr Cys Pro Val Ala Ala Gly Glu Cys Ala
1141/381
ggc ccg gcg gac agc ggc gac gcc ctg ctg
Gly Pro Ala Asp Ser Gly Asp Ala Leu Leu
1171/391
gag cgc aac tat ccc act ggc gcg gag ttc
Glu Arg Asn Tyr Pro Thr Gly Ala Glu Phe
1201/401
ctc ggc gac ggc ggc gac gtc agc ttc agc acc cgc ggc acg cag aac tgg acg gtg gag
Leu Gly Asp Gly Gly Asp Val Ser Phe Ser Thr Arg Gly Thr Gln Asn Trp Thr Val Glu
417
1261/421
cgg ctg ctc cag gcg cac cgc caa ctg gag
Arg Leu Leu Gln Ala His Arg Gln Leu Glu
1291/431
gag cgc ggc tat gtg ttc gtc ggc tac cac
Glu Arg Gly Tyr Val Phe Val Gly Tyr His
1321/441
ggc acc ttc ctc gaa gcg gcg caa agc atc
Gly Thr Phe Leu Glu Ala Ala Gln Ser Ile
1351/451
gtc ttc ggc ggg gtg cgc gcg cgc agc cag
Val Phe Gly Gly Val Arg Ala Arg Ser Gln
1381/461
gac ctc gac gcg atc tgg cgc ggt ttc tat
Asp Leu Asp Ala Ile Trp Arg Gly Phe Tyr
1411/471
atc gcc ggc gat ccg gcg ctg gcc tac ggc
Ile Ala Gly Asp Pro Ala Leu Ala Tyr Gly
1441/481
tac gcc cag gac cag gaa ccc gac gca cgc
Tyr Ala Gln Asp Gln Glu Pro Asp Ala Arg
1471/491
ggc cgg atc cgc aac ggt gcc ctg ctg cgg
Gly Arg Ile Arg Asn Gly Ala Leu Leu Arg
1501/501
gtc tat gtg ccg cgc tcg agc ctg ccg ggc
Val Tyr Val Pro Arg Ser Ser Leu Pro Gly
1531/511
ttc tac cgc acc agc ctg acc ctg gcc gcg
Phe Tyr Arg Thr Ser Leu Thr Leu Ala Ala
1561/521
ccg gag gcg gcg ggc gag gtc gaa cgg ctg
Pro Glu Ala Ala Gly Glu Val Glu Arg Leu
1591/531
atc ggc cat ccg ctg ccg ctg cgc ctg gac
Ile Gly His Pro Leu Pro Leu Arg Leu Asp
1621/541
gcc atc acc ggc ccc gag gag gaa ggc ggg
Ala Ile Thr Gly Pro Glu Glu Glu Gly Gly
1651/551
cgc ctg gag acc att ctc ggc tgg ccg ctg
Arg Leu Glu Thr Ile Leu Gly Trp Pro Leu
1681/561
gcc gag cgc acc gtg gtg att ccc tcg gcg
Ala Glu Arg Thr Val Val Ile Pro Ser Ala
1711/571
atc ccc acc gac ccg cgc aac gtc ggc ggc
Ile Pro Thr Asp Pro Arg Asn Val Gly Gly
1741/581
gac ctc gac ccg tcc agc atc ccc gac aag
Asp Leu Asp Pro Ser Ser Ile Pro Asp Lys
1771/591
gaa cag gcg atc agc gcc ctg ccg gac tac
Glu Gln Ala Ile Ser Ala Leu Pro Asp Tyr
1801/601
gcc agc cag ccc ggc aaa ccg ccg cgc gag gac ctg aag taa (SEQ ID. NO. 23)
Ala Ser Gln Pro Gly Lys Pro Pro Arg Glu Asp Leu Lys OCH (SEQ ID. NO. 24)

FIG. 15-2

```
  1 MARAVGIDLG TINSVVSVLE GGDPVVVANS EGSRTTPSIV AFARNGEVLV GQPAKNQAVT NVDRTVRSVK RHMGSDWSIE   80
 81 IDGKKYTAPE ISARILMKLK RDAEAYLGED ITDAVTTPA KDAGQIAGLN VLRIVNEPTA AALAYGLDKG              160
161 EKEQRILVFD LGGGTFDVSL LEIGEGVVEV RATSGDNHLG GDDWDQRVVD WLVDKFKGTS GIDLTKDKMA MQRLREAAEK  240
241 AKIELSSSQS TSINLPYITV DADKNPLFLD EQLTRAEFQR ITQDLLDRTR KPFQSVIADT GISVSEIDRV VLVGGSTRMP  320
321 AVTDLVKELT GGKEPNKGVN PDEVVAVGAA LQAGVLKGEV KDVLLLDVTP LSLGIETKGG VMTRLIERNT TIPTKRSETF  400
401 TTADDNQPSV QIQVYQGERE IAAHNKLLGS FELTGIPPAP RGIPQIEVTF DIDANGIVHV TAKDKGTGKE NTIRIQEGSG  480
481 LSKEDIDRMI KDAEAHAEED RKRREEADVR NQAETLVYQT EKFVKEQREA EGGSKVPEDT INKVDAAVAE AKAALGGSDI  560
561 SAIKSAMEKL GQESQALGQA IYEAAQAASQ ATGAAHPGGE PGGAHPGSAD DVVDAEVVDD GREAK                  626
                                                                          (SEQ ID NO:9)
```

FIG. 16

HSP DNA VACCINES

This application is a continuation-in-part of U.S. patent application Ser. No. 09/421,608 issued Oct. 20, 1999, now abandoned, the entire contents of which is incorporated by reference.

STATEMENT AS TO FEDERALLY SPONSORED RESEARCH

This invention was made with U.S. Government support under National Institutes of Health grants, RO1 CA72631-01 and RFA CA-95-020. The government has certain rights in the invention.

BACKGROUND OF THE INVENTION

The invention relates to DNA vaccines.

Antigen-specific immunotherapy has recently emerged as an approach for controlling cancer because it is capable of developing specific immunity against neoplastic cells while not attacking normal cells. DNA vaccination differs from traditional vaccination in that DNA encoding an antigen (not the antigen itself) is injected into the subject. The production of the antigen, i.e., expression of the antigen encoded by DNA in the vaccine, takes place in the body of the vaccinated individual. However, conventional DNA vaccines have limitations. For example, a major drawback of most DNA vaccines is their potency.

SUMMARY OF THE INVENTION

The invention is based on the discovery that the immunogenicity of a target antigen encoded by a DNA vaccine is enhanced by the presence in the DNA vaccine construct of DNA encoding a carboxyterminal portion of *Mycobacterium tuberculosis* heat shock protein 70 (HSP70). Accordingly, the invention provides compositions and methods of vaccination that significantly enhance the potency, and thus clinical efficacy, of DNA vaccines.

An immunogenic composition contains a first DNA encoding a carboxyterminal fragment of a heat shock protein, e.g., HSP70, operably linked to a second DNA encoding a MHC class I restricted antigen. A carboxyterminal fragment of a protein is a polypeptide which is at least 10 amino acids in length and is derived from a half of a naturally-occurring protein that contains a COOH end. For example, a carboxyterminal fragment of HSP70 is a peptide the amino acid sequence of which is derived from a portion of HSP70 spanning residues 312–625 of SEQ ID NO:9 and is encoded by DNA spanning the coding region of those residues. Preferably, the carboxyterminal fragment contains the amino acid sequence of residues 517–625 of SEQ ID NO:9. For example, the immunogenic composition contains a first DNA encoding a polypeptide containing the amino acid sequence of residues 517 to 625 of SEQ ID NO:9 operably linked to a second DNA encoding a MHC class I restricted antigen. The invention therefore includes an E7-HSP70-CD fusion polypeptide as well as DNA encoding the fusion polypeptide. Optionally, the composition includes DNA encoding a polypeptide containing residues derived from the aminoterminal fragment of HSP70, e.g., residues 161–370 of SEQ ID NO:9. The order in which the DNA components, e.g, first and second (and optionally, third), DNAs are operably linked can be altered without affecting immunogenicity. For example, the HSP-encoding DNA sequences are located 5' or 3' to the target antigen-encoding sequences. Preferably, the DNA is operably linked so that the DNA construct encodes a recombinant polypeptide in which the MHC class I restricted antigen is located amino-terminal to the HSP-derived residues.

As is discussed below, the MHC class I restricted antigen is derived from a pathogen such as a virus or from a cancer tissue. The DNA vaccine of the invention contains a plasmid vector, which contains a first DNA encoding a carboxyterminal fragment of a heat shock protein operably linked to a second DNA encoding a MHC class I restricted antigen. Therapeutic methods include methods of inducing a cytotoxic T cell response to an antigen in a mammal by administering to the mammal the immunogenic compositions described herein.

Alternatively, an immunogenic composition of the invention contains the following components: (a) a first DNA containing a sequence encoding a polypeptide which binds to a professional antigen presenting cell, (b) a second DNA containing a sequence encoding a cytoplasmic translocator polypeptide, and (c) a third DNA containing a sequence encoding a major histocompatibility complex (MHC) class I restricted antigen. The first, second, and third DNAs are operably linked. By "operably linked" is meant that DNA encoding a polypeptide is joined in frame to another DNA encoding a another polypeptide. Translation of operably linked DNAs yields a chimeric polypeptide or fusion gene product. The order in which the first, second, and third DNAs are operably linked is irrelevant. The construct may also contain regulatory sequences. A polypeptide coding sequence and a regulatory sequence(s) are connected in such a way as to permit gene expression when the appropriate molecules (e.g., transcriptional activator proteins) are bound to the regulatory sequence(s).

The first DNA of the immunogenic composition encodes a fragment of a heat shock protein (HSP), e.g., *Mycobacterium tuberculosis* heat shock protein 70 (HSP70). A "fragment" of a given protein is a polypeptide which is shorter in length than the reference polypeptide. For example, the polypeptide is at least 9 or 10 amino acids in length but less than the total number of residues of the mature reference protein or polypeptide. For example, a fragment of HSP70 is less than 70 kDa in molecular mass. A fragment of HSP70 has an amino acid sequence that is at least 50% identical to the amino acid sequence of a naturally-occurring HSP70. The length of an HSP70 fragment is less than 625 amino acids. Preferably, the fragment has a biological activity of the reference protein. For example, the fragment binds to a professional antigen presenting cell (APC) such as a dendritic cell (DC), or the fragment mediates translocation into the cytoplasm of the chimeric polypeptide encoded by the DNA of the immunogenic composition. In some embodiments, the first DNA or the second DNA (or both) encode a fragment of a heat shock protein.

The third DNA of the immunogenic composition encodes an antigenic epitope such as a MHC class I-restricted antigen. Preferably, the antigen is derived from a virus such as a human papovavirus, e.g., a cervical cancer-associated human papillomavirus (HPV). The viral antigen is all or a part of E6 or E7 antigen derived from HPV-16. Other viral antigens include the E2 antigen of bovine viral diarrhea virus; ppUL83 or pp89 of cytomegalovirus; prM/E of encephalitis virus SLE; HBV surface antigen or HBV core antigen of hepatitis B virus; HIV-1 antigens such as gp160; ICP27, gD2, glycoprotein B, or glycoprotein B of herpes simplex virus. Alternatively, the antigen is a cancer antigen such as a mutant p53; MAGE-1 or MAGE-3 associated with melanoma cells, e.g. a cancer-associated antigen expressed on the surface of a tumor cell. Other antigens include malaria peptide (NANP)40, HIV-1 p24, or influenza nucleoprotein.

In one example, the first DNA encodes granulocyte-macrophage colony stimulating factor (GM-CSF) or a fragment thereof. Preferably, a functional GM-CSF fragment contains a disulfide bridge, e.g., a disulfide bridge which spans Cys 51 and Cys93 of SEQ ID NO:1. Other biologically active fragments of GM-CSF are polypeptides which include residues 18–22, 34–41, 38–48, 52–61, 94–115, 95–111 of SEQ ID NO:1. Alternatively, the first DNA (encoding an APC-binding polypeptide) encodes Flt3 ligand (FL), CTLA-4, 4-1BB, CD40 ligand, or TNF receptor (or an APC-binding fragment thereof).

The second DNA may encode a translocation domain of a Pseudomonas exotoxin A (ETA), e.g,. domain II (dII) of ETA (spanning residues 253–364 of SEQ ID NO:3). A translocation domain is a polypeptide that induces translocation of protein or polypeptide to which it is linked into the cytosol of a cell. For example, the second DNA encodes a polypeptide derived from a Diphtheria, clostridial (Botulinum, Tetanus), Anthrax, Yersinia, Cholera, or *Bordetella pertussis* toxin. The presence of DNA encoding a translocation domain in the immunogenic composition enhances MHC class I presentation of the antigen encoded by the composition through translocation of antigen from the endosomal/lysosomal compartment to the cytosol. Preferably, the toxic domain of the gene encoding the toxin is mutated or deleted.

The immunogenic composition need not contain a first, second, and third DNA, as described above. In one alternative embodiment, the third DNA (encoding a target antigen to which immunity is desired) is operably linked to a DNA encoding an APC binding polypeptide (in the absence of DNA encoding a translocator polypeptide); in antoh or a second DNA encoding a translocator polypeptide. For example, the DNA encodes a fusion polypeptide containing E7-ETA, E7-HSP70, E7-GM-CSF, or E7-FL. The immunogenic composition contains DNA encoding residues 1–189 of SEQ ID NO:25 operably linked to DNA encoding an antigen to which immunity is sought.

The immunogenic composition includes DNA encoding an E7-HSP70 fusion polypeptide, DNA encoding a GM-ETA(dII)-E7 fusion polypeptide, or DNA encoding ETA(dII)-E7 (i.e., without the GM component).

Also within the invention is a DNA vaccine. The DNA vaccine composition contains a plasmid vector which includes (a) a first DNA encoding a polypeptide which binds to a professional antigen presenting cell, (b) a second DNA encoding a cytoplasmic translocator polypeptide, and (c) a third DNA encoding a MHC class I restricted antigen. The DNAs are cloned into the plasmid vector in such a way that the first, second, and third DNAs are operably linked. When transcribed and translated in the cell in which the plasmid vector has been taken up, the vector directs production of a chimeric polypeptide which includes an APC-binding portion, a cytoplasmic translocator portion, and an epitope of a class I-restricted antigen.

The DNAs or polynucleotides of the invention are isolated. By "isolated" is meant a nucleic acid molecule that is free of the genes which, in the naturally-occurring genome of the organism, flank the gene sequence of interest. The term therefore includes, for example, a recombinant DNA which is incorporated into a vector; into an autonomously replicating plasmid or virus; or into the genomic DNA of a procaryote or eucaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence. The term excludes large segments of genomic DNA, e.g., such as those present in cosmid clones, which contain a given DNA sequence flanked by one or more other genes which naturally flank it in a naturally-occurring genome.

Nucleic acid molecules (or polynucleotides) include both RNA and DNA, including cDNA, genomic DNA, and synthetic (e.g., chemically synthesized) DNA. Where single-stranded, the nucleic acid molecule may be a sense strand or an antisense strand. The term therefore includes, for example, a recombinant DNA which is incorporated into a vector, into an autonomously replicating plasmid or virus, or into the genomic DNA of a procaryote or eucaryote at a site other than its natural site; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence.

The DNAs of the immunogenic composition or DNA vaccine contain a strand which has the nucleotide sequence of a given reference sequence or which hybridizes at high stringency to a strand of DNA having the reference sequence, or the complement thereof. For example, the DNA has at least 50% sequence identity to a reference sequence, and encodes a polypeptide having a specified biological activity. For example, the biological activity of the polypeptide encoded by the first DNA of the immunogenic composition is binding to an APC, the biological activity of the peptide encoded by the second DNA is cytoplasmic translocation, and the biological activity of the peptide encoded by the third DNA is binding to a MHC class I molecule. Preferably, the DNA has at least 75% identity, more preferably 85% identity, more preferably 90% identity, more preferably 95% identity, more preferably 99% identity, and most preferably 100% identity to the reference sequence.

Nucleotide and amino acid comparisons are carried out using the Lasergene software package (DNASTAR, Inc., Madison, Wis.). The MegAlign module used was the Clustal V method (Higgins et al., 1989, CABIOS 5(2):151–153). The parameter used were gap penalty 10, gap length penalty 10.

Alternatively, the DNAs of the immunogenic composition hybridize at high stringency to a strand of DNA having the reference sequence, or the complement thereof and encode a polypeptide with a specific biological activity. Hybridization is carried out using standard techniques, such as those described in Ausubel et al. (*Current Protocols in Molecular Biology*, John Wiley & Sons, 1989). "High stringency" refers to nucleic acid hybridization and wash conditions characterized by high temperature and low salt concentration, i.e., wash conditions of 65° C. at a salt concentration of approximately 0.1×SSC. "Low" to "moderate" stringency refers to DNA hybridization and wash conditions characterized by low temperature and high salt concentration, i.e., wash conditions of less than 60° C. at a salt concentration of at least 1.0×SSC. For example, high stringency conditions may include hybridization at about 42° C., and about 50% formamide; a first wash at about 65° C., about 2×SSC, and 1% SDS; followed by a second wash at about 65° C. and about 0.1%×SSC. Lower stringency conditions suitable for detecting DNA sequences having about 50% sequence identity to a reference gene or sequence are detected by hybridization at about 42° C. in the absence of formamide;. a first wash at about 42° C., about 6×SSC, and about 1% SDS; and a second wash at about 500C, about 6xSSC, and about 1% SDS.

The invention includes a method of inducing a cytotoxic T cell response to an antigen in a mammal by administering to the mammal the immunogenic composition described above. In preferred embodiments, the composition is administered as naked DNA. The DNA is also administered in the presence of agents which enhance uptake of the DNA by target cells, such as phospholipid formulation, e.g, a liposome. The method is useful to vaccinate a mammal against infection by a pathogen; in this case, the third DNA encodes an antigen derived from said pathogen such as a virus or bacteria. The method is also useful to prevent the development of cancer or treat an existing cancer in a mammal. Mammals at risk of developing a certain type of cancer are identified using known methods, e.g. genetic screening. Individuals at risk of developing a cancer or suffering from cancer are treated by administering the composition in which the third DNA encodes a cancer-associated antigen such as HPV E7 which is associated with cervical cancer.

Other features and advantages of the invention will be apparent from the following description of the preferred embodiments thereof, and from the claims.

Figure 1A:
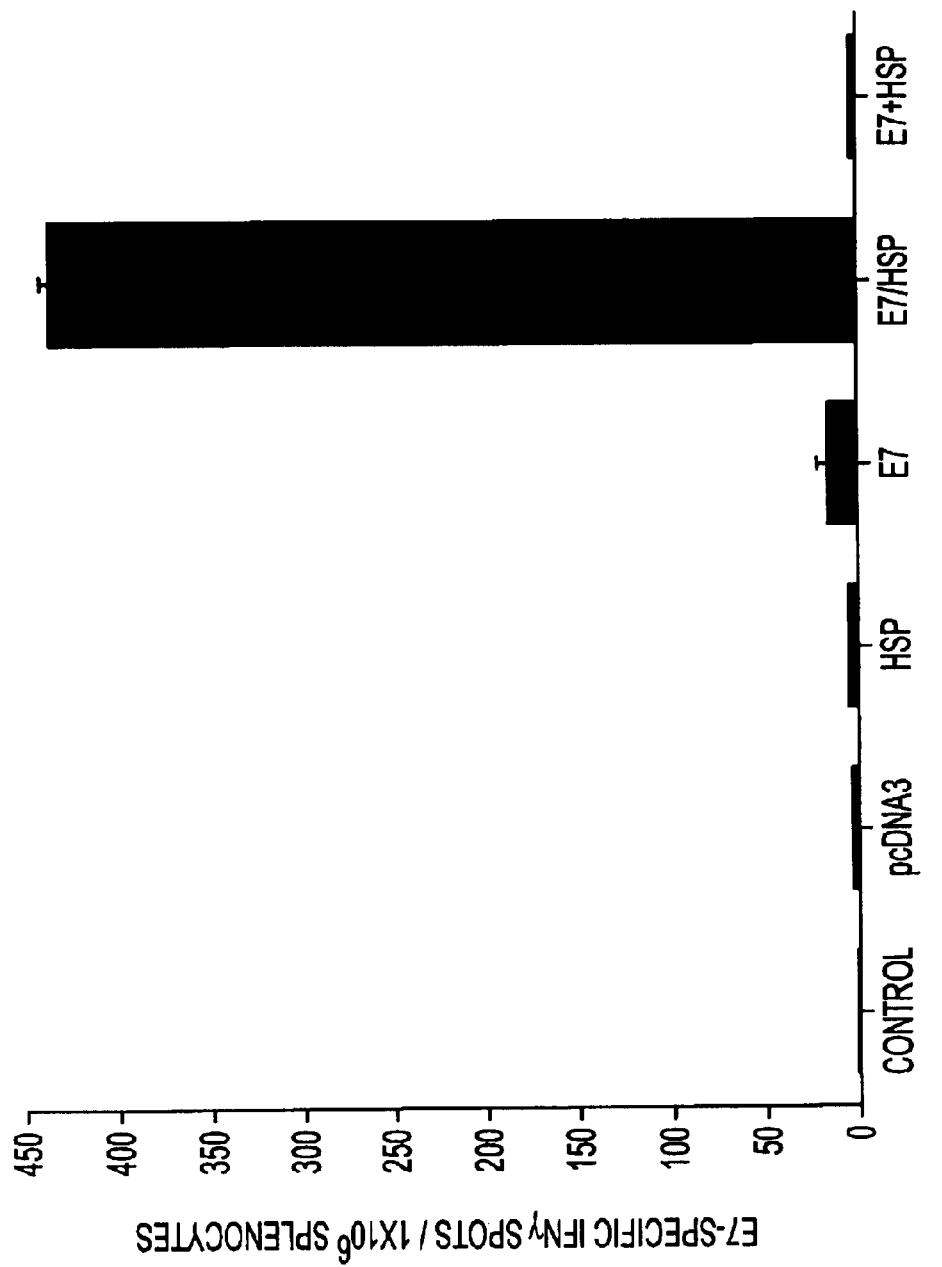
FIG. 1A is a bar graph showing the results of an ELISPOT assay. The number of IFN-γ producing E7-specific CD8+ T cell precursors was determined using the ELISPOT assay. The spot numbers were the mean of triplicates ±SE in each vaccinated group. Mice vaccinated with E7-HSP70 DNA generated the highest IFN-γ$^+$ spot numbers. The data shown represent E7-specific spot-forming cells (subtracting the spot numbers detected in the absence of the E7 CTL peptide).
Figure 1B:
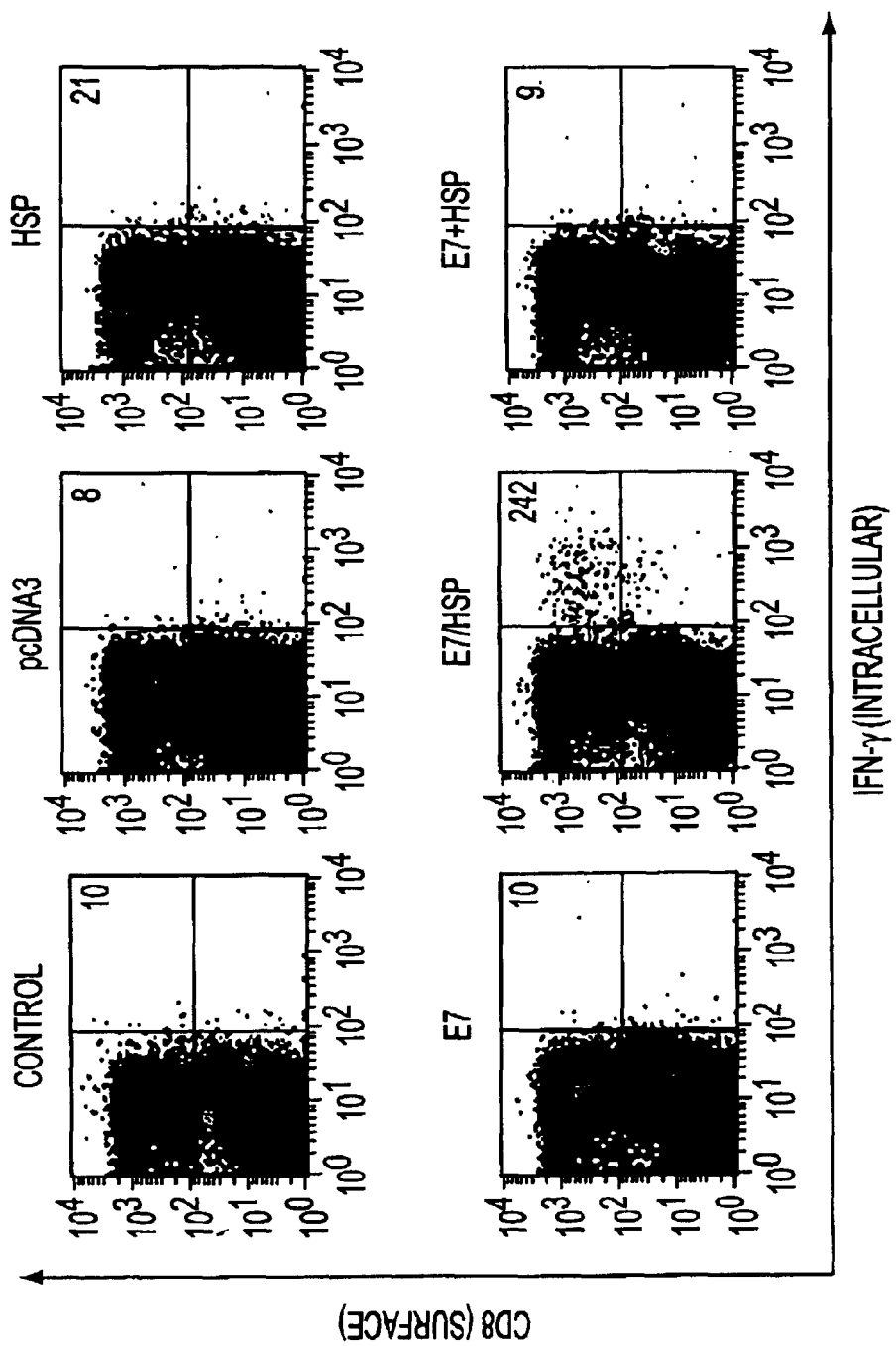
FIG. 1B is a diagram showing the results of a flow cytometry analysis. Splenocytes from vaccinated mice were cultured in vitro with an E7 peptide (residues 49–57; RAHYNIVTF; SEQ ID NO:5) overnight and were stained for both CD8 and intracellular IFN-γ. The number of IFN-γ secreting CD8+ T cell precursors in mice immunized with various recombinant DNA vaccines was analyzed by standard flow cytometry. Mice vaccinated with E7-HSP70 DNA generated the highest IFN-γ$^+$ CD8$^+$ double positive T cells. The numbers of CD8$^+$ IFN-γ$^+$ double positive T cell in 3×10$^5$ splenocytes are indicated in the upper right corner.

The data shown in FIGS. 1A–B indicate the frequency of E7-specific CD8$^+$ T cell precursors in C57BL/6 mice immunized with E7-HSP70 DNA vaccines. C57BL/6 mice were immunized with empty plasmid (pcDNA3), HSP70 DNA (HSP), E7 DNA (E7), E7-HSP70 DNA (E7/HSP) or E7 DNA mixed with HSP70 DNA (E7+ HSP) via gene gun, or received no vaccination. For vaccinated mice, 2 μg DNA /mouse was given twice. Splenocytes were harvested 10 days after the last DNA vaccination.

Figure 2:
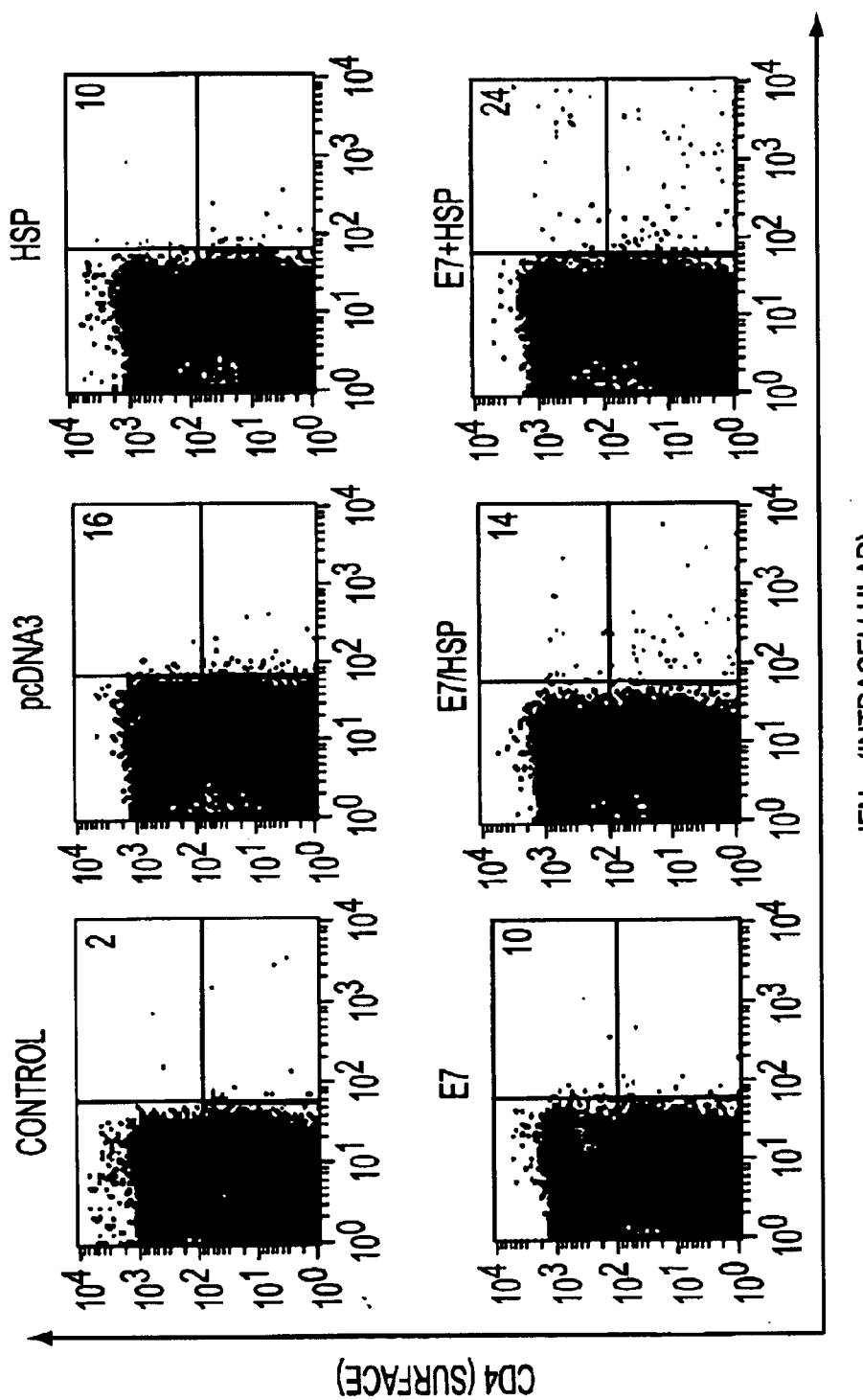

FIG. 2 is a diagram of a flow cytometry analysis of IFN-γ secreting E7-specific CD4$^+$ cells in mice vaccinated with various recombinant DNA vaccines. C57BL/6 mice were immunized as described in FIGS. 1A–B. Splenocytes from vaccinated mice were cultured in vitro with E7 peptide (residues 30–67; DSSEEEDEIDGPAGQAEP-DRAHYNIVTFCCKCDSTLRL; SEQ ID NO:6) overnight and were stained for both CD4 and intracellular IFN-γ. The number of IFN-γ secreting CD4$^+$ T cells was analyzed by flow cytometry. Mice vaccinated with E7-HSP70 DNA generated comparable CD4$^+$ IFN-γ$^+$ double positive cells compared to mice vaccinated with wild-type E7 DNA. The numbers of CD4$^+$ IFN-γ$^+$ double positive T cell in 3×10$^5$ splenocytes are indicated in the upper right corner.

Figure 3:
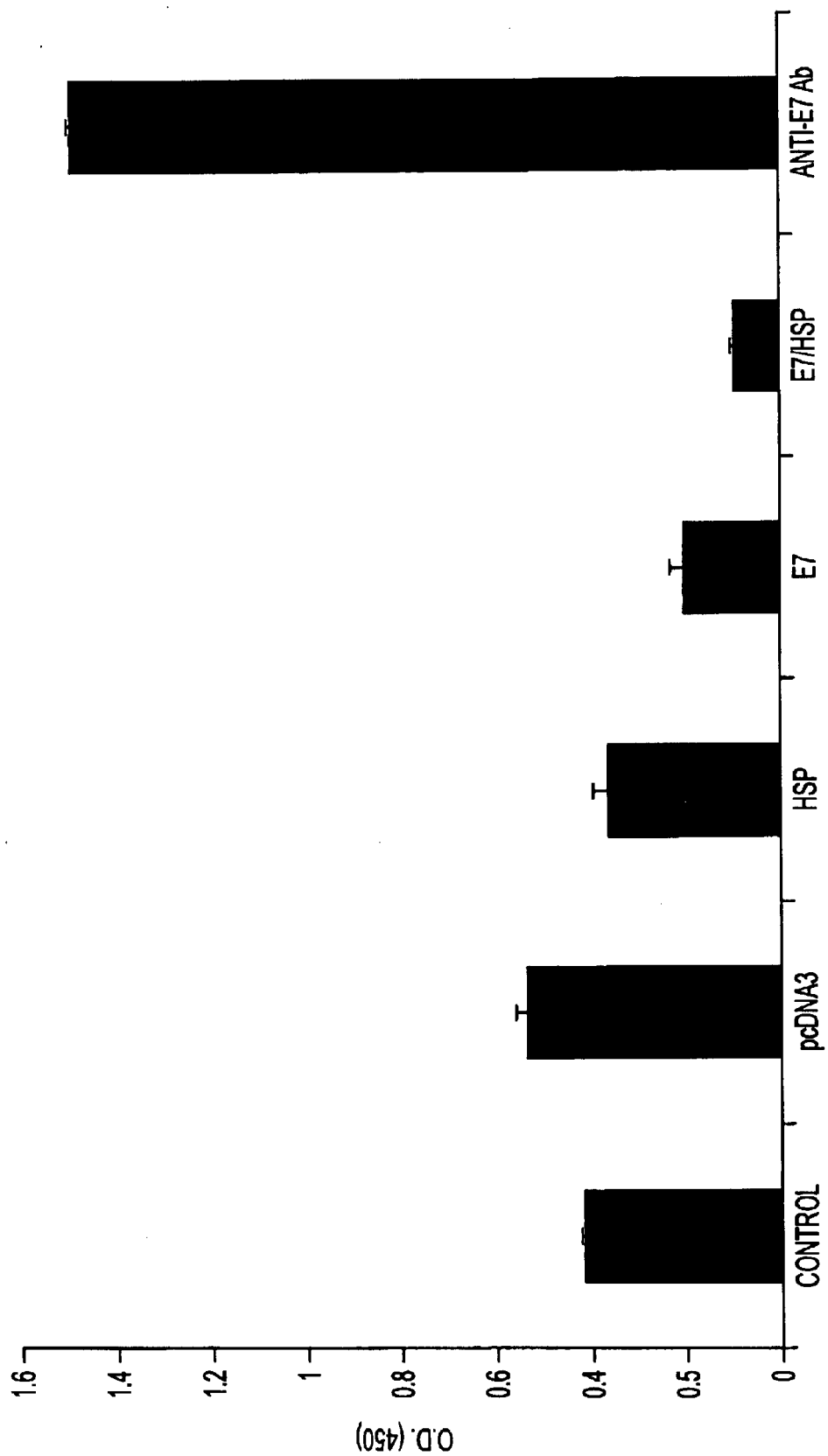

FIG. 3 is a bar graph showing E7-specific antibody responses in C57BL/6 mice immunized with various recombinant DNA vaccines. C57BL/6 mice were immunized with control plasmid (no insert), wild-type HSP70, wild-type E7, or E7-HSP70 DNA via gene gun. Serum samples were obtained from immunized mice 14 days after vaccination. The presence of the E7-specific antibody was detected by ELISA using serial dilution of sera. The results from the 1:80 dilution are shown, showing mean absorbance (O.D.) at 450 nm±SE.

Figure 4A:
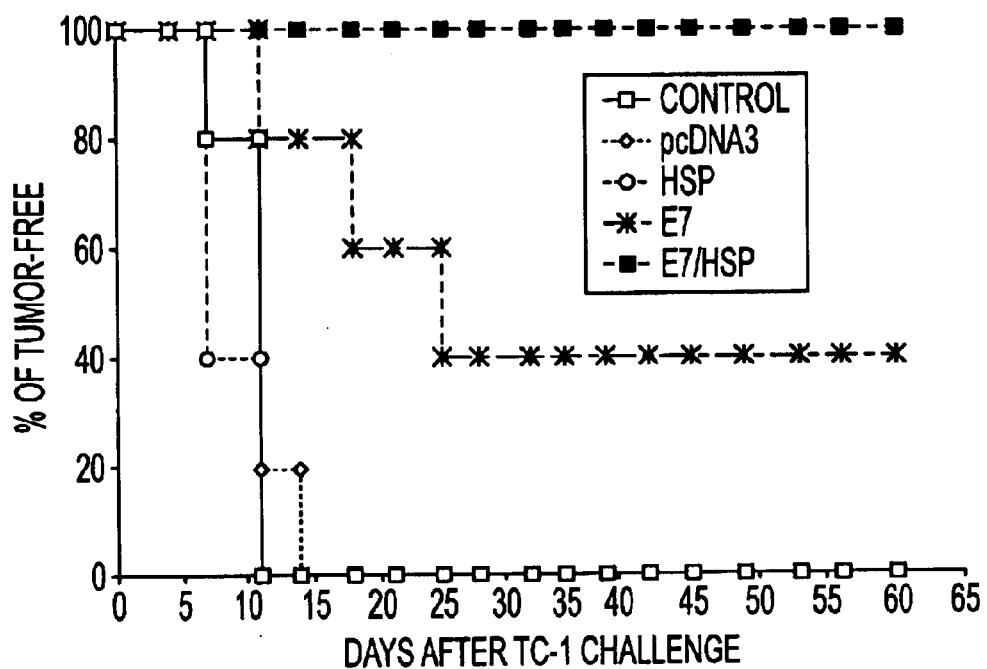
Figure 4B:
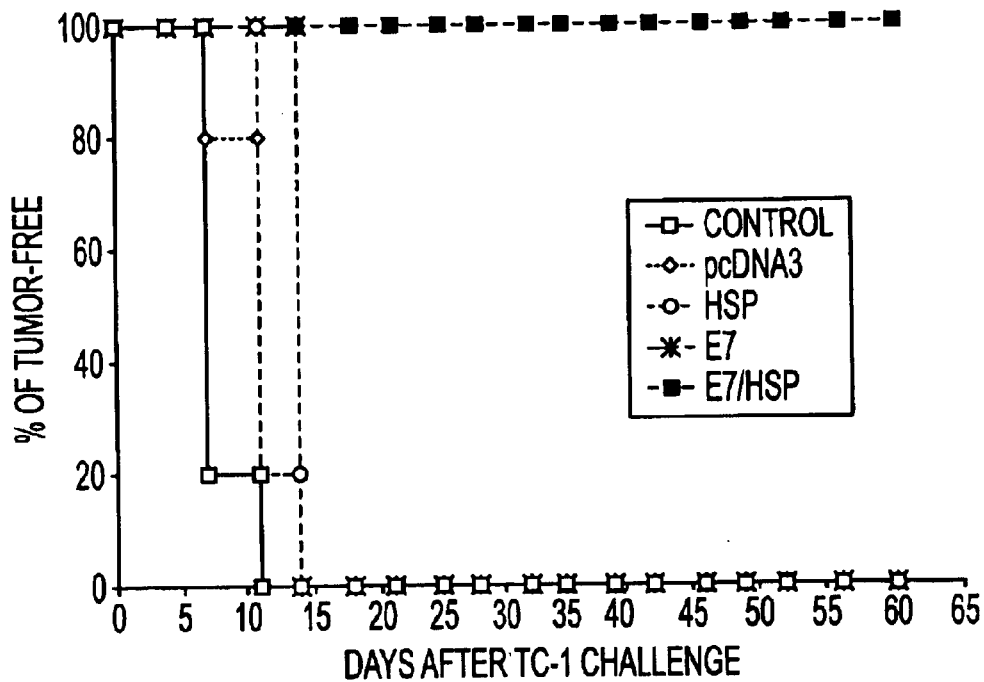

FIGS. 4A–B are line graphs showing that vaccination with E7-HSP70 DNA protects mice against the growth of TC-1 tumors. C57BL/6 mice were immunized with empty plasmid (pcDNA3), HSP70 DNA (HSP), E7 DNA (E7), or E7-HSP70 DNA (E7/HSP) via gene gun. One week after the last vaccination, mice were challenged with 5×10$^4$ TC-1 cells per mouse subcutaneously in the right leg. The mice were monitored for evidence of tumor growth by palpation and inspection twice a week. At day 60 after TC-1 challenge, tumor-free mice were rechallenged with 5×10$^4$ TC-1 cells per mouse subcutaneously in the left leg.

To generate the data shown in FIG. 4A, each mouse received 2 μg DNA vaccine. One week later, the mice were re-vaccinated with the same type and amount of DNA as the first vaccination. To generated the data shown in FIG. 4B, each mouse received only one injection of 2 μg DNA vaccine without further booster.

Figure 5A:
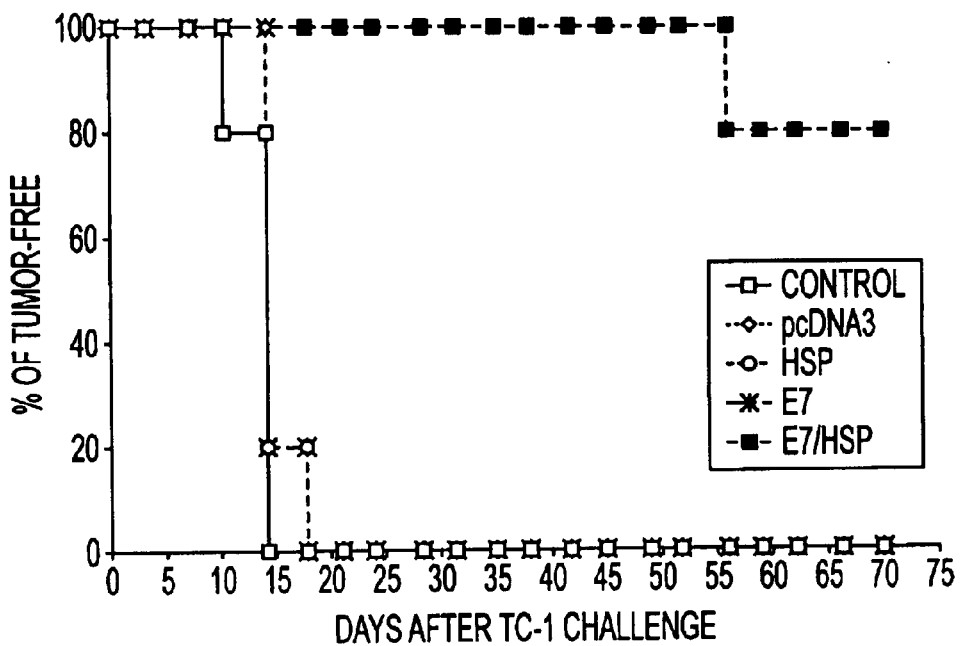
Figure 5B:
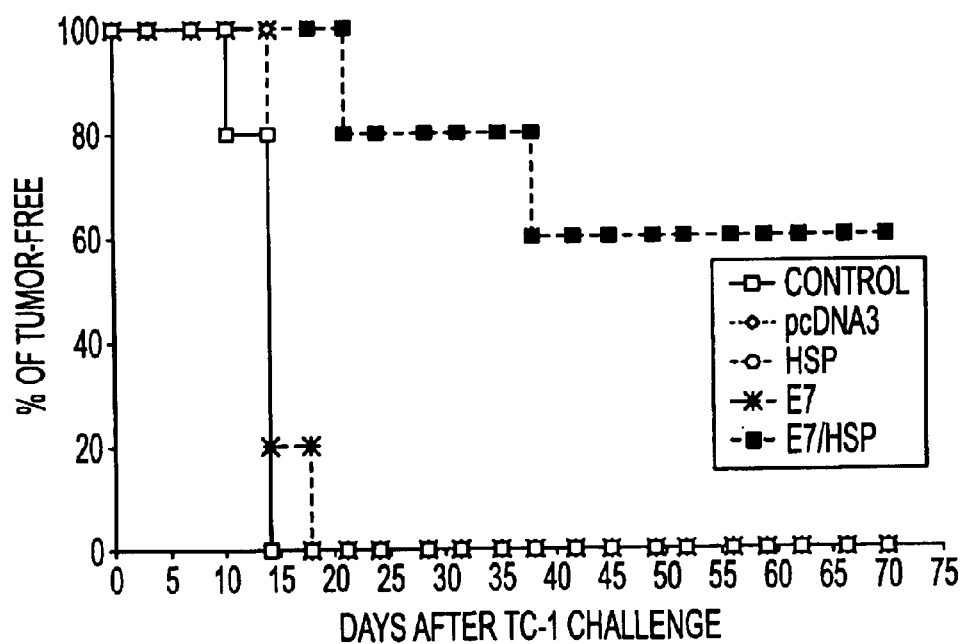

FIGS. 5A–B are line graphs showing that vaccination with E7-HSP70 DNA eradicates pre-existing TC-1 tumor cells. Each mouse was initially challenged with 2×10$^4$ TC-1 cells subcutaneously, followed by DNA vaccination with empty plasmid (pcDNA3), HSP70 DNA (HSP), E7 DNA (E7), or E7-HSP70 DNA (E7/HSP) via gene gun. The mice were monitored for evidence of tumor growth by palpation and inspection twice a week.

To generate the data shown in FIG. 5A, each mouse received 2 μg of DNA vaccine 3 days and 10 days after tumor challenge, and for FIG. 5B, each mouse received 2 μg of DNA vaccine only 3 days after tumor challenge. No further booster was given.

Figure 6:
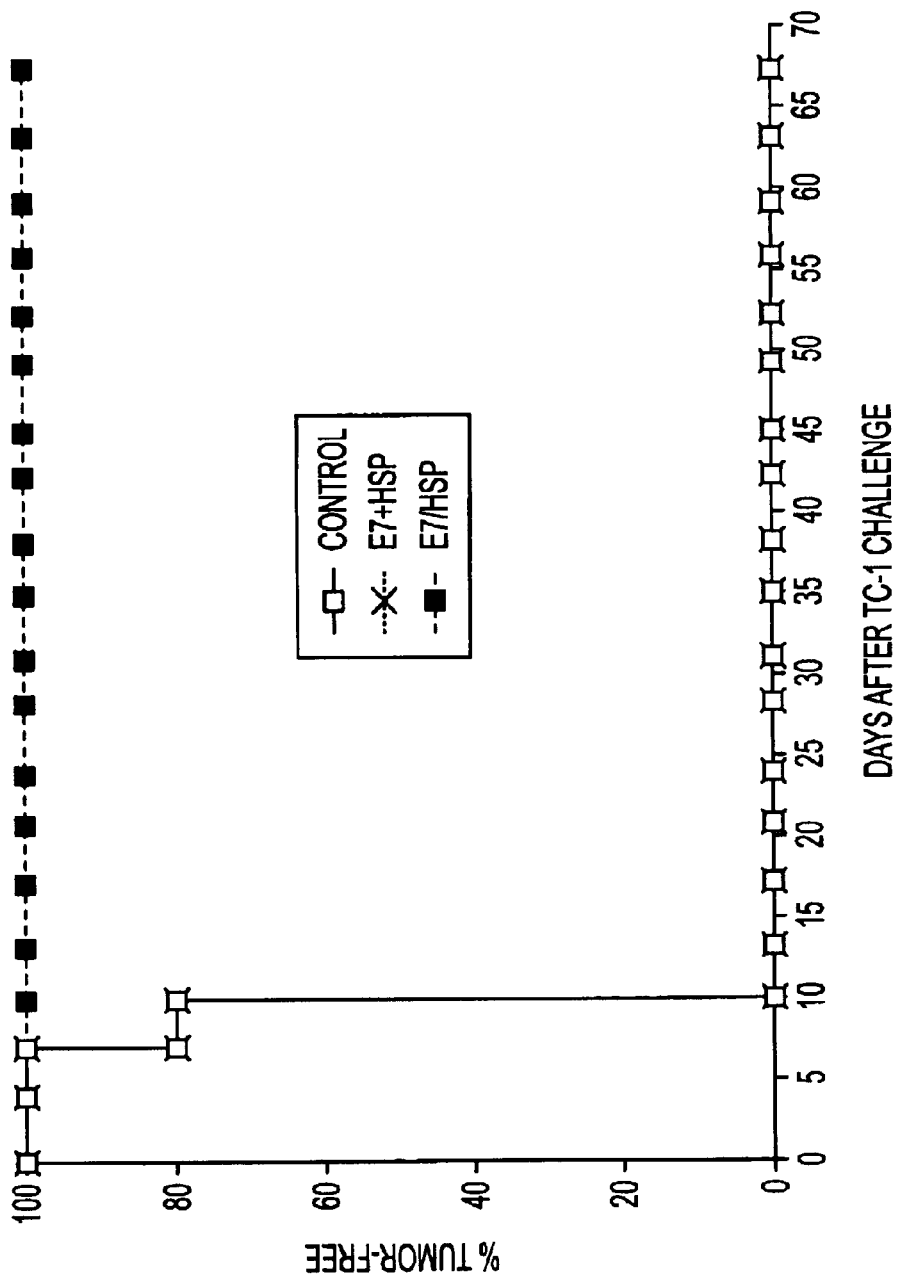

FIG. 6 is a line graph showing that the antitumor immunity generated by E7-HSP70 DNA requires the fusion of HSP70 DNA sequences to E7 gene sequences. C57BL/6 mice were immunized with E7-HSP70 DNA(E7/HSP), or E7 DNA mixed with HSP70 DNA (E7+ HSP) via gene gun, or received no vaccination. For vaccinated mice, 2 μg DNA /mouse was given only once. One week after the vaccination, mice were challenged with 5×10$^4$ TC-1 cells/ mouse subcutaneously in the right leg. The mice were monitored for evidence of tumor growth by palpation and inspection twice a week.

Figure 7:
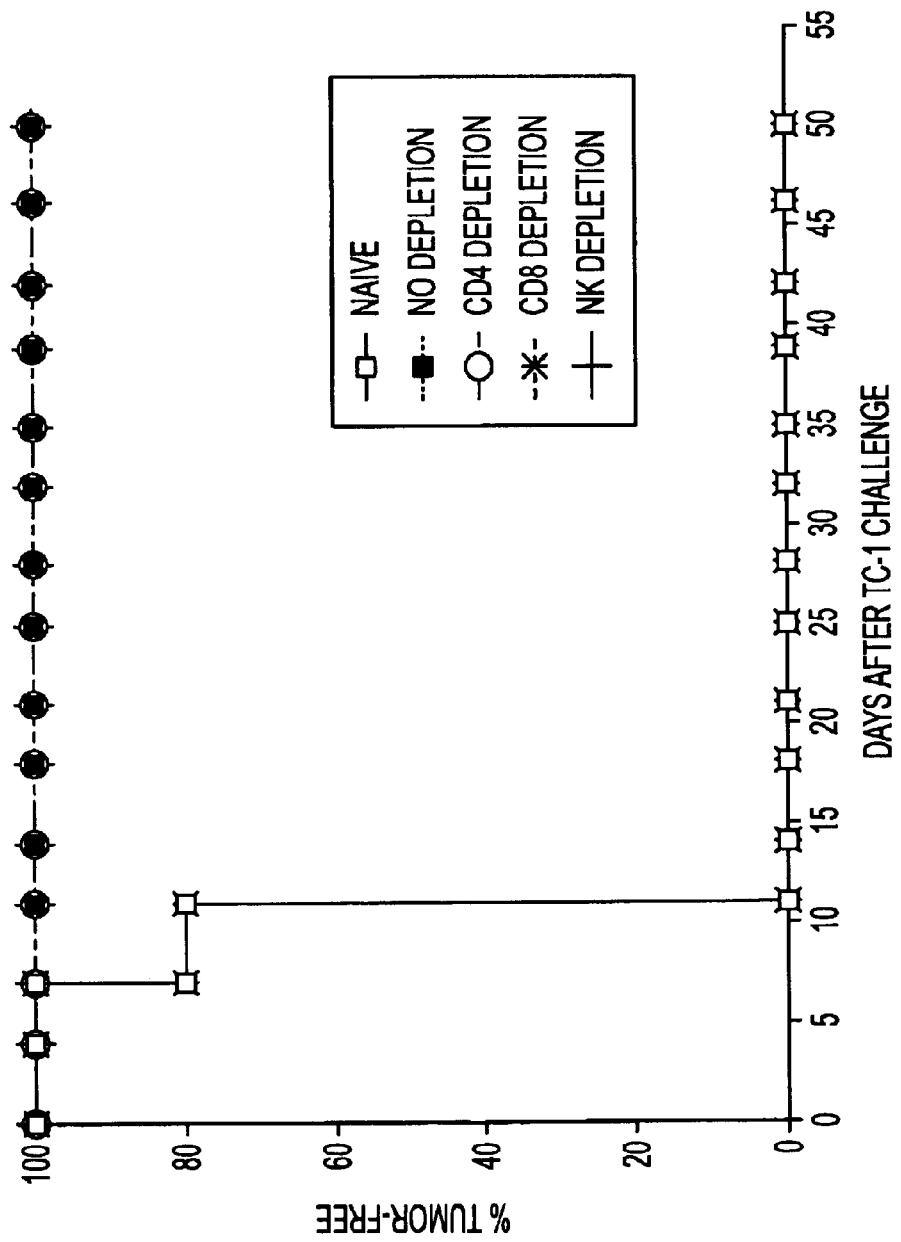

FIG. 7 is a line graph showing the effect of lymphocyte subset depletions on the potency of E7-HSP70 DNA vaccine. C57BL/6 mice were immunized with 2 μg E7-HSP70 DNA via gene gun and boosted with 2 μg E7-HSP70 DNA one week later. Two weeks after the last vaccination, mice were challenged with 5×10$^4$ TC-1 cells/ mouse subcutaneously in the right leg. Cell depletions were initiated one week prior to tumor challenge and lasted 40 days after tumor challenge. MAb GK1.5 was used for CD4 depletion, MAb 2.43 was used for CD8 depletion, and MAb PK136 was used for NK1.1 depletion. Flow cytometry analysis revealed that the greater than 95% of the appropriate lymphocytes subset were depleted with normal level of other subsets. The mice were monitored for evidence of tumor growth by palpation and inspection twice a week.

Figure 8:
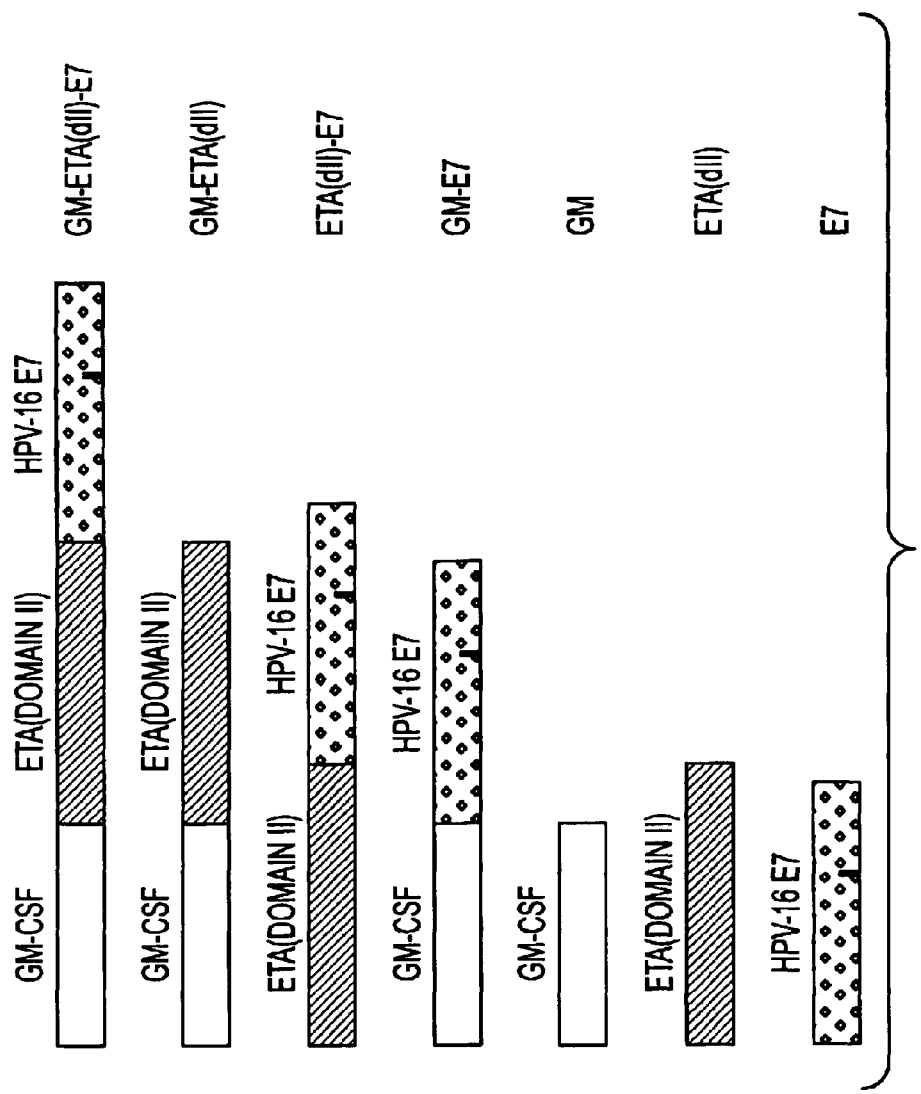

FIG. 8 is a diagram of constructs of GM-ETA(dII)-E7, GM-ETA(dII), ETA(dII)-E7, GM-E7, GM-CSF, ETA(dII), E7.

Figure 9:
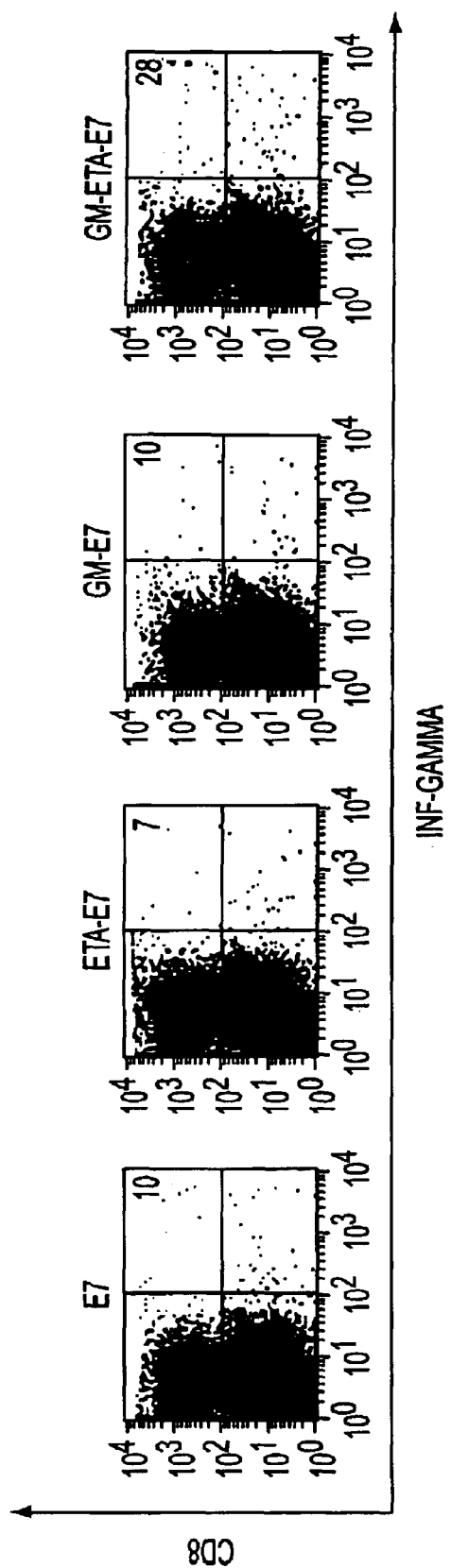

FIG. 9 is a diagram of a flow cytometry analysis showing intracellular cytokine staining which was carried out to determine E7-specific CD8+ T cell precursors in C57BL/6 mice immunized with GM-ETA(DII)-E7 DNA vaccines. C57BL/6 mice were immunized with Plasmid DNA with GM, ETA(dII), E7, GM-ETA(dII), ETA(DII)-E7, GM-E7 or GM-ETA(DII)-E7 gene insert or the "empty" plasmid vector intradermally via gene gun, or received no vaccination. For vaccinated mice, 2 µg DNA /mouse was given twice. Splenocytes were harvested 10 days after the last DNA vaccination. Splenocytes from vaccinated mice were cultured in vitro with E7 peptide (residues 49–57; SEQ ID NO:5) overnight and were stained for both CD8 and intracellular IFN-γ. The number of IFN-γ secreting CD8+ T cell precursors in mice immunized with various recombinant DNA vaccines was analyzed by flow cytometry. Mice vaccinated with GM-ETA(DII)-E7 DNA generated the highest IFN-γ+ CD8+ double positive T cells.

Figure 10:
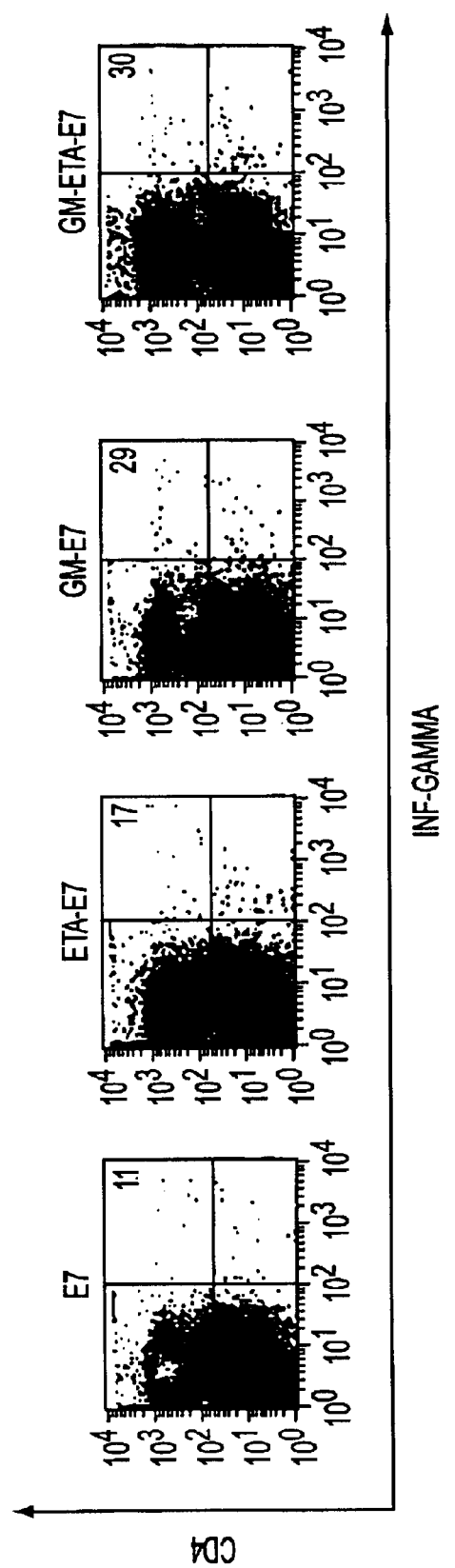

FIG. 10 is a diagram showing flow cytometry analysis of IFN-γ secreting E7-specific CD4+ cells in mice vaccinated with various recombinant DNA vaccines. C57BL/6 mice were immunized as described above for FIG. 2. Splenocytes from vaccinated mice were cultured in vitro with E7 peptide (residues 30–67; SEQ ID NO:6) overnight and were stained for both CD4 and intracellular IFN-γ. The number of IFN-γ secreting CD4+ T cells was analyzed by flow cytometry. Mice vaccinated with GM-ETA(DII)-E7 DNA generated comparable CD4+ IFN-γ+ double positive cells when compared to mice vaccinated with GM-E7 DNA. Mice vaccinated with GM-ETA (dII)-E7 generated greater number E7-specific CD4+ IFN-γ+ double positive cells than mice immunized with empty plasmid (pcDNA3), GM-ETA(dII), ETA(dII)-E7, GM-E7, GM-CSF, ETA(dII), or E7 DNA.

Figure 11:
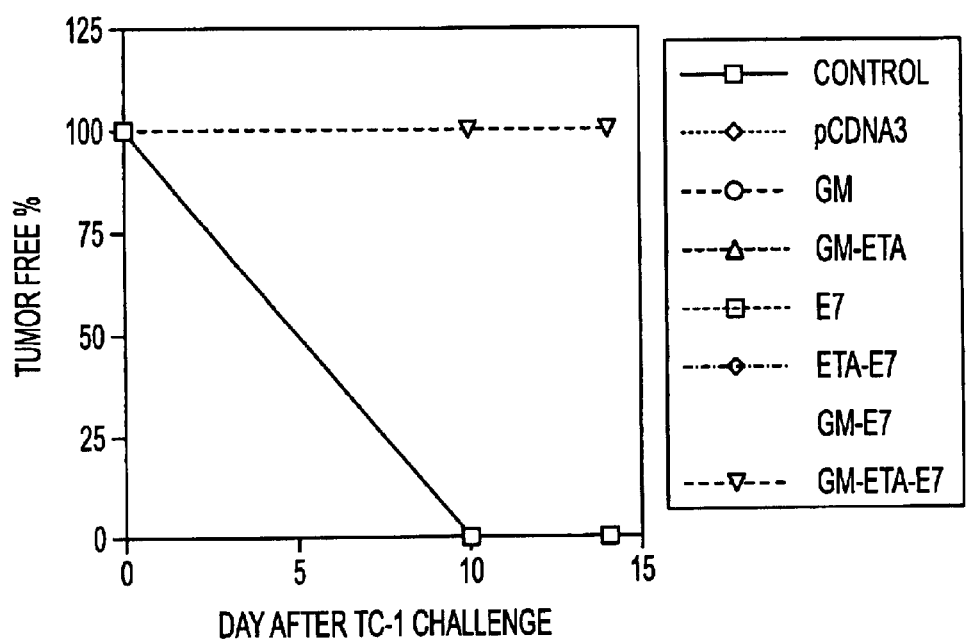

FIG. 11 is a line graph showing that vaccination with GM-ETA(DII)-E7 DNA protects mice against the growth of TC-1 tumors. C57BL/6 mice were immunized with 2 µg/mouse of empty plasmid (pcDNA3), GM-ETA(dII), ETA (dII)-E7, GM-E7, GM-CSF, ETA(dII), E7 DNA, or GM-ETA(dII)-E7 DNA via gene gun. One week later, the mice were re-vaccinated with the same type and amount of DNA as the first vaccination. One week after the last vaccination, mice were challenged with 5×10⁴ TC-1 cells per mouse subcutaneously in the right leg. The mice were monitored for evidence of tumor growth by palpation and inspection twice a week. At day 60 after TC-1 challenge, tumor-free mice were rechallenged with 5×10⁴ TC-1 cells/ mouse subcutaneously in the left leg.

Figure 12:
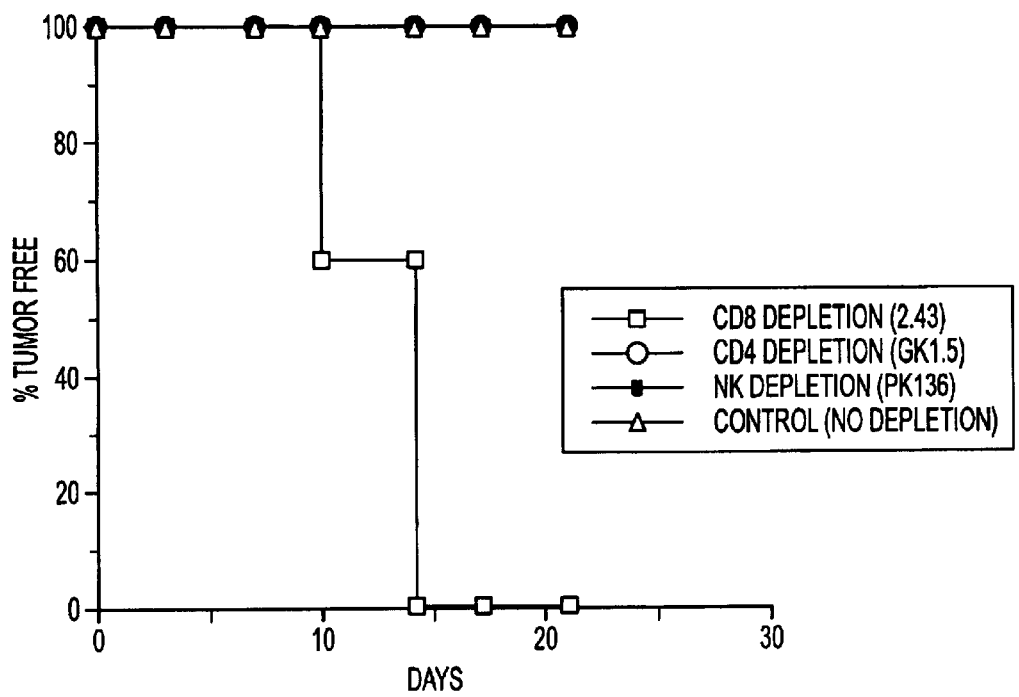

FIG. 12 is a line graph showing the effect of lymphocyte subset depletions on the potency of GM-ETAdII-E7 DNA vaccine. C57BL/6 mice were immunized with 2 µg GM-ETAdII-E7 DNA via gene gun and boosted with 2 µg GM-ETAdII-E7 DNA one week later. Two weeks after the last vaccination, mice were challenged with 5×10⁴ TC-1 cell per mouse subcutaneously in the right leg. Depletions were initiated one week prior to tumor challenge and lasted the indicated number of days after tumor challenge. MAb GK1.5 (Dialynas et al., 1983, J. Immunol. 131:2445–2451) was used for CD4 depletion, MAb 2.43 (Sarmiento et al., 1980, J. Immunol. 125:2665–2672) was used for CD8 depletion, and MAb PK136 (Koo et al., 1986, J. Immunol. 137:3742–3747) was used for NK1.1 depletion. Flow cytometry analysis revealed that the >95% of the appropriate lymphocytes subset were depleted with normal level of other subsets. The mice were monitored for evidence of tumor growth by palpation and inspection twice a week.

FIG. 13 is a diagram of the amino acid and nucleotide sequence of the E7-HSP70 immunogenic construct.

FIG. 14 is a diagram of the amino acid and nucleotide sequence of the GM-ETA(dII)-E7 immunogenic construct. The GM-CSF portion, ETA(dII), and E7 portions of the construct are indicated with brackets.

FIG. 15 is a diagram of the amino acid and nucleotide sequence of ETA (without the signal sequence). Residues 247–417 (and corresponding nucleotide sequences) used in making the immunogenic construct are bracketed.

FIG. 16 is a diagram showing the domain structure of full-length *Mycobacterium tuberculosis* HSP70 protein (SEQ ID NO:9). The ATPase domain (residues 1–356) is underlined; the substrate binding domain (SD; residues 357–516) is in italics, and C-terminal domain (CD: residues 517–625) is in bold type.

Figure 17:
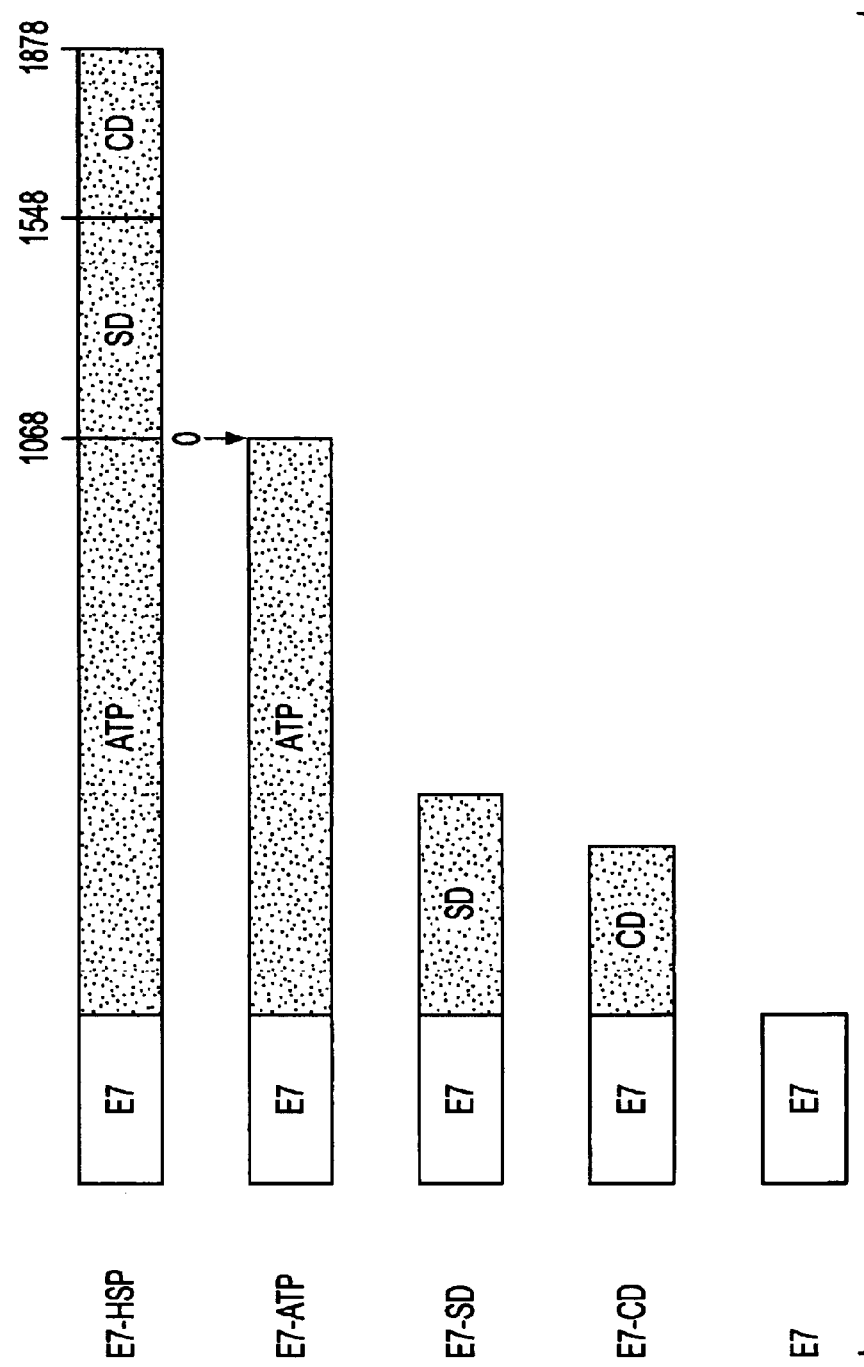

FIG. 17 is a diagram of plasmid constructs in a mammalian cell expression vector. All of the chimeric E7/heat shock protein constructs (E7-HSP70, E7-ATP, E7-SD, E7-CD, and E7) were cloned into multiple cloning sites of an expression vector downstream of the cytomegalovirus promoter.

Figure 18B:
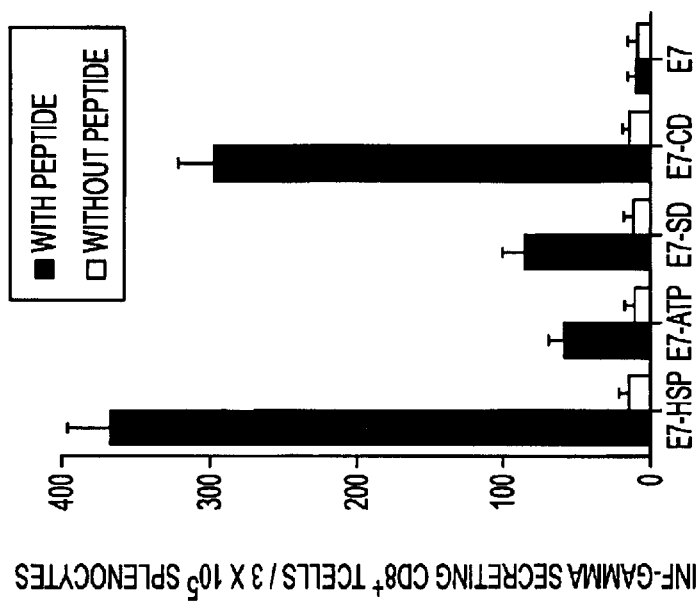
Figure 18A:

FIG. 18A is a diagram of a flow cytometry analysis of IFN-γ E7-specific CD8+ cells in mice immunized with recombinant DNA vaccines containing nucleic acid constructs encoding Hsp fragment-antigen chimeras (E7-HSP70, E7-ATP, E7-SD, E7-CD, and E7).

FIG. 18B is a bar graph showing mean number of IFN-γ-producing E7-specific CD8+ T cells.

Figure 19:
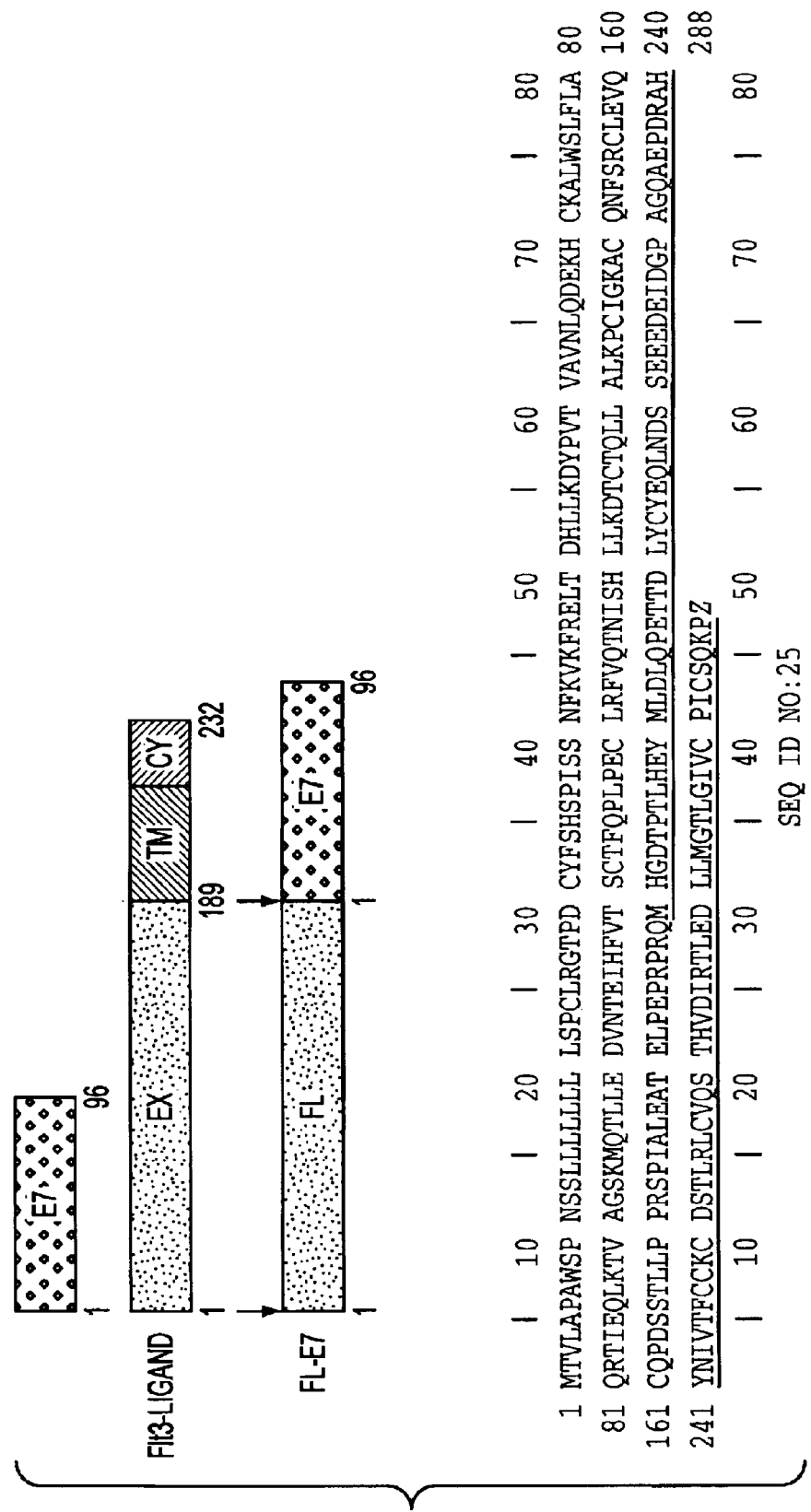

FIG. 19 is a diagram of plasmid constructs in a mammalian cell expression vector.

DESCRIPTION OF THE PREFERRED EMBODIMENTS

The invention provides polynucleotides which, when directly introduced into a mammal in vivo induce the expression of an encoded polypeptide(s) within the animal and, in turn, a CD8+ immune response specific for the encoded polypeptide. The polynucleotide is a nucleic acid which contains essential regulatory elements such that upon introduction into a living vertebrate cell, the cell is able to produce translation products encoded by the polynucleotide. For example, the polynucleotide is a polydeoxyribonucleic acid containing DNA encoding a heat shock protein or a fragment thereof. The DNA encoding an antigenic polypeptide to which an immune response is desired is operatively linked to a transcriptional promoter. In some cases, the antigen which is encoded by the polynucleotide is one which does not normally occur in that animal except in pathological conditions, (i.e. an heterologous protein associated with a virus). In other cases, the antigen is an autologous polypeptide, e.g., a tumor-associated antigen, that is misregulated in a disease state. The polypeptides encoded by the DNA vaccine are produced by the animals' own tissues, and the expressed proteins are processed by the major histocompatibility system (MHC). The polynucleotides are preferably ligated into an expression vector which has been specifically optimized for polynucleotide vaccinations. Regulatory elements include a transcriptional promoter, immunogenic epitopes, and additional cistrons encoding immunoenhancing or immunomodulatory genes, with their own promoters, transcriptional terminator, bacterial origin of replication and/or antibiotic resistance gene. The vector may also contain internal ribosome entry sites (IRES) for the expression of polycistronic mRNA. Transcriptional promoters include such powerful RNA polymerase promoters as the T7 or SP6 promoters.

The polynucleotide and DNA vaccines described herein elicit protective immunity against the antigens encoded. For example, the injection of a DNA expression vector encoding antigen E7 results death of tumor cells or a decrease in tumor cell growth. Antigen-specific CTLs against the tumor cells are produced following vaccination.

A number of advantages are associated with the vaccination strategy of the invention. A drawback of many known DNA vaccines is their limited potency. In contrast to standard DNA vaccines, the polynucleotides of the invention and the methods of vaccination yield potent antigen-specific immunotherapy. The polynucleotides and DNA vaccines of the invention induce a CTL response that is at least 2-fold, preferably at least 10-fold, more preferably at least 20-fold, more preferably at least 30-fold, and most preferably at least 40-fold more potent than conventional DNA vaccines (e.g., those that do not contain sequences encoding an APC-binding domain or a cytoplasmic translocation domain). Vaccine potency is determined by methods known in the art, e.g., by measuring $CD8^+$ T cell precursors induced after vaccination or by measuring a reduction in tumor load after vaccination, as described herein. Polypeptides encoded in a DNA vaccine may have the potential to enter the MHC class I pathway and evoke a cytotoxic T cell response. The DNA vaccine of the invention is specifically designed to direct the immunogen into the MHC class I antigen processing pathway by encoding a cytoplasmic translocation domain. As a result, elicitation of a cytotoxic T cell response is optimized.

Other advantages include safety and simplicity of large scale production. The vaccines of the present invention are safe and useful for administration to domesticated or agricultural animals, as well as humans. For example, naked plasmid DNA is safe, has low immunogenicity, and can be repeatedly administered. DNA vaccines are easily prepared in large scale with high purity and are highly stable relative to proteins and other biologic polymers.

The amount of expressible DNA or transcribed RNA to be introduced into a vaccine recipient may vary depending on the strength of the transcriptional and translational promoters used. In addition, the magnitude of the immune response may depend on the level of protein expression and on the immunogenicity of the expressed gene product. In general, an effective dose ranges of about 1 ng to 5 mg, 100 ng to 2.5 mg, 1 $\mu$g to 750 $\mu$g, and preferably about 10 $\mu$g to 300 $\mu$g of DNA is administered directly into a bodily tissue, such as muscle or dermal tissue. A preferred dosage for intravenous administration of DNA is approximately $10^6$ to $10^{22}$ copies of the DNA molecule. Subcutaneous injection, intradermal introduction, impression through the skin, and other modes of administration such as intraperitoneal, intravenous, or inhalation delivery are also suitable. For example, DNA is administered using a gene gun. Booster vaccinations are administered in the same mannner. DNA vaccines are also formulated to be delivered as part of a Listeria monocytogenes vaccine using known methods, e.g., those described in Pan et al., 1995, Cancer Res. 55(21):4776–4779 and Pan et al., 1995, Nature Med. 1(5):471–7. Following vaccination with a polynucleotide immunogen, the immune response may also be boosted by administering the polypeptide immunogen.

The polynucleotide may be naked, that is, unassociated with any proteins, adjuvants or other agents which affect the recipients' immune system. Naked DNA is administered in a physiologically acceptable solution, such as sterile saline or sterile buffered saline. Alternatively, the DNA may be associated with liposomes, such as lecithin liposomes or as a DNA-liposome mixture. Agents which assist in the cellular uptake of DNA (i.e., transfection facilitating agents), such as calcium ions may also be used. Microprojectiles coated with a polynucleotide are also useful as a means of administering the vaccine.

Functional Components of the Immunogenic Composition

The polynucleotide contains contiguous nucleic acid sequences capable of being expressed to produce a chimeric gene product with three functional domains: (1) an APC-binding domain; (2) a cytoplasmic translocation domain; and (3) an antigenic epitope. For example, the antigenic epitope is a MHC Class I-restricted epitope. The encoded gene product generates a potent immune response. The response is more potent than administering the chimeric gene product and more potent than administering a DNA vaccine which encodes the MHC class I-restricted epitope without an APC-binding portion or a cytoplasmic translocation portion.

Domains of HSP70 Which Confer Enhancement of Antigen-Specific Immune Responses

The domain structure of HSP70 was determined. At least three functional domains were identified: an ATPase domain (containing residues 1–356 of-SEQ ID NO:9), substrate binding domain (SD; containing residues 357–516 of SEQ ID NO:9) and a carboxyterminal domain (CD; containing residues 517–625 of SEQ ID NO:9) (FIG. 16). The contribution of each domain of *Mycobacterium tuberculosis* HSP70 on the potency of naked DNA vaccines was determined. DNA encoding each domain was linked in frame, i.e., operably linked, to DNA encoding the antigen E7. E7-specific CD8 T cell immune responses were measured.

A standard gene gun DNA delivery method was used to vaccinate C57BL/6 mice intradermally with DNA vaccines containing (i) HSP70 gene; (ii) wild-type HPV-16 E7 gene; (iii) HPV-16 E7 gene fused to the ATPase domain of HSP70 (E7-ATP); (iv), HPV-16 E7 gene fused to the substrate binding domain (SD) of HSP70 (E7-SD); or (v) IIPV-16 E7 gene fused to the cytoplasmic domain (CD) of HSP70 (E7-CD). All of the chimeric E7/heat shock protein constructs were cloned into the multiple cloning sites of the pcDNA3.1(−) expression vector downstream of the cytomegalovirus promoter (FIG. 17). The in vivo antitumor immune responses were analyzed by intracellular cytokine staining using E7-specific MHC class I peptide (RAHYNIVTF; amino acids 49–57 of SEQ ID NO:7) to assess the E7-specific CD8+ T cell-mediated immunity.

FIG. 18A is a representative FASCAN showing E7-specific CD8+ T cell precursor frequencies. Splenocytes from vaccinated mice were cultured in vitro with the E7 peptide (amino acids 49–57 of SEQ ID NO:7) overnight and were stained for both CD8 expression and intracellular IFN-γ. The number of IFN-γ secreting CD8+ T cell precursors in mice immunized with various DNA constructs (E7-HSP70, E7-ATP, E7-SD, E7-CD, or E7 alone) was analyzed using flow cytometry. Mice vaccinated with E7-HSP70 DNA generated the highest number of E7-specific CD8+ precursors. E7-CD generated the second highest quantity of E7-specific CD8+ precursors, comparable to E7-HSP70 (and greater than E7-SD, E7-ATP, and wild-type E7).

Mean number of IFN-γ-producing E7-specific CD8+ T cells is shown in FIG. 18B. The number of cells wer determined by flow cytometry. in the presence (solid bars) and absence (open bars) of the E7 antigen peptide (residues 49–57 of SEQ ID NO:7). The data was expressed as mean number of CD8+ IFN-γ+ cells/$3\times10^5$ splenocytes±SEM. The results indicate that when incorporated into a DNA vaccine construct, DNA encoding a cytoplasmic domain of HSP70 increases the potency of the DNA vaccine in generating immunity to the target antigen encoded by the vaccine. Moreover, the cytoplasmic domain accounts for most of the enhancement of antigen specific MHC class I restricted CD8+T cell immune responses in DNA vaccines which contain full length HSP70.

For example, vaccination with E7 fused to full length HSP70 led to a 30-fold increase in E7-specific CD8+ T cell precursor frequencies (approximately 365 per $3\times10^5$ splenocytes) (FIGS. 18A–B). Vaccination with E7 fused to the ATP domain of HSP70 generated slightly increased E7-specific CD8+ T cell precursor frequencies (approximately 58 per $3\times10^5$) splenocytes). Similarly, vaccination with E7 fused to the SD domain of HSP70 generated approximately 85 E7-specific CD8+ T cell precursors per $3\times10^5$ splenocytes. In contrast, vaccination with E7 fused to the CD domain of HSP70 generated approximately 296 E7-specific CD8+ T cell precursors per $3\times10^5$ splenocytes, an amount similar to that obtained from mice vaccinated with E7 fused to full length HSP70. These results indicated the CD domain of HSP70 confers most of the enhanced antigen-specific MHC class I restricted CD8+ T cell immune responses in DNA vaccines.

These data demonstrate that DNA encoding a fusion of full-length HSP70 or the CD domain of HSP70 (in the absence of DNA encoding other portions of HSP70) to an antigenic peptide (e.g., HPV-16 E7) greatly enhances antigen-specific CD8+ T cell immune responses to the antigen. The enhancement of immune responses was observed in constructs which lacked more N-terminal sequences in the region of the ATPase domain (e.g., residues 161–370 of SEQ ID NO:9) which were thought to be important in stimulating a CTL response. The data indicate that DNA vaccines containing constructs encoding the CD domain of HSP, even in the absence of other HSP sequences, enhanced antigen-specific MHC class I restricted CD8+ T cell immune responses to a target antigen encoded by the DNA vaccine.

EXAMPLE 1

Enhancement of DNA Vaccine Potency by Linkage of Antigen Gene to an HSP70 Gene

Using HPV-16 E7 as a model antigen, the data described herein indicate that a DNA vaccine which contains a polynucleotide encoding chimeric polypeptide with an APC-bind portion, cytoplasmic translocation portion, and class I MHC epitope results in potent immunity specific for the epitope. The effect of linkage to *Mycobacterium tuberculosis* heat shock protein 70 (HSP70) on the potency of antigen-specific immunity generated by naked DNA vaccines was evaluated.

*M. tuberculosis* HSP70 dramatically enhances the potency of HPV-16 E7-expressing DNA vaccines. DNA vaccines with HSP70 fused to HPV-16 E7 elicited strong E7-specific cellular immunity (at least 30-fold increase in the E7-specific CD8+ T cells precursor frequencies) and generated a significant $CD8^+$ T cell-dependent preventive and therapeutic effects against HPV-16 E7-expressing murine tumors.

The data indicated that HSP70 preferentially enhances $CD8^+$ T cell responses of E7 DNA vaccines. In contrast, $CD4^+$ T cell responses were not detectably enhanced by HSP70 linkage. This was demonstrated by a failure to induce detectable IFN-γ-expressing CD4+ T cells by flow cytometry and a failure to induce E7-specific antibodies. DNA vaccines encoding E7-HSP70 fusion genes increased the frequency of E7-specific CD8+ T cells by 40-fold relative to vaccines containing the wild type E7 gene (in the absence of HSP70 gene sequences). More importantly, the addition of HSP70 gene sequences to a conventional DNA vaccine (e.g., one encoding the antigen alone) converted a less effective vaccine into one with significant potency against established E7-expressing tumors. Surprisingly, E7-HSP70 fusion vaccines exclusively targeted CD8+ T cells; immunologic and antitumor effects were completely CD4 independent. These results indicate that fusion of HSP70 to an antigen gene greatly enhances the potency of DNA vaccines via CD8 dependent pathways.

HPV-derived antigens were chosen because HPVs, particularly HPV-16, are associated with most cervical cancers. The HPV oncogenic proteins, E6 and E7, are important in the induction and maintenance of cellular transformation and co-expressed in most HPV-containing cervical cancers. Vaccines or immunotherapies targeting E7 and/or E6 proteins can prevent and treat HPV-associated cervical malignancies. The data indicate that linking antigen-encoding polynucleotides, e.g., full-length E7-encoding sequences, to HSP-encoding sequences enhances the potency of DNA vaccines. DNA vaccines containing wild type HPV-16 E7 with DNA vaccines containing full-length E7 fused to *Mycobacterium tuberculosis* HSP70 were evaluated for their immune response generation and their ability to protect animals against the HPV-16 E7-expressing murine tumors. Linking DNA encoding E7 to DNA encoding HSP70 dramatically increases expansion and activation of E7-specific CD8+ T cells, completely bypassing the CD4 arm. This enhanced CD8 response results in potent antitumor immunity against established tumors.

The following materials and methods were used to generate the data described below.

Plasmid DNA Constructs and Preparation

DNA fragment encoding *Mycobacterium tuberculosis* HSP70 is known in the art (GENBANK® Accession No. Z95324 AL123456; nucleotides 10633–12510 encode HSP70).

TABLE 1

Amino acid sequence of HSP70

MARAVGIDLGTTNSVVSVLEGGDPVVVANSEGSRTTPSIVAFAR
NGEVLVGQPAKNQAVTNVDRTVRSVKRHMGSDWSIEIDGKKYTAPEISARILMKLKRD

TABLE 1-continued

Amino acid sequence of HSP70

AEAYLGEDITDAVITTPAYFNDAQRQATKDAGQIAGLNVLRIVNEPTAAALAYGLDKG
EKEQRILVFDLGGGTFDVSLLEIGEGVVEVRATSGDNHLGGDDWDQRVVDWLVDKFKG
TSGIDLTKDKMAMQRLREAAEKAKIELSSSQSTSINLPYITVDADKNPLFLDEQLTRA
EFQRITQDLLDRTRKPFQSVIADTGISVSEIDHVVLVGGSTRMPAVTDLVKELTGGKE
PNKGVNPDEVVAVGAALQAGVLKGEVKDVLLLDVTPLSLGIETKGGVMTRLIERNTTI
PTKRSETFTTADDNQPSVQIQVYQGEREIAAHNKLLGSFELTGIPPAPRGIPQIEVTF
DIDANGIVHVTAKDKGTGKENTIRIQEGSGLSKEDIDRMIKDAEAHAEEDRKRREEAD
VRNQAETLVYQTEKFVKEQREAEGGSKVPEDTLNKVDAAVAEAKAALGGSDISAIKSA
MEKLGQESQALGQAIYEAAQAASQATGAAHPGGEPGGAHPGSADDVVDAEVVDDGREAK
(SEQ ID NO:9, GENBANK Z95324 AL123456; encoded by nucleotides
10633-12510 of Mycobacterium tuberculosis genome)

TABLE 2

Nucleotide sequence encoding HSP70

```
    atggctcg tgcggtcggg atcgacctcg ggaccaccaa ctccgtcgtc tcggttctgg
   aaggtggcga cccggtcgtc gtcgccaact ccgagggctc caggaccacc ccgtcaattg
   tcgcgttcgc ccgcaacggt gaggtgctgg tcggccagcc cgccaagaac caggcagtga
   ccaacgtcga tcgcaccgtg cgctcggtca agcgacacat gggcagcgac tggtccatag
   agattgacgg caagaaatac accgcgccgg agatcagcgc ccgcattctg atgaagctga
   agcgcgacgc cgaggcctac ctcggtgagg acattaccga cgcggttatc acgacgcccg
   cctacttcaa tgacgcccag cgtcaggcca ccaaggacgc cggccagatc gccggcctca
   acgtgctgcg gatcgtcaac gagccgaccg cggccgcgct ggcctacggc ctcgacaagg
   gcgagaagga gcagcgaatc ctggtcttcg acttgggtgg tggcactttc gacgtttccc
   tgctggagat cggcgagggt gtggttgagg tccgtgccac ttcgggtgac aaccacctcg
   gcggcgacga ctgggaccag cgggtcgtcg attggctggt ggacaagttc aagggcacca
   gcggcatcga tctgaccaag gacaagatgg cgatgcagcg gctgcgggaa gccgccgaga
   aggcaaagat cgagctgagt tcgagtcagt ccacctcgat caacctgccc tacatcaccg
   tcgacgccga caagaacccg ttgttcttag acgagcagct gacccgcgcg gagttccaac
   ggatcactca ggacctgctg gaccgcactc gcaagccgtt ccagtcggtg atcgctgaca
   ccggcatttc ggtgtcggag atcgatcacg ttgtgctcgt gggtggttcg acccggatgc
   ccgcggtgac cgatctggtc aaggaactca ccggcggcaa ggaacccaac aagggcgtca
   accccgatga ggttgtcgcg gtgggagccg ctctgcaggc cggcgtcctc aagggcgagg
   tgaaagacgt tctgctgctt gatgttaccc cgctgagcct gggtatcgag accaagggcg
   gggtgatgac caggctcatc gagcgcaaca ccacgatccc caccaagcgg tcggagactt
   tcaccaccgc cgacgacaac caaccgtcgg tgcagatcca ggtctatcag ggggagcgtg
   agatcgccgc gcacaacaag ttgctcgggt ccttcgagct gaccggcatc ccgccggcgc
   cgcgggggat tccgcagatc gagtcactt tcgacatcga cgccaacggc attgtgcacg
   tcaccgccaa ggacaagggc accggcaagg agaacacgat ccgaatccag gaaggctcgg
   gcctgtccaa ggaagacatt gaccgcatga tcaaggacgc cgaagcgcac gccgaggagg
   atcgcaagcg tcgcgaggag gccgatgttc gtaatcaagc cgagacattg gtctaccaga
   cggagaagtt cgtcaaagaa cagcgtgagg ccgagggtgg ttcgaaggta cctgaagaca
   cgctgaacaa ggttgatgcc gcggtggcgg aagcgaaggc ggcacttggc ggatcggata
   tttcggccat caagtcggcg atggagaagc tgggccagga gtcgcaggct ctggggcaag
   cgatctacga agcagctcag gctgcgtcac aggccactgg cgctgcccac cccggcggcg
   agccgggcgg tgcccacccc ggctcggctg atgacgttgt ggacgcggag gtggtcgacg
   acggccggga ggccaagtga (SEQ ID NO:10; nucleotides 10633-12510 of
GENBANK Accession No. Z95324 AL123456)
```

For the generation of HSP-expressing plasmid (pcDNA3-HSP), HSP70-encoding DNA was subcloned from pKS70 into the unique BamHI and HindIII cloning sites of the pcDNA3.1(–) expression vector (Invitrogen, Carlsbad, Calif.) downstream of the cytomegalovirus promoter. For the generation of HPV-16 E7-expressing plasmid (pcDNA3-E7), E7 DNA was amplified by PCR using primers designed to generate BamHI and HindIII restriction sites at the 5' and 3' ends of the amplified fragments respectively. The amplified E7 DNA was then cloned into the unique BamHI and HindIII cloning sites of the pcDNA3.1. For the generation of E7-HSP70 chimera (pcDNA-E7-HSP70), E7 DNA was amplified by PCR using primers designed to generate BamHI restriction sites at both 5' and 3' ends of the amplified fragments. The E7 DNA was then subcloned to the 5' end of pcDNA3-HSP. The accuracy of these constructs was confirmed by DNA sequencing. Plasmid DNA with HSP, E7 or E7-HSP70 gene insert and the "empty" plasmid vector were transfected into subcloning efficient DH5 (TM cells; Life Technologies, USA). The DNA was then amplified and purified using double CsCl purification (BioServe Biotechnologies, Laurel, Md.). The integrity of plasmid DNA and the absence of Escherichia coli DNA or RNA were checked in each preparation using 1% agarose gel electrophoresis. DNA concentration was determined by the optical density measured at 260 nm. The presence of the inserted E7 fragment was confirmed by restriction enzyme digestion and gel electrophoresis. Reticulum and calreticulum polypeptides (and polynucleotides encoding them) are a useful alternative to the HSP component of the immunogenic composition.

TABLE 3

Amino acid sequence of HPV16 E7 antigen

MHGDTPTLHEYMLDLQPETTDLYCYEQLNDSSEEEDEIDGPAGQAEPDRAHYNIVTFCCK
CDSTLRLCVQ STHVDIRTLEDLLMGTLGIVCPICSQKP (SEQ ID NO:7,
GENBANK Accession No. AAD33353)

TABLE 4

Nucleotide sequence encoding HPV E7

```
 atgcatgga gatacaccta cattgcatga atatatgtta gatttgcaac cagagacaac
tgatctctac tgttatgagc aattaaatga cagctcagag gaggaggatg aaatagatgg
tccagctgga caagcagaac cggacagagc ccattacaat attgtaacct tttgttgcaa
gtgtgactct acgcttcggt tgtgcgtaca aagcacacac gtagacattc gtactttgga
agacctgtta atgggcacac taggaattgt gtgccccatc tgttctcaga aaccataa
(SEQ ID NO:8; nucleotides 562–858 of GENBANK Accession No.
AF125673)
```

DNA Vaccination

Gene gun particle-mediated DNA vaccination was performed using a helium-driven gene gun (Bio-rad, Hercules, Calif., according to the standard protocols. Briefly, DNA coated gold particles were prepared by combining 25 mg of 1.6 μm gold microcarriers (Bio-rad, Hercules, Calif.) and 100 μl of 0.05 M spermidine (Sigma, St, Louis, Mo. Plasmid DNA (50 μg) and 1.0 M $CaCl_2$ (100 μl) were added sequentially to the microcarriers while mixing by vortex. This mixture was allowed to precipitate at room temperature for 10 minutes. The microcarrier/DNA suspension was then centrifuged (10,000 r.p.m. for 5 sec) and washed 3 times in fresh absolute ethanol before resuspending in 3 ml of polyvinylpyrrolidone (0.1 mg/ml) (Bio-rad, Hercules, Calif.) in absolute ethanol. The solution was then loaded into tubing and allowed to settle for 4 min. The ethanol was gently removed and the microcarrier/DNA suspension was evenly attached to the inside surface of the tubing by rotating the tube. The tube was then dried by 0.4 liters per minute of flowing nitrogen gas. The dried tubing coated with microcarrier/DNA was then cut to 0.5-inch cartridges and stored in a capped dry bottle at 4° C. As a result, each cartridge contained 1 μg of plasmid DNA and 0.5 mg of gold. The DNA coated gold particles (1 μg DNA/bullet) were delivered to the shaved abdominal region of the mice using a helium-driven gene gun (Bio-rad, Hercules, Calif.) with a discharge pressure of 400 p.s.i.

ELISPOT Assay

A standard ELISPOT assay was used to detect HPV-16 E7-specific CD8+ T cell. The 96-well filtration plates (Millipore, Bedford, Mass. were coated with 10 μg/ml rat anti-mouse IFN-γ antibody (clone R4–6A2, Pharmingen, San Diego, Calif.) in 50 μl of phosphate-buffered saline (PBS). After overnight incubation at 4° C., the wells were washed and blocked with culture medium containing 10% fetal bovine serum. Different concentrations of fresh isolated spleen cells from each vaccinated mice group, starting from $1 \times 10^6$/well, were added to the well along with 15 U/ml interleukin-2. Cells were incubated at 37° C. for 24 hours either with or without 1 μg/ml E7 specific H-2Db CTL epitope (E7, residues 49–57; SEQ ID NO:5). After culture, the plate was washed and then the cells were incubated with 5 μg/ml biotinylated IFN-γ antibody (clone XMG1.2, Pharmingen) in 50 μl in PBS at 4° C. overnight. After washing six times, 1.25 μg/ml-avidin-alkaline phosphatase (Sigma, St. Louis, Mo. in 50 μl PBS, were added and incubated for 2 hours at room temperature. After washing, spots were developed by adding 50 μl BCIP/NBT solution (Boehringer Mannheim, Indianapolis, Ind.) and incubated at room temperature for 1 hr. The spots were counted using a dissecting microscope.

Intracytoplasmic Cytokine Staining and Flow Cytometry

Splenocytes from naive or vaccinated groups of mice were incubated either with the E7 peptide (residues 49–57; SEQ ID NO:5) that contains MHC class I epitope or the E7 peptide (residues 30–67; SEQ ID NO:6) that contains MHC class II peptide. Methods of determining which residues of a protein or polypeptide represent a MHC class I antigenic epitope are well known in the art. The E7 peptide was added at a concentration of 2 μg/ml for 20 hours. To detect E7-specific $CD8^+$ T cell precursors and E7-specific $CD4^+$ T helper cell responses, $CD8^+$ CTL epitopes residues 49–57 and residues 30–67 were used, respectively. Golgistop (Pharmigen, San Diego, Calif.) was added 6 hours before harvesting the cells from the culture. Cells were then washed once in FACSCAN buffer and stained with phycoerythrin (PE)-conjugated monoclonal rat anti-mouse CD8 or CD4 antibody (Pharmingen, San Diego, Calif.). Cells were subjected to intracellular cytokine staining using the Cytofix/Cytoperm kit according to the manufacturer's instructions (Pharmingen). FITC-conjugated anti-IFN-γ or anti-IL-4 antibodies and the immunoglobulin isotype control antibody (rat IgG1) were all purchased from Pharmingen. Analysis was done on a Becton-Dickenson FACScan with CELLQuest software (Becton Dickson Immunocytometry System, Mountain View, Calif.).

ELISA for Cytokines

Splenocytes ($4 \times 10^6$) were harvested 2 weeks after the last vaccination and cultured with 10 μg/ml E7 protein in a total volume of 2 ml of RPMI 1640, supplemented with 10% (vol/vol) fetal bovine serum, 50 units/ml penicillin/streptomycin, 2mM L-glutamine, 1mM sodium pyruvate, 2mM nonessential amino acids in a 24-well tissue culture plate for 72 hours. The supernatants were harvested and assayed for the presence of IFN-γ and IL-4 using ELISA kits (Endogen) according to-the manufacturer's protocol.

Anti-E7 ELISA

The anti-HPV 16 E7 antibodies in the sera were determined by a standard direct ELISA. A 96 microwell plate was coated with 100 μl 10 μg/ml bacteria-derived HPV-16 E7 proteins and incubated at 4° C. overnight. The wells were then blocked with PBS containing 20% fetal bovine serum. Sera were prepared from the mice on day 14 post-immunization, serially diluted in PBS, added to the ELISA wells, and incubated on 37° C. for 2 hr. After washing with PBS containing 0.05% Tween-20, the plate was incubated with 1/2000 dilution of a peroxidase-conjugated rabbit anti-mouse IgG antibody (Zymed, San Francisco, Calif.) at room temperature for one hour. The plate was washed 6 times, developed with TMB (Pierce, Rockford, Ill.), and stopped with 1M $H_2SO_4$. The ELISA plate was read with a standard ELISA reader at 450 nm.

Murine Tumor Cell Line

Murine tumor cell line TC-1 was grown and maintained using standard tissue culture methods. Growth of tumor cell lines and formation of tumors by transformed cells in mice is an art-recognized model of human cancer. HPV-16 E6, E7 and ras oncogene were used to transform primary C57BL/6 mice lung epithelial cells. The cells were grown in RPMI 1640, supplemented with 10% (vol/vol) fetal bovine serum, 50 units/ml penicillin/ streptomycin, 2mM L-glutamine, 1 mM sodium pyruvate, 2mM nonessential amino acids and 0.4 mg/ml G418 at 37° C. with 5% $CO_2$. On the day of tumor challenge, TC-1 cells were harvested by trypsinization, washed twice with 1X Hanks buffered salt solution and finally resuspended in 1X Hanks buffered salt solution to the designated concentration for injection.

Mice

Six to eight-week-old male C57BL/6 mice were purchased from the National Cancer Institute (Frederick, Md.).

In Vivo Tumor Protection

Mice (5 per group) were vaccinated via gene gun with 2 μg of HSP DNA, E7 DNA, E7-HSP70 DNA, or the empty plasmid without insert. One week later, the mice were boosted with the same regimen as the first vaccination. Another set of mice (5 per group) were vaccinated once (without further booster). One week after the last vaccination, mice were subcutaneously challenged with $5 \times 10^4$ cells/mouse TC-1 tumor cells in the right leg and then monitored twice a week.

In Vivo Tumor Treatment

The tumor cells and the DNA vaccines were prepared as described above. The mice were subcutaneously challenged with $2 \times 10^4$ cells/mouse TC-1 tumor cells in the right legs. Three days after challenge with TC-1 tumor cells, mice were given 2 μg of HSP DNA, E7 DNA, E7-HSP70 DNA, or the empty plasmid without insert via gene gun. One week later, these mice were boosted with the same regimen as the first vaccination. Another set of mice (5 per group) were vaccinated once without further booster after the tumor challenges. Mice were monitored twice a week.

In Vivo Antibody Depletion

In vivo antibody depletions were carried out using standard methods. C57BL/6 mice were vaccinated with 2 μg E7-HSP70 DNA via gene gun, boosted one week later, and challenged with $5 \times 10^4$ cells/mouse TC-1 tumor cells. Depletions were started one week prior to tumor challenge. A CD4-specific monoclonal antibody, e.g., MAb GK1.5, was used for CD4 depletion; a CD8-specific antibody e.g., MAb 2.43, was used for CD8 depletion, and an antibody which binds to NK cells, e.g., MAb PK136, was used for NK1.1 depletion. Flow cytometry analysis revealed that the greater than 95% of the appropriate lymphocytes subset were depleted with normal level of other subsets. Depletion was terminated on day 40 after tumor challenge.

Vaccination With E7-HSP70 Fusion DNA Enhances E7-Specific CD8⁺ T Cell-Mediated Immune Responses CD8⁺ T lymphocytes are one of the most crucial components among antitumor effectors. To determine the E7-specific CD8+ T cell precursor frequencies generated by E7-HSP70 DNA vaccines, enzyme-linked immunospot (ELISPOT) assays and intracellular cytokine stains were used. Both ELISPOT assay and intracellular cytokine staining are sensitive functional assays used to measure IFN-γ production at the single-cell level, which can thus be applied to quantify antigen-specific CD8⁺ T cells. As shown in FIG. 1A, 435 IFN-γ spot-forming CD8⁺ T cells specific for the immunodominant $D^b$-restricted E7(49–57; SEQ ID NO:5) peptide were detected per $10^6$ splenocytes derived from the E7-HSP70 DNA vaccinated mice, compared to only 14 E7(49–57)-specific IFN-γ spot-forming CD8⁺ T cells/$10^6$ splenocytes derived from the E7 DNA vaccinated mice. Subtracting the background produced by the pcDNA-3 vector alone (3 spots/$10^6$ splenocytes) yielded 11 and 432 E7(49–57)-specific IFN-γ spot-forming CD8+ T cells for the E7 and E7-HSP70 DNA vaccines, respectively. Similarly, the quantity of E7(49–57)-specific CD8⁺ T cell precursors can also be determined by flow cytometry analysis using double staining for CD8 and intracellular IFN-γ. Values from this assay (FIG. 1B) correlated closely with the ELISPOT results presented in FIG. 1A. As shown in FIG. 1B, mice vaccinated with E7-HSP70 DNA generated the highest number of E7-specific IFN-γ⁺ CD8⁺ T cell precursors (around 726/$10^6$ splenocytes) by flow cytometry analysis, whereas mice vaccinated with E7 DNA showed no signal above the vector-vaccinated controls. These data indicate that DNA encoding a MHC class I-restricted epitope of E7 operably linked to DNA encoding HSP70 or a fragment thereof led to at least a 30-fold increase in the E7-specific CD8⁺ T cell precursor frequencies.

Vaccination With E7-HSP70 Fusion DNA does not Enhance E7-Specific CD4⁺ T Cell-Mediated Immune Responses To determine E7-specific CD4⁺ T precursor cells and the cytokine profiles generated by E7-HSP70 DNA vaccines, double staining for CD4 surface marker and intracellular IFN-γ or IL-4 on splenocytes from immunized mice was carried out, followed by flow cytometry analysis. The splenocytes from immunized mice were cultured in vitro with E7 peptide (residues 30–67; SEQ ID NO:6) overnight and stained for both CD4 and intracellular IFN-γ. The E7 peptide (residues 30–67; SEQ ID NO:6) contains a major T helper epitope in the E7 open reading frame protein of HPV-16. The percentage of IFN-γ secreting CD4⁺ T cells was analyzed using flow cytometry. As shown in FIG. 2, mice vaccinated with E7-HSP70 DNA generated a similar number of CD4⁺ IFN-γ⁺ double positive cells compared to mice vaccinated with wild-type E7 DNA or vector alone. Mice vaccinated with E7 DNA mixed with HSP70 plasmid generated slightly higher CD4⁺ IFN-γ⁺ double positive cells, but there is no statistically significant difference in the CD4⁺ IFN-γ⁺ double positive cell numbers between each vaccinated group.

As a positive control for the ability of CD4 vs. intracellular IFN-γ staining to detect E7-specific CD4+ T cells, analysis of mice vaccinated with a DNA vaccine expressing Sig/E7/LAMP-1, which targets E7 to the MHC class II compartment, demonstrated a 3 fold increase in the CD4+ IFN-γ+ double positive cells relative to mice vaccinated with E7 DNA or control plasmid. IL-4 secreting E7-specific CD4+ T cell in mice vaccinated with various DNA vaccines were also analyzed. No significant CD4+ IL-4+ double-positive cells could be identified in the mice that received E7-HSP70 DNA, E7 DNA mixed with HSP70 DNA, wild type E7 DNA, empty plasmid DNA, or no vaccination. MICK-2 IL-4 secreting cells (Pharmingen, San Diego, Calif.) were used as positive controls to ensure the success of intracytoplasmic IL-4 staining for this study. These data indicate that the DNA vaccines of the invention which contain DNA encoding all or part of a heat shock protein induce a CD8+ immune response to the epitope encoded by the vaccine independent of a CD4+ immune response.

Vaccination With E7-HSP70 Fusion DNA dose not Generate E7-Specific Antibodies

The quantity of anti-HPV 16 E7 antibodies in the sera of the vaccinated mice was determined by a direct enzyme-linked immunoabsorbent assay (ELISA) 2 weeks after the last vaccination. No anti-E7 antibodies could be detected in the sera of mice of any vaccinated group (FIG. 3). The commercial anti-E7 monoclonal antibody (Zymed, San Francisco, Calif.) and sera from mice vaccinated with vaccinia virus containing the Sig/E7/LAMP-1 chimera were used as positive controls to ensure the success of anti-E7 ELISA for this study. This result is consistent with the complete absence of apparent E7-specific CD4 stimulation by either E7 DNA or E7-HSP70 DNA vaccines.

Vaccination with E7-HSP70 Fusion DNA Enhances Protection Against the Growth of Tumors To determine whether vaccination with the E7-HSP70 DNA construct protects mice against E7-expressing tumors, two in vivo tumor protection experiments were performed using different doses of DNA vaccines. For the first experiment, mice were vaccinated with 2 μg naked DNA/mouse via gene gun and boosted with the same dose one week later. For the second experiment, mice were vaccinated with 2 μg naked DNA/mouse via gene gun without further booster. The mice were then challenged with $5 \times 10^4$ TC-1/mouse subcutaneously in the right leg 7 days after the last vaccination. For the mice receiving vaccination with booster, 100% of those receiving E7-HSP70 DNA vaccination remained tumor-free 60 days after TC-1 challenge, while only 40% of mice receiving E7 DNA (in the absence of HSP-encoding DNA) vaccination remained tumor-free. In contrast, all of the unvaccinated mice and mice receiving empty plasmid or HSP DNA developed tumor growth within 15 days after tumor challenge (FIG. 4A). For the mice receiving vaccination once without booster, 100% of those receiving E7-HSP70 DNA vaccination remained tumor-free 60 days after TC-1 challenge, whereas all of the unvaccinated mice and mice receiving empty plasmid, HSP70 DNA or E7 DNA developed tumor growth within 15 days after tumor challenge (FIG. 4B). To determine whether the anti-tumor effect generated by E7-HSP70 DNA is long-lasting, these tumor free animals were rechallenged with the $5 \times 10^4$ TC-1 cells/mouse subcutaneously in the left leg. No tumor growth was observed up to 30 days after tumor rechallenge (FIGS. 4A–B).

In summary, these results indicated that a DNA construct encoding a MHC class I-restricted antigenic epitope operably linked to DNA encoding a HSP polypeptide, e.g. E7-HSP70 fusion DNA, significantly enhances the antitumor immunity against the growth of a tumor which express the class I-restricted epitope, e.g., TC-1 tumors. The antitumor effect was observed even when tested under more stringent conditions (no booster vaccine administered). The antitumor immunity generated by E7-HSP70 DNA construct was long lasting.

Therapeutic Vaccination With E7-HSP70 Fusion DNA Cures Mice With Established E7-Expressing Tumors To test the efficacy of DNA vaccines in eradicating established TC-1 tumors, in vivo tumor treatment experiments were performed using different doses of DNA vaccines. TC-1 cells were first injected into C57BL/6 mice subcutaneously at a dose of $2 \times 10^4$ cells per mouse in the right leg. Three days later, each mouse was treated with 2 μg of either control plasmid DNA, HSP70 DNA, wild type E7 DNA, or E7-HSP70 DNA intradermally via gene gun. For the first experiment, mice were boosted with the same vaccine dose 7 days after priming. For the second experiment, mice did not receive further booster after priming. As shown in FIG. 5A, for mice receiving boosted DNA vaccination, TC-1 tumor was eliminated from 80% of mice receiving the E7-HSP70 DNA vaccination, whereas all of the unvaccinated mice and mice receiving empty plasmid, HSP70 DNA or E7 DNA developed tumor growth within 20 days after tumor challenge. For the mice receiving vaccination once without booster, 60% of those receiving E7-HSP70 DNA vaccination remained tumor-free 70 days after TC-1 challenge, whereas all of the unvaccinated mice and mice receiving empty plasmid, HSP70 DNA, or E7 DNA developed tumor growth within 20 days after tumor challenge (FIG. 5B). In summary, these results showed that vaccination with wild-type E7 DNA (in the absence of DNA encoding an HSP polypeptide) failed to eradicate the previously-inoculated E7-expressing tumors in mice, while vaccination with DNA encoding E7 operably linked to DNA encoding an HSP polypeptide, e.g., E7-HSP70 DNA, eradicated the established E7-expressing tumors. These data indicated that E7-HSP70 DNA significantly enhanced antitumor immunity, and that the presence of DNA encoding an HSP polypeptide in a DNA vaccine construct enhances the antitumor immunity generated by the DNA vaccine compared to the level of immunity generated by a conventional DNA vaccine (i.e., one without DNA encoding an HSP polypeptide).

Fusion of DNA Encoding an Antigenic Epitope to HSP70-Encoding Sequences is Required for the Generation of Antitumor Immunity To determine whether fusion of E7 to HSP70 was required for antitumor immunity, E7-HSP70 DNA was compared to E7-DNA mixed with HSP70 DNA and the ability to generate the antitumor immunity measured. To ensure that both E7 DNA and HSP70 DNA was delivered into the same cell, the E7 DNA was mixed with HSP70 DNA before the bullet preparation. Thus, a single bullet would contain both E7 DNA and HSP70 DNA. Immunological assays and tumor protection experiments (without vaccination booster) were carried out as described above. The data indicated that only E7-HSP70 DNA enhanced the E7-specific CD8+ T cell-mediated immune responses. Mixing HSP70 DNA with E7

DNA did not enhance the CD8+ T cell-mediated immune responses. For the tumor protection experiment, all of the mice vaccinated with E7-HSP70 DNA remained tumor-free 60 days after tumor challenge. In contrast, all of the unvaccinated mice or mice vaccinated with E7 DNA mixed with HSP70 DNA developed tumor growth within 15 days after tumor challenge (FIG. 6). Fusion of E7 DNA to HSP70 DNA was essential for the generation of antitumor immunity. These results indicate that DNA encoding a MHC class I-restricted antigenic epitope must be operably linked to DNA encoding an APC-binding epitope and/or DNA encoding a cytoplasmic translocation polypeptide.

CD8+ T Cells but not CD4+ T Cells or NK Cells are Essential for the Antitumor Effect Generated by DNA Vaccine With E7 Fused to HSP70

To determine the subset of lymphocytes that are important for the rejection of E7-positive tumor cells, in vivo antibody depletion experiments were performed. The antibody depletion was started one week before the tumor challenge and terminated on day 40 after tumor challenge.

As shown in FIG. 7, all naive mice and all of the mice depleted of CD8+ T cells grew tumors within 14 days after tumor challenge. In contrast, all of the nondepleted mice and all of the mice depleted of CD4+ T cells or NK1.1 cells remained tumor-free 50 days after tumor challenge. These results indicate that DNA vaccine activated CD8+ T cells in a CD4-independent fashion, and that these CD8+ T cells are essential for the antitumor immunity generated by E7-HSP70 DNA vaccine.

The Role of HSP in Stimulating CD8+ T Cells

In the DNA vaccines of the invention, HSP70 chaperones the antigen to the appropriate cell type to optimize induction of CD8+ T cells. Ballistic DNA delivery introduces DNA directly into dermal precursors. The E7-HSP70 DNA-transfected DCs expressed HSP70. HSP70 is a cytosolic HSP which plays multiple roles in protein folding, transport, and degradation and is involved in processing MHC class I restricted antigens. HSP fusion products encoded by the DNA vaccines are targeted more efficiently for proteasomal processing.

CD8+ T cells are the key players in gene gun-mediated E7-HPS70 DNA vaccination. The data showed that CD8+ T cells are required in the effector phase of antitumor immunity. In contrast, depletion of CD4+ or NK1.1+ cells did not decrease the antitumor immunity generated by E7-HSP70 DNA. The finding is in contrast to approaches using protein-based HSP vaccines, which showed that CD4+ and CD8+ T cells and NK cells are required in the effector phases of antitumor immunity using gp96 preparations from tumor cells.

HSP complexes taken up by professional APC are involved in introducing HSP-associated peptides into the MHC-I antigen presentation pathway. Only activated B cells and mononuclear cells can take up HSP70, while activated T cells do not transport HSP70. Though the receptor-mediated uptake of HSP is important for HSP/peptide complex protein vaccines, it is unlikely to play a role in the gene gun-mediated E7-HSP70 DNA vaccines. According to the invention, the recombinant E7-HSP70 fusion gene encoded by the DNA vaccine was sent directly into DCs via gene gun, bypassing the need for receptor-mediated endocytosis. Cross-priming of APCs may also occur because E7-HSP70 might be released from other cell types, such as keratinocytes (which were also transfected by gene gun vaccination), and then enter the DCs via receptor-mediated endocytosis. The requirement of the fusion of E7 to HSP70 indicates that E7 becomes more immunogenic because of the addition of HSP70 T cell epitopes. Vaccination with HSP70 DNA expands the pool of HSP70-reactive T cells which may exist in an individual (due to prior exposure to pathogens). These HSP70-reactive T cells exert a strong helper effect reacting to conjugated peptides which led to an increase in the E7-specific CD8+ T cell precursor frequency detected by ELISPOT assay and by intracellular cytokine staining observed in the mice vaccinated with E7-HSP70 fusion gene, but not in the mice vaccinated with E7 plasmid mixed with HSP70 plasmid.

HSPs may directly activate T cells in vivo and in vitro via an antigen-independent mechanism. In the absence of antigenic peptides, HSP can induce the secretion of TNF-α and IFN-γ of the antigen-specific CTL clones. Human HSP-60 can act as a danger signal to the innate immune system and can induce a T helper 1 proinflammatory response. However, a significant increase in the numbers of E7-specific CD4+ T cells was not observed in mice vaccinated with HSP70 DNA alone or E7 plasmid mixed with HSP70 plasmids. γδ T cells stimulated by the HSP component of the DNA vaccine may also participate in the antitumor effect generated by E7-HSP70 DNA vaccines.

While E7-HSP70 generates potent CD8+ T cell responses through enhanced MHC class I presentation, other constructs that target antigen to MHC class II presentation pathways may provide enhanced CD4+ T cell responses. Administration of vaccines that directly enhance MHC class I and class II restricted pathways may be coadministered. For example, a DNA construct in which the second DNA encodes a LAMP-1 endosomal/lysosomal targeting signal for enhancing the MHC class II presentation pathway of E7, e.g., chimeric Sig/E7/LAMP-1 DNA vaccine is coadministered to stimulate antigen-specific CD4+ T cells. The E7-HSP70 vaccine described herein in conjunction with a MHC class II-targeting vaccine such as Sig/E7/LAMP-1 activate multiple arms of the immune system in a synergistic fashion, leading to significantly enhanced CD4+ and CD8+ T cell responses and potent antitumor effects.

These results indicate an example of the immunogenic composition of the invention such as a DNA fusion construct encoding HSP70 and HPV-16 E7 gene can generate stronger E7-specific CD8+ T cell-mediated immune responses and antitumor effects against HPV-16 E7-expressing murine tumors generated by DNA vaccines encoding the antigen, e.g, E7, alone. These data therefore demonstrate that fusion of HSP70 sequences to an antigen gene (or fragment thereof) greatly enhances the potency of DNA vaccines. This strategy is applicable to infectious disease and to other cancer systems with known tumor-specific antigens.

EXAMPLE 2

Enhancement of DNA Vaccine Potency by Linkage of DNA Sequence Encoding GM-CSF and Translocation Domain of a Pseudomonas Exotoxin A to an Antigen Gene An immunogenic composition containing DNA encoding GM-CSF (or a fragment thereof) operably linked to an antigen-encoding sequence enhances targeting of the antigen to cells expressing GM-CSF receptors, such as professional APCs and their precursors. The presence of DNA encoding an ETA polypeptide, e.g, domain II of pseudomonas exotoxin A (ETA(dII)) mediates translocation of the antigen from endosomal/lysosomal compartments to the cytoplasm to enhance MHC class I presentation. A DNA chimera (GM-ETA(dII)-E7) was made by fusing DNA sequences encoding GM-CSF and ETA(dII) to the gene of a model antigen, E7. An art-recognized mouse model of human cancer was used to evaluated the immunogenicity and anti-tumor activity elicited by the construct. Immunization of mice using the GM-ETA(dII)-E7 chimera DNA vaccine enhanced E7-specific CD8+ and CD4+ T cell immune responses and effective anti-tumor protection and treatment against an E7-expressing murine tumor cell line (TC-1) through intramuscular or intradermal injection. This dramatic anti-tumor effect was not observed in DNA vaccines encoding other constructs, particularly GM-E7, ETA(dII)-E7, or GM-ETA(dII). The DNA vaccination strategy described herein is usefule for antigen specific immunotherapy for cancers and infection by pathogenic microorganisms.

Improvement of MHC Class I Presentation of Exogenous Antigen is a Strategy for Enhancing DNA Vaccine Potency That may be Tested Using Domain II of Pseudomonas Exotoxin A (ETA(dII))

ETA is a toxin derived from the bacterium *Pseudomonas aeruginosa* that blocks protein synthesis. ETA(dII) allow translocation from endosomal/lysosomal compartments to the cytoplasm, which leads to enhancement of MHC class I presentation of exogenous antigen. Since domain I is responsible for LDL-binding and domain III has the toxic capability of binding with ADP-ribosyl transferase, these unwanted portions of ETA are replaced or deleted. The data described below was generated using the DNA chimera (GM-ETA(dII)-E7). HPV-16 E7 was used as the model antigen because it is a clinically relevant an oncogenic protein that is widely expressed and well-characterized in HPV-associated malignancies. GM-CSF DNA can be incorporated into various APCs, inducing enhancement of DC maturation. By linkage with antigen, GM-CSF may also enhance targeting of the antigen to in cells expressing GM-CSFR, such as professional APCs and their precursors. ETA(dII) linked with antigen in a DNA form may be able to translocate antigen from the endosomal/lysosomal compartment to the cytoplasm, leading to enhanced MHC class I presentation. Vaccination with a chimeric DNA construct designed according to the GM-ETA(dII)-E7 example provide the necessary potency for activation of both MHC class I and II-restricted pathways, leading to enhanced E7-specific immune responses and anti-tumor effects.

The following materials and methods were used to generate the data described below.

Plasmid DNA Constructs and Preparation

DNA fragment encoding murine GM-CSF was obtained by PCR with 5' end primer , 5'-GGGGAGATCTGGATGTGGCTGCAGAATTTA-3' (SEQ ID NO:11) and 3'end primer (EcoRI), 5'-GGGAGAATTCTTTTGGACTGGTTTTTTGCAT-3' (SEQ ID NO:12). cDNA generated from GM-CSF-transduced B-16 melanoma cell was used as temple for PCR.

TABLE 5

Amino acid sequence of Mouse GM-CSF

MWLQNLLFLGIVVYSLSAPTRSPITVTRPWKHVEAIKEALNLLD
DMPVTLNEEVEVVSNEFSFKKLTCVQTRLKIFEQGLRGNFTKLKGALNMTASYYQTYC
PPTPETDCETQVTTYADFIDSLKTFLTDIPFECKKPVQK (SEQ ID NO: 1;
GENBANK Accession No. X02333)

TABLE 6 cDNA sequence of Mouse GM-CSF

| | | | | |
|---|---|---|---|---|
| gagctcagca agcgctctcc cccaattcca ttagccaaag tggacgccac cgaacagaca | 61 |
| gacctaggct aagaggtttg atgtctctgg ctacccgact ttgaaaattt tccgcaaagg | 121 |
| aaggcctttt gactacaatg gcccacgaga gaaaggctaa ggtcctgagg aggatgtggc | 181 |
| tgcagaattt acttttcctg ggcattgtgg tctacagcct ctcagcaccc acccgctcac | 241 |
| ccatcactgt cacccggcct tggaagcatg tagaggccat caaagaagcc ctgaacctcc | 301 |
| tggatgacat gcctgtcaca ttgaatgaag aggtagaagt cgtctctaac gagttctcct | 361 |
| tcaagaagct aacatgtgtg cagacccgcc tgaagatatt cgagcagggt ctacgggca | 421 |
| atttcaccaa actcaagggc gccttgaaca tgacagccag ctactaccag acatactgcc | 481 |
| cccaactcc ggaaacggac tgtgaaacac aagttaccac ctatgcggat ttcatagaca | 541 |
| gccttaaaac ctttctgact gatatcccct ttgaatgcaa aaaaccagtc caaaaatgag | 601 |
| gaagcccagg ccagctctga atccagcttc tcagactgct gcttttgtgc ctgcgtaatg | 661 |
| agccaggaac tcggaatttc tgccttaaag ggaccaagag atgtggcaca gccacagttg | 721 |
| gagggcagta tagccctctg aaaacgctga ctcagcttgg acagcggcaa gacaaacgag | 781 |
| agatattttc tactgatagg gaccattata tttatttata tatttatatt ttttaaatat | 841 |
| ttatttattt atttatttaa ttttgcaact ctatttattg agaatgtctt accagataat | 901 |
| aaattattaa aacttt (SEQ ID NO:2; GENBANK Accession No. X05906; "atg" start site underlined) | |

The amplified products were subsequently cloned into BglII and EcoRI sites of pSP73 vector (Promega) to generate pSP73-GM. The same strategy is employed to make a DNA construct using human GM-CSF sequences (GENBANK Accession M11220). Alteratively, the first DNA encodes all or an APC-binding fragment of FL, CTLA-4, 4-1BB, CD40 ligand, or TNF receptor. The amino acid sequences and nucleotide sequences of these proteins are readily available to those skilled in the art. Determining whether a give polypeptide or protein fragment binds to an antigen presenting cell (e.g., a macrophage or DC) is also well known in the art. For example, the polypeptide (as well as a control polypeptide known not to bind to an APC) is labelled with a detectable marker and incubated with an APC. After the cells are washed, detection of the label on or in APC's (compared to the control) indicates that the polypeptide has an APC binding domain or sequence.

The DNA fragment containing the domain II of ETA was generated using PCR with 5' end primer, 5'-GGGAGAATTCTCGCCTGTCACTTTCCCGAG-3' (SEQ ID NO:13) and 3' end primer, 5'-GGAAGGATCCAGTTCTGCGTGCCGCGGG-3' (SEQ ID NO:14).

TABLE 7

| Amino acid sequence of ETA |
|---|
| MHLIPHWIPLVASLGLLAGGSSASA AEEAFDLWNECAKACVLDL |
| KDGVRSSRMSVDPAIADTNGQGVLHYSMVLEGGNDALKLAIDNALSITSDGLTIRLEG |
| GVEPNKPVRYSYTRQARGSWSLNWLVPIGHEKPSNIKVFIHELNAGNQLSHMSPIYTI |
| EMGDELLAKLARDATFFVRAHESNEMQPTLAISHAGVSVVMAQTQPRREKRWSEWASG |
| KVLCLLDPLDGVYNYLAQQRCNLDDTWEGKIYRVLAGNPAKHDLDIKPTVISHRLHFP |
| EGGSLAALTAHQACHLPLETFTRHRQPRGWEQLEQCGYPVQRLVALYLAARLSWNQVD |
| QVIRNALASPGSGGDLGEAIREQPEQARLALTLAAAESERFVRQGTGNDEAGAANADV |
| VSLTCPVAAGECAGPADSGDALLERNYPTGAEFLGDGGDVSFSTRGTQNWTVERLLQA |
| HRQLEERGYVFVGYHGTFLEAAQSIVFGGVRARSQDLDAIWRGFYIAGDPALAYGYAQ |
| DQEPDARGRIRNGALLRVYVPRSSLPGFYRTSLTLAAPEAAGEVERLIGHPLPLRLDA |
| ITGPEEEGGRLETILGWPLAERTVVIPSAIPTDPRNVGGDLDPSSIPDKEQAISALPD |
| YASQPGKPPREDLK (SEQ ID NO:3; GENBANK Accession No. K01397 M23348; residues 1–25 = signal peptide; start of mature peptide underlined "A"; translocation domain spans residues 247–417) |

TABLE 8

| cDNA encoding ETA | |
|---|---|
| ctgcagctgg tcaggccgtt tccgcaacgc ttgaagtcct ggccgatata ccggcagggc | 61 |
| cagccatcgt tcgacgaata aagccacctc agccatgatg ccctttccat ccccagcgga | 121 |
| accccgacat ggacgccaaa gccctgctcc tcggcagcct ctgcctggcc gccccattcg | 181 |
| ccgacgcggc gacgctcgac aatgctctct ccgcctgcct cgccgcccgg ctcggtgcac | 241 |
| cgcacacggc ggagggccag ttgcacctgc cactcaccct tgaggcccgg cgctccaccg | 301 |
| gcgaatgcgg ctgtacctcg gcgctggtgc gatatcggct gctggccagg ggcgccagcg | 361 |
| ccgacagcct cgtgcttcaa gagggctgct cgatagtcgc caggacacgc cgcgcacgct | 421 |
| gaccctggcg gcggacgccg gcttggcgag cggccgcgaa ctggtcgtca ccctgggttg | 481 |
| tcaggcgcct gactgacagg ccgggctgcc accaccaggc cgagatggac gccctgcatg | 541 |
| tatcctccga tcggcaagcc tcccgttcgc acattcacca ctctgcaatc cagttcataa | 601 |
| atcccataaa agccctcttc cgctccccgc cagcctcccc gcatcccgca ccctagacgc | 661 |
| cccgccgctc tccgccggct cgcccgacaa gaaaaaccaa ccgctcgatc agcctcatcc | 721 |
| ttcacccatc acaggagcca tcgcgatgca cctgataccc cattggatcc ccctggtcgc | 781 |
| cagcctcggc ctgctcgccg gcggctcgtc cgcgtccgcc gccgaggaag ccttcgacct | 841 |
| ctggaacgaa tgcgccaaag cctgcgtgct cgacctcaag gacggcgtgc gttccagccg | 901 |
| catgagcgtc gacccggcca tcgccgacac caacggccag ggcgtgctgc actactccat | 961 |
| ggtcctggag ggcggcaacg acgcgctcaa gctggccatc gacaacgccc tcagcatcac | 1021 |
| cagcgacggc ctgaccatcc gcctcgaagg cggcgtcgag ccgaacaagc cggtgcgcta | 1081 |
| cagctacacg cgccaggcgc gcggcagttg gtcgctgaac tggctggtac cgatcggcca | 1141 |
| cgagaagccc tcgaacatca aggtgttcat ccacgaactg aacgccggca accagctcag | 1201 |
| ccacatgtcg ccgatctaca ccatcgagat gggcgacgag ttgctggcga agctggcgcg | 1261 |
| cgatgccacc ttcttcgtca gggcgcacga gagcaacgag atgcagccga cgctcgccat | 1321 |
| cagccatgcc ggggtcagcg tggtcatggc ccagacccag ccgcgccggg aaaagcgctg | 1381 |
| gagcgaatgg gccagcggca aggtgttgtg cctgctcgac ccgctggacg gggtctacaa | 1441 |
| ctacctcgcc cagcaacgct gcaacctcga cgatacctgg gaaggcaaga tctaccgggt | 1501 |
| gctcgccggc aacccggcga agcatgacct ggacatcaaa cccacggtca tcagtcatcg | 1561 |
| cctgcacttt cccgagggcg gcagcctggc cgcgctgacc gcgcaccagg cttgccacct | 1621 |
| gccgctggag actttcaccc gtcatcgcca gccgcgcggc tgggaacaac tggagcagtg | 1681 |
| cggctatccg gtgcagcggc tggtcgccct ctacctggcg gcgcggctgt cgtggaacca | 1741 |
| ggtcgaccag gtgatccgca acgccctggc cagccccggc agcggcggcg acctgggcga | 1801 |
| agcgatccgc gagcagccgg agcaggcccg tctggccctg accctggccg ccgccgagag | 1861 |
| cgagcgcttc gtccggcagg gcaccggcaa cgacgaggcc ggcgcggcca acgccgacgt | 1921 |
| ggtgagcctg acctgcccgg tcgccgccgg tgaatgcgcg ggcccggcgg acagcggcga | 1981 |
| cgccctgctg gagcgcaact atcccactgg cgcggagttc ctcggcgacg gcggcgacgt | 2041 |
| cagcttcagc acccgcggca cgcagaactg gacggtggag cggctgctcc aggcgcaccg | 2101 |
| ccaactggag gagcgcggct atgtgttcgt cggctaccac ggcaccttcc tcgaagcggc | 2161 |
| gcaaagcatc gtcttcggcg gggtgcgcgc gcgcagccag gacctcgacg cgatctggcg | 2221 |
| cggtttctat atcgccggcg atccggcgct ggcctacggc tacgcccagg accaggaacc | 2281 |
| cgacgcacgc ggccggatcc gcaacggtgc cctgctgcgg gtctatgtgc cgcgctcgag | 2341 |
| cctgccgggc ttctaccgca ccagcctgac cctggccgcg ccggaggcgg cgggcgaggt | 2401 |
| cgaacggctg atcggccatc cgctgccgct gcgcctggac gccatcaccg gccccgagga | 2461 |
| ggaaggcggg cgcctggaga ccattctcgg ctggccgctg gccgagcgca ccgtggtgat | 2521 |
| tccctcggcg atccccaccg acccgcgcaa cgtcggcggc gacctcgacc cgtccagcat | 2581 |
| ccccgacaag gaacaggcga tcagcgccct gccggactac gccagccagc ccggcaaacc | 2641 |

TABLE 8-continued cDNA encoding ETA

```
gccgcgcgag gacctgaagt aactgccgcg accggccggc tcccttcgca ggagccggcc   2701
ttctcggggc ctggccatac atcaggtttt cctgatgcca gcccaatcga atatgaattc
(SEQ ID NO:4; GENBANK Accession No. K01397 M23348)
```

The amplified products were subsequently cloned into EcoRI and BamHI sites of pSP73-GM to generate pSP73-GM-ETA(dII). The DNA fragment containing HPV-16 E7 was synthesized by PCR with 5' end primer, 5'-GGGAGGATCCTCATGCATGGAGATACACCT-3' (SEQ ID NO:15) and 3' end primer, 5'-GGGGAAGCTTATCCTGAGAACAGATGGGG-3' (SEQ ID NO:16). The plasmid pCMVneoBamHI-E7 was used as temple for the PCR reaction. The amplified products were further cloned into BamHI and HindIII sites of pSP73-GM-ETA(dII) to generate pSP73-GM-ETA(dII)-E7. The sequence of GM-ETA(dII)-E7 was confirmed by DNA sequencing. The pcDNA3.1-GM-ETA(dII)-E7 was obtained by digesting pSP73-GM-ETA(dII)-E7 with BglII and HindII restriction enzymes and cloned the isolated GM-ETA(dII)-E7 fragment into the unique BamHI and HindIII cloning sites of the pcDNA3.1(-) expression vector (Invitrogen, Carlsbad, Calif.) downstream of the cytomegalovirus promoter. The pcDNA3.1-GM-ETA(dII) was generated by digesting pSP73-GM-ETA(dII)-E7 with BglII and BamHI restriction enzymes and cloned the isolated GM-ETA(dII) fragment into the unique BamHI cloning site of the pcDNA3.1(-). The pcDNA3.1-ETA(dII)-E7 was obtained by digesting pSP73-GM-ETA(dII)-E7 with EcoRI and HindIII restriction enzymes and cloned the isolated ETA(dII)-E7 fragment into the unique EcoRI and HindIII cloning sites of the pcDNA3.1(-). The pcDNA3.1-GM was generated by digesting pSP73-GM-ETA(dII)-E7 with BglII and BamHI restriction enzymes and cloned the isolated murine GM-CSF fragment into the unique BamHI cloning site of the pcDNA3.1(-). The pcDNA3.1-ETA(dII) was obtained by digesting pSP73-GM-ETA(dII)-E7 with EcoRI and BamHI restriction enzymes and cloned the isolated ETA(dII) fragment into the unique EcoRI and BamHI cloning sites of the pcDNA3.1(-). The pcDNA3.1-E7 was generated by digesting pSP73-GM-ETA(dII)-E7 with BamHI and HindIII restriction enzymes and cloned the isolated E7 fragment into the unique BamHI and HindIII cloning sites of the pcDNA3.1(-). For the generation of pcDNA3.1-GM-E7, The E7 fragment was synthesized by PCR with a 5' end primer, 5'-CCCAGATCTAATCATGCATG -3' (SEQ ID NO:17) and 3' end primer, 5'-GGGGAAGCTTATCCTGAGAACAGATGGGG-3' (SEQ ID NO:18). The amplified E7 products were digested with BglII and HindIII and further cloned into BamHI and HindIII sites of pSP73-GM. The GM-E7 fragment was isolated from pSP73-GM-E7 by digestion with BglII and HindIII and cloned into the unique BamHI and HindII sites of pcDNA3.1(-).

The accuracy of these constructs was confirmed by DNA sequencing. Plasmid DNA with GM, ETA(dII), E7, GM-ETA(dII), ETA(DII)-E7, GM-E7 or GM-ETA(DII)-E7 gene insert and the "empty" plasmid vector were transfected into subcloning efficient DH5(TM cells (Life Technologies, USA). The DNA was then amplified and purified using double CsCl purification (BioServe Biotechnologies, Laurel, Md.). The integrity of plasmid DNA and the absence of *Escherichia coli* DNA or RNA were checked in each preparation using 1% agarose gel electrophoresis. DNA concentration was determined by the optical density measured at 260 nm. The presence of the inserted E7 fragment was confirmed by restriction enzyme digestion and gel electrophoresis.

DNA Vaccination

Gene gun particle-mediated DNA vaccination was performed using a helium-driven gene gun (Bio-rad, Hercules, Calif.) according to standard protocols and as described above.

Intracytoplasmic Cytokine Staining and Flow Cytometry

Splenocytes from naive or vaccinated groups of mice were incubated either with the E7 peptide (residues 49–57; SEQ ID NO:5) that contains MHC class I epitope or the E7 peptide (residues 30–67) that contains MHC class II peptide. The E7 peptide was added at a concentration of 2 µg/ml for 20 hours. To detect E7-specific $CD8^+$ T cell precursors and E7-specific $CD4^+$ T helper cell responses, $CD8^+$ CTL epitopes residues 49–57 and residues 30–67 were used, respectively. Golgistop (Pharmigen, San Diego, Calif.) was added 6 hours before harvesting the cells from the culture. Cells were then washed once in FACSCAN buffer and stained with phycoerythrin (PE)-conjugated monoclonal rat anti-mouse CD8 or CD4 antibody (Pharmingen, San Diego, Calif.). Cells were subjected to intracellular cytokine staining using the Cytofix/Cytoperm kit according to the manufacturer's instructions (Pharmingen). FITC-conjugated anti-IFN-γ or anti-IL-4 antibodies and the immunoglobulin isotype control antibody (rat IgG1) were all purchased from Pharmingen. Analysis was done on a Becton-Dickenson FACScan with CELLQuest software (Becton Dickson Immunocytometry System, Mountain View, Calif.).

Mice and Murine Tumor Cells

Mice and the production and maintenance of tumor cells such as TC-1 cells is described above in Example 1.

In Vivo Tumor Protection

For the tumor protection experiment, mice (5 per group) were vaccinated via gene gun with 2 µg of plasmid DNA with GM, ETA(dII), E7, GM-ETA(dII), ETA(DII)-E7, GM-E7 or GM-ETA(DII)-E7 gene insert and the "empty" plasmid vector. One week later, the mice were boosted with the same regimen as the first vaccination. Another set of mice (5 per group) were vaccinated once (without further booster). One week after the last vaccination, mice were subcutaneously challenged with $5 \times 10^4$ cells/mouse TC-1 tumor cells in the right leg and then monitored twice a week.

In Vivo Antibody Depletion

Methods for in vivo antibody depletions are described above. Briefly, C57BL/6 mice were vaccinated with 2 µg GM-ETADII-E7 DNA via gene gun, boosted one week later, and challenged with 5×10⁴ cells/mouse TC-1 tumor cells. Depletions were started one week prior to tumor challenge. MAb GK1.5 was used for CD4 depletion, MAb 2.43 was used for CD8 depletion, and MAb PK136 was used for NK1.1 depletion. Flow cytometry analysis revealed that the greater than 95% of the appropriate lymphocytes. subset were depleted with normal level of other subsets. Depletion was terminated on day 40 after tumor challenge.

Generation and Characterization of GM-ETA(dII)-E7 Fusion DNA Vaccine

A schematic diagram showing constructs of GM-ETA (dII)-E7, GM-ETA(dII), ETA(dII)-E7, GM-E7, GM-CSF, ETA(dII), and E7 is demonstrated in FIG. 8.

Vaccination With GM-ETA(dII)-E7 Fusion DNA Enhances E7-Specific CD8⁺ T Cell-Mediated Immune Responses CD8⁺ T lymphocytes are one of the most crucial components among antitumor effectors. To determine the E7-specific CD8⁺ T cell precursor frequencies generated by GM-ETA(DII)-E7 DNA vaccines, intracellular cytokine stains were used. The quantity of E7(49–57)-specific CD8+ T cell precursors was determined by flow cytometry analysis using double staining for CD8 and intracellular IFN-γ. Values from this assay correlated closely with the ELISPOT results presented. As shown in FIG. 9, mice vaccinated with GM-ETA(dII)-E7 DNA generated the highest number of E7-specific IFN-γ⁺ CD8⁺ T cell precursors by flow cytometry analysis, whereas mice vaccinated with E7, GM-CSF, ETA (dII), GM-ETA(dII), GM-E7, or ETA-E7 DNA showed no signal above the vector-vaccinated controls.

Vaccination With GM-ETA(dII)-E7 Fusion DNA Also Enhances E7-Specific CD4⁺ T Cell-Mediated Immune Responses To determine E7-specific CD4⁺ T precursor cells and the cytokine profiles generated by GM-ETA(dII)-E7 DNA vaccines, double staining was performed for CD4 surface marker and intracellular IFN-γ on splenocytes from immunized mice, followed by flow cytometry analysis. The splenocytes from immunized mice were cultured in vitro with E7 peptide (residues 30–67 of SEQ ID NO:7) overnight and stained for both CD4 and intracellular IFN-γ. The E7 peptide (residues 30–67 of SEQ ID NO:7) contains a major T helper epitope in the E7 open reading frame protein of HPV-16. Methods for determining T helper cell epitopes within the polypeptide sequence of a protein or peptide are well known in the art.

The percentage of IFN-γ secreting CD4⁺ T cells was analyzed using flow cytometry. As shown in FIG. 10, mice vaccinated with GM-ETA(dII)-E7 DNA generated the greater number of CD4⁺ IFN-γ⁺ double positive cells compared to mice vaccinated with E7 DNA, GM-CSF, ETA (dII), GM-ETA(dII), ETA-E7 DNA or vector alone. Mice vaccinated with GM-ETA(dII)-E7 DNA generated similar level of E7-specific CD4⁺ IFN-γ⁺ double positive cells. These results indicate GM-CSF plays an important role in enhancing IFN-γ secreting E7-specific CD4⁺ T cell in vaccinated mice and that DNA vaccines containing GM-CSF-coding sequence operably linked to DNA encoding a target antigen are more potent than those which contain antigen-encoding sequences alone.

Vaccination With GM-ETA(dII)-E7 Fusion DNA Enhances Protection of Mice Against the Growth of TC-1 Tumors To determine whether vaccination with the GM-ETA (DII)-E7 DNA construct protects mice against E7-expressing tumors, in vivo tumor protection experiments were performed using various DNA vaccines. Mice were vaccinated with 2 μg naked DNA/mouse via gene gun and boosted with the same dose one week later. The mice were then challenged with 5×10⁴ TC-1/mouse subcutaneously in the right leg 7 days after the last vaccination. 100% of those mice receiving GM-ETA(DII)-E7 DNA vaccination remained tumor-free 30 days after TC-1 challenge, while all of the unvaccinated mice and mice receiving E7, GM-CSF, ETA (dII), GM-ETA(dII), GM-E7, ETA-E7 DNA or empty plasmid developed tumor growth within 15 days after tumor challenge (FIG. 11). To determine whether the antitumor effect generated by GM-EETA(DII)-E7 DNA is long-lasting, these tumor free animals were rechallenged with the 5×10⁴ TC-1 cells/mouse subcutaneously in the left leg. No tumor growth was observed up to 30 days after tumor rechallenge. These results indicated that GM-ETA(DII)-E7 fusion DNA significantly enhances the antitumor immunity against the growth of TC-1 tumors and that the antitumor immunity generated by GM-ETA(DII)-E7 DNA is long lasting.

CD8⁺ T Cells are Essential for the Antitumor Effect Generated by GM-ETA(dII)-E7 DNA Vaccine To determine the subset of lymphocytes that are important for the rejection of E7-positive tumor cells, in vivo antibody depletion experiments were carried out. The antibody depletion was started one week before the tumor challenge and terminated on the day indicated in FIG. 12 after tumor challenge. As shown in FIG. 12, all naive mice and all of the mice depleted of CD8⁺ T cells grew tumors within 14 days after tumor challenge. In contrast, all of the nondepleted mice and all of the mice depleted of CD4+ T cells or NK1.1 cells remained tumor-free X days after tumor challenge. These results indicate that CD8⁺ T cells are essential for the antitumor immunity generated by GM-ETAdII-E7 DNA vaccine.

The data described herein demonstrate that a chimeric DNA construct encoding a chimeric polypeptide with an APC-binding domain, a cytoplasmic translocation domain, and an antigenic epitope, induces a potent immune response specific for the encoded antigenic epitope. In a mouse tumor, the results showed that fusion of the GM-CSF gene, the ETA(dII) gene, and the HPV-16 E7 gene in a chimera generates enhanced E7-specific CD8+ and CD4+ T cell-mediated immune responses and antitumor effects against HPV-16 E7-expressing murine tumors.

Immunization of mice using the GM-ETA(dII)-E7 chimera was capable of mediating E7-specific immune responses and effective anti-tumor protection and treatment against an E7-expressing murine tumor cell line (TC-1) through intramuscular or intradermal injection. This dramatic anti-tumor effect was not observed in DNA vaccines encoding other constructs, particularly GM-E7, ETA(dII)-E7, or GM-ETA(dII). Furthermore, greater CD8+ and CD4+ T cell responses were observed in mice receiving GM-ETA (dII)-E7 than in mice receiving other constructs. These results indicated that the GM-ETA(dII)-E7 chimeric DNA represents a novel strategy for cancer immunotherapy and that the components of the vaccine are important in the generation of potent E7-specific immune responses and anti-tumor effects.

The results indicated that the GM-CSF gene was an important component in GM-ETA(dII)-E7, demonstrated by the comparison of GM-ETA(dII)-E7 and ETA(dII)-E7 DNA constructs. The ETA(dII)-E7 construct lacked the GM-CSF component of GM-ETA(dII)-E7, which may account for the lack of enhanced E7-specific CD8+ or CD4+ T cell-mediated immune responses and anti-tumor effects. GM-CSF induces production of granulocytes and APCs and acts as an immunostimulatory signal to DCs. Furthermore, GM-CSF targets professional APCs and promote their differentiation since they possess the GM-CSF receptor. GM-ETA(dII)-E7 induces changes in MHC and co-stimulatory molecule expression on DCs and other APCs due to the production of GM-CSF, resulting in enhanced humoral and cell-mediated immune responses that were not observed in ETA(dII)-E7. These observations indicated that the immune-enhancing effect of GM-CSF on dendritic cells is a crucial component to the generation of immune responses and an anti-tumor effect by GM-ETA(dII)-E7.

The antigen-specific immunotherapy approach of the invention targets the surface molecules of DCs, which allows antigen to be directed into DCs for processing and presentation. Other polypeptides which can be used as the APC-binding component of the immunogenic composition include Flt-3 ligand, CD40 ligand, TNFα, and 41BB. DNAs encoding such polypeptides are useful as the first DNA component of the immunogenic composition or DNA vaccine of the invention. Flt3 ligand (Flt3-1 or FL) augments the function and quantity of dendritic cells in vivo. Flt3 (fms-like tyrosine kinase 3) is a murine tyrosine kinase receptor known in the art, and Flt3 has been used to identified and subsequently clone the corresponding ligand, Flt3-L (Hannum et al., 1994, Nature. 368: 643–8; Maraskovsky et al., Journal of Experimental Medicine, 1996 184: 1953–62, 199638). CD40 ligand (CD154) is also useful to enhance vaccine potency because of its effect on DCs. TNF-α represents another strategy for enhancing vaccine potency; TNF-α promotes the migration of DCs to lymphoid tissues and differentiation and development of Langerhans cells. Another strategy for enhancing vaccine potency is the use of 4-1BBL, a cytokine of the tumor necrosis factor family that binds to 4-1BB (CD137). 4-1BBL expression on DCs followed by interaction with 4-1BB provides secondary costimulatory signals to T cells for initiating proliferation, independent of signaling through the CD28 receptor. These strategies for enhancing vaccine potency employ DC surface molecules in a manner similar to GM-CSF in GM-ETA(dII)-E7, allowing for targeting of antigen to DCs and consequent induction of DC differentiation and enhancement of antigen processing and presentation.

Diphtheria, clostridal (botulinum, tetanus), anthrax, yersinia, cholera, and *Bordetella pertussis* toxins represent bacteria-derived molecules that may have therapeutic applications. Such molecules function in a manner similar to the manner in which ETA was applied to DNA vaccines for enhancement of MHC class I presentation through translocation of antigen from the endosomal/lysosomal compartment to the cytosol if the toxic domain of the gene encoding the toxin is mutated or deleted. Determining whether a give polypeptide or protein fragment has cytoplasmic translocation activity is determined as follows. Anthrax toxin lethal factor (LF) has been shown to translocate foreign proteins into the cytosol of eukaryotic cells), resembling the mechanism of diphtheria toxin. *Yersiniae cytotoxins* YopE and YopH are useful as. translocation domains and for internalization of antigens across the host cell membrane into the cytosol of macrophages. *Bordetella pertussis* adenylate toxin (CyaA) translocates directly through the cell membrane to the cytosol, thus enhancing MHC class I antigen handling. These strategies for enhancing vaccine potency employ the translocation domains of bacterial toxins in a manner similar to ETA(dII) in GM-ETA(dII)-E7, allowing antigen escape from the endosomal/lysosomal compartments to the cytosol and consequent enhancement of MHC class I presentation.

EXAMPLE 3

Enhancement of DNA Vaccine Potency by Linkage of DNA Encoding the Translocation Domain of Pseudomonas Exotoxin A to an Antigen Gene (ETA(dII)) is capable releasing protein for uptake by other cells. A DNA vaccine administered intradermally via gene gun encoding ETA fused with the HPV-16 E7 antigen leads to the distribution of E7 to a greater number of antigen presenting cells than a vaccine without ETA-encoding sequences. Immunological assays revealed that vaccination with E7 fused to ETA(dII) led to a 30-fold increase in E7-specific CD8+ T cell precursor frequencies with no significant E7-specific CD4 or antibody enhancement. In vitro studies indicated that cells transfected with ETA(dII)-E7 DNA presented E7 antigen through the MHC class I pathway in a more efficient manner than cells transfected with wild-type E7 DNA. Furthermore, bone marrow-derived dendritic cells pulsed with ETA fusion protein presented E7 antigen through the MHC class I pathway in a more efficient manner than dendritic cells pulsed with wild-type E7 protein. The surprising enhancement of CD8+ T cell-mediated immunity led to potent subcutaneous tumor protection and treatment of lung metastases. These data provide the basis for strategies to enhance antigen-specific DNA vaccine potency by increasing the spread of expressed antigen, e.g., by administering DNA vaccines encoding ETA-antigen fusion proteins or chimeras.

EXAMPLE 4

Enhancement of DNA Vaccine Potency By Linkage of Antigen-encoding Sequences to a FL-encoding Sequences Flt3-ligand is an important cytokine in the generation of professional antigen presenting cells, particularly dendritic cells. A recombinant molecule in which Flt3-ligand is linked to an antigen (to which immunity is desired) targets the antigen to APCs such as dendritic cells. Using HPV-16 E7 as an antigen, the effect of Flt3-ligand (FL)-antigen constructs (FIG. 19) on the potency of antigen-specific immunity generated by naked DNA vaccines was evaluated. Residues 1–189 of SEQ ID NO:25 are FL-derived, and residues 190–287 are E7-derived ("Z" in position 288 of SEQ ID NO:25 indicates a stop). DNA constructs encoding FL-E7 fusion polypeptides were administered intradermally via gene gun. Vaccines containing chimeric FL/E7 fusion genes were foudn to dramatically increase the frequency of E7-specific CD8+ T cells relative to vaccines containing the wild-type E7 gene in the absence of FL-encoding sequences. In vitro studies indicated that cells transfected with FL/E7 DNA presented E7 antigen through the MHC class I pathway in a more efficient manner than cells transfected with wild-type E7 DNA. Furthermore, bone marrow-derived dendritic cells pulsed with FL/E7 fusion protein presented E7 antigen through the MHC class I pathway in a more efficient manner than dendritic cells pulsed with wild-type E7 protein. More importantly, this fusion converted a less effective vaccine into one with significant potency against established E7-expressing metastatic tumors. Interestingly, FL/E7 fusion vaccines mainly targeted CD8+ T cells and antitumor effects were completely CD4-independent. These data indicate that fusion of Flt3-ligand DNA to an antigen-encoding enhances the potency of DNA vaccines via CD8-dependent pathways.

Other embodiments are within the following claims.

What is claimed is:

1. An immunogenic nucleic acid composition comprising
   (a) a first DNA encoding a heat shock protein (HSP) or an immutnogenically active fragment thereof, operably linked to
   (b) a second DNA encoding a MHC class I-restricted antigen, which antigen is the E6 or E7 protein of a buman papillomavirus (HPV), or an epitope of E6 or E7, which composition, when administered to a mammalian subject, induces an immune response that is
      (i) specific for said HPV E6 or E7 protein or epitope encoded by said second DNA, and
      (ii) greater in magnitude than an immune response induced by DNA encoding said protein or epitope alone without the DNA encoding the HSP or HSP fragment.

2. The composition of claim 1 wherein said first DNA encodes an immunogenically active carboxy-terminal fragment of said HSP.

3. The composition of claim 1, wherein said HSP is *Mycobaclerium tuberculosis* HSP70.

4. The composition of claim 2, wherein said carboxy-terminal fragment is a fragment of *Mycobacterium tuberculosis* HSP70 that comprises the amino acid sequence of residues 517–625 of SEQ ID NO:9.

5. The composition of claim 4, further comprising a third operably linked DNA which encodes a *Mycobactenum tuberculosis* HSP70 amino-terminal polypeptide fragment comprising residues 161–370 of SEQ ID NO:9.

6. The composition of claim 1, wherein said HPV is an HPV that causes or is present in cervical cancer.

7. The composition of claim 6, wherein said HPV is HPV-16.

8. The composition of claim 7, wherein said antigen is an epitope of HPV E6.

9. The composition of claim 7, wherein said antigen is an epitope of HPV E7.

10. An immunogenic nucleic acid composition comprising a first DNA encoding a *Mycobacterium tuberculosis* HSP70 carboxy-termina polypeptide comprising the amino acid sequence of residues 517 to 625 of SEQ ID NO:9 operably linked to a second DNA encoding a MHC class I-restricted antigen, which antigen is the HPV E6 or E7 protein, or an epitope of E6 or E7.

11. The composition of claim 10, further comprising an operably linked third DNA encoding a *Mycobacterium tuberculosis* HSP70 amino-terminal polypeptide comprising residues 161–370 of SEQ ID NO:9.

12. The composition of claim 10, wherein said HPV is HPV-16.

13. The composition of claim 12, wherein said antigen is an epitope of HPV E6.

14. The composition of claim 12, wherein said antigen is an epitope of HPV E7.

15. An immunogenic DNA composition comprising a DNA sequence encoding a fusion polypeptide of the C-terminal domain of *Mycobacterium tuberculosis* HSP70 and an epitope of HPV E7.

16. A DNA vaccine composition comprising:
   (a) a plasmid vector which comprises the nucleic acid composition of claim 1;
   (b) an immunologically otpharmaceutically acceptable excipient or carrier which vaccine composition has the following immunoaenic properties:
   when annstered to a mammalian subject, induces an immune response that is
      (i) specific for said antigen encoded by said second DNA, and
      (ii) greater in magnitude than an imnmune response induced by a control vaccine comprising DNA encoding said antigen alone without DNA encoding the HSP or HSP fragment.

17. The DNA vaccine composition of claim 16 wherein said first DNA encodes a *Mycobacterium tuberculosis* HSP70 catboxy-terminal polypeptide comprising the amino acid sequence of residues 517 to 625 of SEQ ID NO:9.

18. The DNA vaccine composition of claim 16 wherein said HPV is an HPV that causes or is present in cervical cancer.

19. The DNA vaccine composition of claim 18 wherein said antigen is an epitope of an HPV E7 protein.

20. A method of inducing an enhanced cytotoxic T lymphocyte (CTL) response to an antigen, which antigen is a HPV E6 or E7 protein, or an epitope of E6 or E7, in a mammal comprising administering to said mammal an effective amount of the nucleic acid composition of claim 1, thereby inducing an enhanced CTL response which is characterized in that it is (a) specific for said antigen encoded by said DNA composition, and (b) greater in magnitude than a CTL response induced by DNA encoding said antigen alone, without DNA encoding the HSP or HSP fragment.

21. The method of claim 20, wherein said first DNA encodes a *Mycobacterium tuberculosis* HSP70 carboxy-terminal polypeptide comprising the amino acid sequence of residues 517 to 625 of SEQ ID NO:9.

22. The method of claim 20 wherein said HPV is an HPV that causes or is present in cervical cancer.

23. The method of claim 22 wherein said antigen is an epitope of an HPV E7 protein.

24. The method of claim 20 wherein the nucleic acid composition is administered as naked DNA.

25. The method of claim 20, wherein the nucleic acid composition is administered in a liposome.

26. A method of inducing in a mammal a T cell-mediated immune response specific for an antigen, which antigen is the E6 or E7 protein of HPV, or an epitope of E6 or E7, comprising administering to said mammal an effective amount of the nucleic acid composition of claim 1, hereby inducing said T cell response which is characterized in that it is (a) specific for said antigen encoded by said DNA composition, and (b) greater in nagnitude than a T cell response induced by DNA encoding said antigen alone, without DNA encoding said HSP or HSP fragment.

27. A method of inducing antigen-specific antitumor immune response in a mammalian subject bearing an HPV E6 or E7 antigen-expressing tumor, comprising administering an effective amount of the DNA vaccine composition of claim 16 to said subject, wherein said MHC class I-restricted BPV E6 or E7 antigen encoded by said second DNA sequence is a tumor antigen that is (1) expressed by cells of said tumor, and (2) recognized by the subject's T lymphocytes, thereby inducing said antitumor immune response, which response is characterized by (a) an increase in the number, frequency or activity of T lymphocytes that are specific for said tumor antigen, and/or (b) a reduction in the size or growth rate of said tumor, wherein (1) said increase in said number, frequency or activity of T lymphocytes or (2) said reduction in tumor size or growth rate, is relative to a control subject to whom;

(i) none of said vaccine composition has been administered, or (ii) a control DNA composition encoding said tumor antigen alone, without DNA encoding the HSP or HSP fragment, has been administered.

28. The method of claim 27 wherein said first DNA encodes a *Mycobacterium tuberculosis* HSP70 carboxy-terminal polypeptide comprising the amino acid sequence of residues 517 to 625 of SEQ ID NO:9.

29. The method of claim 27 wherein said is an HPV that causes or is present in cervical cancer.

30. The method of claim 29 wherein said antigen is an epitope of an HPV E7 protein.

31. The method of claim 27 wherein said T lymphocytes are CD8+ T lymphocytes.

32. The method of claim 31, wherein said CD8+ T lymphocytes are CTL.

33. The method of claim 20 wherein said administering is by a route selected from the group consisting of intradermal, intramuscular, subcutaneous or intravenous.

34. The method of claim 27, wherein said administering is by a route selected from the group consisting of intradermal, intramuscular, subcutaneous or intravenous.

* * * * *

SEQUENCE LISTING

<160> NUMBER OF SEQ ID NOS: 25

<210> SEQ ID NO 1
<211> LENGTH: 141
<212> TYPE: PRT
<213> ORGANISM: mouse

<400> SEQUENCE: 1

Met Trp Leu Gln Asn Leu Leu Phe Leu Gly Ile Val Val Tyr Ser Leu
 1               5                  10                  15

Ser Ala Pro Thr Arg Ser Pro Ile Thr Val Thr Arg Pro Trp Lys His
             20                  25                  30

Val Glu Ala Ile Lys Glu Ala Leu Asn Leu Leu Asp Asp Met Pro Val
         35                  40                  45

Thr Leu Asn Glu Glu Val Glu Val Val Ser Asn Glu Phe Ser Phe Lys
     50                  55                  60

Lys Leu Thr Cys Val Gln Thr Arg Leu Lys Ile Phe Glu Gln Gly Leu
 65                  70                  75                  80

Arg Gly Asn Phe Thr Lys Leu Lys Gly Ala Leu Asn Met Thr Ala Ser
                 85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Val Gln Lys
    130                 135                 140

<210> SEQ ID NO 2
<211> LENGTH: 916
<212> TYPE: DNA
<213> ORGANISM: mouse

<400> SEQUENCE: 2
gagctcagca agcgctctcc cccaattccc ttagccaaag tggacgccac cgaacagaca      60
gacctaggct aagaggtttg atgtctctgg ctacccgact ttgaaaattt tccgcaaagg     120
aaggcctttt gactacaatg gcccacgaga gaaaggctaa ggtcctgagg aggatgtggc     180
tgcagaattt acttttcctg ggcattgtgg tctacagcct ctcagcaccc acccgctcac     240
ccatcactgt cacccggcct tggaagcatg tagaggccat caagaagcc ctgaacctcc      300 tggatgacat gcctgtcaca ttgaatgaag aggtagaagt cgtctctaac gagttctcct     360
tcaagaagct aacatgtgtg cagacccgcc tgaagatatt cgagcagggt ctacggggca     420
atttcaccaa actcaagggc gccttgaaca tgacagccag ctactaccag acatactgcc     480
ccccaactcc ggaaacggac tgtgaaacac aagttaccac ctatgcggat ttcatagaca     540
gccttaaaac ctttctgact gatatcccct tgaatgcaa aaaaccagtc caaaaatgag       600
gaagcccagg ccagctctga atccagcttc tcagactgct gcttttgtgc ctgcgtaatg     660
agccaggaac tcggaatttc tgccttaaag ggaccaagag atgtggcaca gccacagttg     720
gagggcagta tagccctctg aaaacgctga ctcagcttgg acagcggcaa gacaaacgag     780
agatattttc tactgatagg gaccattata tttatttata tatttatatt ttttaaatat     840
ttatttattt atttatttaa ttttgcaact ctatttattg agaatgtctt accagataat     900
aaattattaa aacttt                                                      916

```
<210> SEQ ID NO 3
<211> LENGTH: 638
<212> TYPE: PRT
<213> ORGANISM: Pseudomonas

<400> SEQUENCE: 3

Met His Leu Ile Pro His Trp Ile Pro Leu Val Ala Ser Leu Gly Leu
  1               5                  10                  15

Leu Ala Gly Gly Ser Ser Ala Ser Ala Ala Glu Glu Ala Phe Asp Leu
             20                  25                  30

Trp Asn Glu Cys Ala Lys Ala Cys Val Leu Asp Leu Lys Asp Gly Val
         35                  40                  45

Arg Ser Ser Arg Met Ser Val Asp Pro Ala Ile Ala Asp Thr Asn Gly
 50                  55                  60

Gln Gly Val Leu His Tyr Ser Met Val Leu Glu Gly Gly Asn Asp Ala
 65                  70                  75                  80

Leu Lys Leu Ala Ile Asp Asn Ala Leu Ser Ile Thr Ser Asp Gly Leu
                 85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125

Pro Ile Gly His Glu Lys Pro Ser Asn Ile Lys Val Phe Ile His Glu
    130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Val Met Ala Gln Thr Gln Pro Arg Arg
        195                 200                 205

Glu Lys Arg Trp Ser Glu Trp Ala Ser Gly Lys Val Leu Cys Leu Leu
    210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
            260                 265                 270

Leu His Phe Pro Glu Gly Gly Ser Leu Ala Ala Leu Thr Ala His Gln
        275                 280                 285

Ala Cys His Leu Pro Leu Glu Thr Phe Thr Arg His Arg Gln Pro Arg
    290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Gly Asp Leu Gly Glu
            340                 345                 350

Ala Ile Arg Glu Gln Pro Glu Gln Ala Arg Leu Ala Leu Thr Leu Ala
        355                 360                 365

Ala Ala Glu Ser Glu Arg Phe Val Arg Gln Gly Thr Gly Asn Asp Glu
    370                 375                 380
```

-continued

```
Ala Gly Ala Ala Asn Ala Asp Val Val Ser Leu Thr Cys Pro Val Ala
385                 390                 395                 400
Ala Gly Glu Cys Ala Gly Pro Ala Asp Ser Gly Asp Ala Leu Leu Glu
            405                 410                 415
Arg Asn Tyr Pro Thr Gly Ala Glu Phe Leu Gly Asp Gly Gly Asp Val
        420                 425                 430
Ser Phe Ser Thr Arg Gly Thr Gln Asn Trp Thr Val Glu Arg Leu Leu
    435                 440                 445
Gln Ala His Arg Gln Leu Glu Glu Arg Gly Tyr Val Phe Val Gly Tyr
450                 455                 460
His Gly Thr Phe Leu Glu Ala Ala Gln Ser Ile Val Phe Gly Val
465                 470                 475                 480
Arg Ala Arg Ser Gln Asp Leu Asp Ala Ile Trp Arg Gly Phe Tyr Ile
            485                 490                 495
Ala Gly Asp Pro Ala Leu Ala Tyr Gly Tyr Ala Gln Asp Gln Glu Pro
        500                 505                 510
Asp Ala Arg Gly Arg Ile Arg Asn Gly Ala Leu Leu Arg Val Tyr Val
    515                 520                 525
Pro Arg Ser Ser Leu Pro Gly Phe Tyr Arg Thr Ser Leu Thr Leu Ala
530                 535                 540
Ala Pro Glu Ala Ala Gly Glu Val Glu Arg Leu Ile Gly His Pro Leu
545                 550                 555                 560
Pro Leu Arg Leu Asp Ala Ile Thr Gly Pro Glu Glu Glu Gly Gly Arg
            565                 570                 575
Leu Glu Thr Ile Leu Gly Trp Pro Leu Ala Glu Arg Thr Val Val Ile
        580                 585                 590
Pro Ser Ala Ile Pro Thr Asp Pro Arg Asn Val Gly Gly Asp Leu Asp
    595                 600                 605
Pro Ser Ser Ile Pro Asp Lys Glu Gln Ala Ile Ser Ala Leu Pro Asp
610                 615                 620
Tyr Ala Ser Gln Pro Gly Lys Pro Pro Arg Glu Asp Leu Lys
625                 630                 635
```

<210> SEQ ID NO 4
<211> LENGTH: 2760
<212> TYPE: DNA
<213> ORGANISM: Pseudomonas

<400> SEQUENCE: 4

```
ctgcagctgg tcaggccgtt tccgcaacgc ttgaagtcct ggccgatata ccggcagggc      60
cagccatcgt tcgacgaata aagccacctc agccatgatg ccctttccat ccccagcgga     120
accccgacat ggacgccaaa gccctgctcc tcggcagcct ctgcctggcc gccccattcg     180
ccgacgcggc gacgctcgac aatgctctct ccgcctgcct cgccgcccgg ctcggtgcac     240
cgcacacggc ggagggccag ttgcacctgc cactcaccct tgaggcccgg cgctccaccg     300
gcgaatgcgc ctgtacctcg cgctggtgc  gatatcggct gctggccagg ggcgccagcg     360
ccgacagcct cgtgcttcaa gagggctgct cgatagtcgc caggacacgc cgcgcacgct     420
gaccctggcg gcgacgccg  gcttggcgag cggccgcgaa ctggtcgtca ccctgggttg     480
tcaggcgcct gactgacagg ccgggctgcc accaccaggc cgagatggac gccctgcatg     540
tatcctccga tcggcaagcc tcccgttcgc acattcacca ctctgcaatc cagttcataa     600
atcccataaa agccctcttc cgctccccgc cagcctcccc gcatcccgca ccctagacgc     660
```

-continued

```
cccgccgctc tccgccggct cgcccgacaa gaaaaaccaa ccgctcgatc agcctcatcc      720
ttcacccatc acaggagcca tcgcgatgca cctgatacco cattggatcc ccctggtcgc      780
cagcctcggc ctgctcgccg gcggctcgtc cgcgtccgcc gccgaggaag ccttcgacct      840
ctggaacgaa tgcgccaaag cctgcgtgct cgacctcaag gacggcgtgc gttccagccg      900
catgagcgtc gacccggcca tcgccgacac caacggccag ggcgtgctgc actactccat      960
ggtcctggag ggcggcaacg acgcgctcaa gctggccatc gacaacgccc tcagcatcac     1020
cagcgacggc ctgaccatcc gcctcgaagg cggcgtcgag ccgaacaagc cggtgcgcta     1080
cagctacacg cgccaggcgc gcggcagttg gtcgctgaac tggctggtac cgatcggcca     1140
cgagaagccc tcgaacatca aggtgttcat ccacgaactg aacgccggca ccagctcag      1200 ccacatgtcg ccgatctaca ccatcgagat gggcgacgag ttgctggcga agctggcgcg     1260
cgatgccacc ttcttcgtca gggcgcacga gagcaacgag atgcagccga cgctcgccat     1320
cagccatgcc ggggtcagcg tggtcatggc ccagacccag ccgcgccggg aaaagcgctg     1380
gagcgaatgg gccagcggca aggtgttgtg cctgctcgac ccgctggacg gggtctacaa     1440
ctacctcgcc cagcaacgct gcaacctcga cgatacctgg gaaggcaaga tctaccgggt     1500
gctcgccggg aacccggcga agcatgacct ggacatcaaa cccacggtca tcagtcatcg     1560
cctgcacttt cccgagggcg gcagcctggc cgcgctgacc gcgcaccagg cttgccacct     1620
gccgctggag actttcacccc gtcatcgcca gccgcgcggc tgggaacaac tggagcagtg     1680
cggctatccg gtgcagcggc tggtcgccct ctacctggcg gcgcggctgt cgtggaacca     1740
ggtcgaccag gtgatccgca acgccctggc cagccccggc agcggcggcg acctgggcga     1800
agcgatccgc gagcagccgg agcaggcccg tctggccctg accctggccg ccgccgagag     1860
cgagcgcttc gtccggcagg gcaccggcaa cgacgaggcc ggcgcggcca acgccgacgt     1920
ggtgagcctg acctgcccgg tcgccgccgg tgaatgcgcg ggcccggcgg acagcggcga     1980
cgccctgctg gagcgcaact atcccactgg cgcggagttc ctcggcgacg gcggcgacgt     2040
cagcttcagc acccgcggca cgcagaactg gacggtggag cggctgctcc aggcgcaccg     2100
ccaactggag gagcgcggct atgtgttcgt cggctaccac ggcaccttcc tcgaagcggc     2160
gcaaagcatc gtcttcggcg gggtgcgcgc gcgcagccag gacctcgacg cgatctggcg     2220
cggtttctat atcgccggcg atccggcgct ggcctacggc tacgcccagg accaggaacc     2280
cgacgcacgc ggccggatcc gcaacggtgc cctgctgcgg gtctatgtgc cgcgctcgag     2340
cctgccgggc ttctaccgca ccagcctgac cctggccgcc ccggaggcgg cgggcgaggt     2400
cgaacggctg atcggccatc cgctgccgct gcgcctggac gccatcaccg gccccgagga     2460
ggaaggcggg cgcctggaga ccattctcgg ctggccgctg gccgagcgca ccgtggtgat     2520
tccctcggcg atccccaccg acccgcgcaa cgtcggcggc gacctcgacc cgtccagcat     2580
ccccgacaag gaacaggcga tcagcgccct gccggactac gccagccagc ccggcaaacc     2640
gccgcgcgag gacctgaagt aactgccgcg accggccggc tcccttcgca ggagccggcc     2700
ttctcggggc ctggccatac atcaggtttt cctgatgcca gcccaatcga atatgaattc     2760
```

<210> SEQ ID NO 5
<211> LENGTH: 9
<212> TYPE: PRT
<213> ORGANISM: human papillomavirus -continued

```
<400> SEQUENCE: 5

Arg Ala His Tyr Asn Ile Val Thr Phe
1               5

<210> SEQ ID NO 6
<211> LENGTH: 38
<212> TYPE: PRT
<213> ORGANISM: human papillomavirus

<400> SEQUENCE: 6

Asp Ser Ser Glu Glu Asp Glu Ile Asp Gly Pro Ala Gly Gln Ala
1               5                   10                  15

Glu Pro Asp Arg Ala His Tyr Asn Ile Val Thr Phe Cys Cys Lys Cys
            20                  25                  30

Asp Ser Thr Leu Arg Leu
            35

<210> SEQ ID NO 7
<211> LENGTH: 98
<212> TYPE: PRT
<213> ORGANISM: human papillomavirus

<400> SEQUENCE: 7

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 8
<211> LENGTH: 297
<212> TYPE: DNA
<213> ORGANISM: human papillomavirus

<400> SEQUENCE: 8
atgcatggag atacacctac attgcatgaa tatatgttag atttgcaacc agagacaact    60
gatctctact gttatgagca attaaatgac agctcagagg aggaggatga aatagatggt   120
ccagctggac aagcagaacc ggacagagcc cattacaata ttgtaacctt ttgttgcaag   180
tgtgactcta cgcttcggtt gtgcgtacaa agcacacacg tagacattcg tactttggaa   240
gacctgttaa tgggcacact aggaattgtg tgccccatct gttctcagaa accataa      297

<210> SEQ ID NO 9
<211> LENGTH: 625
<212> TYPE: PRT
<213> ORGANISM: Mycobacterium tuberculosis

<400> SEQUENCE: 9

Met Ala Arg Ala Val Gly Ile Asp Leu Gly Thr Thr Asn Ser Val Val
1               5                   10                  15
```

```
Ser Val Leu Glu Gly Gly Asp Pro Val Val Ala Asn Ser Glu Gly
         20                  25                  30

Ser Arg Thr Thr Pro Ser Ile Val Ala Phe Ala Arg Asn Gly Glu Val
         35                  40                  45

Leu Val Gly Gln Pro Ala Lys Asn Gln Ala Val Thr Asn Val Asp Arg
 50                  55                  60

Thr Val Arg Ser Val Lys Arg His Met Gly Ser Asp Trp Ser Ile Glu
65                  70                  75                  80

Ile Asp Gly Lys Lys Tyr Thr Ala Pro Glu Ile Ser Ala Arg Ile Leu
                 85                  90                  95

Met Lys Leu Lys Arg Asp Ala Glu Ala Tyr Leu Gly Glu Asp Ile Thr
                100                 105                 110

Asp Ala Val Ile Thr Thr Pro Ala Tyr Phe Asn Asp Ala Gln Arg Gln
             115                 120                 125

Ala Thr Lys Asp Ala Gly Gln Ile Ala Gly Leu Asn Val Leu Arg Ile
         130                 135                 140

Val Asn Glu Pro Thr Ala Ala Leu Ala Tyr Gly Leu Asp Lys Gly
145                 150                 155                 160

Glu Lys Glu Gln Arg Ile Leu Val Phe Asp Leu Gly Gly Thr Phe
                165                 170                 175

Asp Val Ser Leu Leu Glu Ile Gly Glu Gly Val Glu Val Arg Ala
             180                 185                 190

Thr Ser Gly Asp Asn His Leu Gly Gly Asp Asp Trp Asp Gln Arg Val
         195                 200                 205

Val Asp Trp Leu Val Asp Lys Phe Lys Gly Thr Ser Gly Ile Asp Leu
         210                 215                 220

Thr Lys Asp Lys Met Ala Met Gln Arg Leu Arg Glu Ala Ala Glu Lys
225                 230                 235                 240

Ala Lys Ile Glu Leu Ser Ser Gln Ser Thr Ser Ile Asn Leu Pro
             245                 250                 255

Tyr Ile Thr Val Asp Ala Asp Lys Asn Pro Leu Phe Leu Asp Glu Gln
             260                 265                 270

Leu Thr Arg Ala Glu Phe Gln Arg Ile Thr Gln Asp Leu Leu Asp Arg
         275                 280                 285

Thr Arg Lys Pro Phe Gln Ser Val Ile Ala Asp Thr Gly Ile Ser Val
         290                 295                 300

Ser Glu Ile Asp His Val Val Leu Val Gly Gly Ser Thr Arg Met Pro
305                 310                 315                 320

Ala Val Thr Asp Leu Val Lys Glu Leu Thr Gly Gly Lys Glu Pro Asn
             325                 330                 335

Lys Gly Val Asn Pro Asp Glu Val Val Ala Val Gly Ala Ala Leu Gln
         340                 345                 350

Ala Gly Val Leu Lys Gly Glu Val Lys Asp Val Leu Leu Leu Asp Val
         355                 360                 365

Thr Pro Leu Ser Leu Gly Ile Glu Thr Lys Gly Gly Val Met Thr Arg
 370                 375                 380

Leu Ile Glu Arg Asn Thr Thr Ile Pro Thr Lys Arg Ser Glu Thr Phe
385                 390                 395                 400

Thr Thr Ala Asp Asp Asn Gln Pro Ser Val Gln Ile Gln Val Tyr Gln
             405                 410                 415

Gly Glu Arg Glu Ile Ala Ala His Asn Lys Leu Leu Gly Ser Phe Glu
         420                 425                 430
```

-continued

```
Leu Thr Gly Ile Pro Pro Ala Pro Arg Gly Ile Pro Gln Ile Glu Val
            435                 440                 445
Thr Phe Asp Ile Asp Ala Asn Gly Ile Val His Val Thr Ala Lys Asp
        450                 455                 460
Lys Gly Thr Gly Lys Glu Asn Thr Ile Arg Ile Gln Glu Gly Ser Gly
465                 470                 475                 480
Leu Ser Lys Glu Asp Ile Asp Arg Met Ile Lys Asp Ala Glu Ala His
                485                 490                 495
Ala Glu Glu Asp Arg Lys Arg Glu Glu Ala Asp Val Arg Asn Gln
            500                 505                 510
Ala Glu Thr Leu Val Tyr Gln Thr Glu Lys Phe Val Lys Glu Gln Arg
        515                 520                 525
Glu Ala Glu Gly Gly Ser Lys Val Pro Glu Asp Thr Leu Asn Lys Val
    530                 535                 540
Asp Ala Ala Val Ala Glu Ala Lys Ala Ala Leu Gly Gly Ser Asp Ile
545                 550                 555                 560
Ser Ala Ile Lys Ser Ala Met Glu Lys Leu Gly Gln Glu Ser Gln Ala
                565                 570                 575
Leu Gly Gln Ala Ile Tyr Glu Ala Ala Gln Ala Ala Ser Gln Ala Thr
            580                 585                 590
Gly Ala Ala His Pro Gly Gly Pro Gly Gly Ala His Pro Gly Ser
        595                 600                 605
Ala Asp Asp Val Val Asp Ala Glu Val Val Asp Asp Gly Arg Glu Ala
    610                 615                 620
Lys
625

<210> SEQ ID NO 10
<211> LENGTH: 1878
<212> TYPE: DNA
<213> ORGANISM: Mycobacterium tuberculosis

<400> SEQUENCE: 10
atggctcgtg cggtcgggat cgacctcggg accaccaact ccgtcgtctc ggttctggaa      60
ggtggcgacc cggtcgtcgt cgccaactcc gagggctcca ggaccacccc gtcaattgtc     120
gcgttcgccc gcaacggtga ggtgctggtc ggccagcccg ccaagaacca ggcagtgacc     180
aacgtcgatc gcaccgtgcg ctcggtcaag cgacacatgg gcagcgactg gtccatagag     240
attgacggca gaaatacac cgcgccggag atcagcgccc gcattctgat gaagctgaag     300
cgcgacgccg aggcctacct cggtgaggac attaccgacg cggttatcac gacgcccgcc     360
tacttcaatg acgcccagcg tcaggccacc aaggacgccg ccagatcgc cggcctcaac     420 gtgctgcgga tcgtcaacga gccgaccgcg ccgcgctgg cctacggcct cgacaagggc     480
gagaaggagc agcgaatcct ggtcttcgac ttgggtggtg gcactttcga cgtttccctg     540
ctggagatcg cgagggtgt ggttgaggtc cgtgccactt cgggtgacaa ccacctcggc     600
ggcgacgact gggaccagcg ggtcgtcgat tggctggtgg acaagttcaa gggcaccagc     660
ggcatcgatc tgaccaagga caagatggcg atgcagcggc tgcgggaagc cgccgagaag     720
gcaaagatcg agctgagttc gagtcagtcc acctcgatca acctgcccta catcaccgtc     780
gacgccgaca gaacccgtt gttcttagac gagcagctga cccgcgcgga gttccaacgg     840
atcactcagg acctgctgga ccgcactcgc aagccgttcc agtcggtgat cgctgacacc     900
ggcatttcgg tgtcggagat cgatcacgtt gtgctcgtgg gtggttcgac ccggatgccc     960
```

```
gcggtgaccg atctggtcaa ggaactcacc ggcggcaagg aacccaacaa gggcgtcaac    1020
cccgatgagg ttgtcgcggt gggagccgct ctgcaggccg cgtcctcaa gggcgaggtg    1080 aaagacgttc tgctgcttga tgttaccccg ctgagcctgg gtatcgagac caagggcggg    1140
gtgatgacca ggctcatcga gcgcaacacc acgatcccca ccaagcggtc ggagactttc    1200
accaccgccg acgacaacca accgtcggtg cagatccagg tctatcaggg ggagcgtgag    1260
atcgccgcgc acaacaagtt gctcgggtcc ttcgagctga ccggcatccc gccggcgccg    1320
cgggggattc cgcagatcga ggtcactttc gacatcgacg ccaacggcat tgtgcacgtc    1380
accgccaagg acaagggcac cggcaaggag aacacgatcc gaatccagga aggctcgggc    1440
ctgtccaagg aagacattga ccgcatgatc aaggacgccg aagcgcacgc cgaggaggat    1500
cgcaagcgtc gcgaggaggc cgatgttcgt aatcaagccg agacattggt ctaccagacg    1560
gagaagttcg tcaaagaaca gcgtgaggcc gaggtggtt cgaaggtacc tgaagacacg    1620
ctgaacaagg ttgatgccgc ggtggcggaa gcgaaggcg cacttggcgg atcggatatt    1680
tcggccatca gtcgcgat ggagaagctg ggccaggagt cgcaggctct ggggcaagcg    1740
atctacgaag cagctcaggc tgcgtcacag gccactggcg ctgcccaccc cggcggcgag    1800
ccgggcggtg cccaccccgg ctcggctgat gacgttgtgg acgcggaggt ggtcgacgac    1860
ggccgggagg ccaagtga                                                 1878

<210> SEQ ID NO 11
<211> LENGTH: 30
<212> TYPE: DNA
<213> ORGANISM: synthetic

<400> SEQUENCE: 11
ggggagatct ggatgtggct gcagaattta                                      30

<210> SEQ ID NO 12
<211> LENGTH: 31
<212> TYPE: DNA
<213> ORGANISM: synthetic

<400> SEQUENCE: 12
gggagaattc ttttggactg gttttttgca t                                    31

<210> SEQ ID NO 13
<211> LENGTH: 30
<212> TYPE: DNA
<213> ORGANISM: synthetic

<400> SEQUENCE: 13
gggagaattc tcgcctgtca ctttcccgag                                      30

<210> SEQ ID NO 14
<211> LENGTH: 28
<212> TYPE: DNA
<213> ORGANISM: synthetic

<400> SEQUENCE: 14
ggaaggatcc agttctgcgt gccgcggg                                        28

<210> SEQ ID NO 15
<211> LENGTH: 30
<212> TYPE: DNA
<213> ORGANISM: synthetic
```

-continued

```
<400> SEQUENCE: 15
gggaggatcc tcatgcatgg agatacacct                                      30

<210> SEQ ID NO 16
<211> LENGTH: 29
<212> TYPE: DNA
<213> ORGANISM: synthetic

<400> SEQUENCE: 16
ggggaagctt atcctgagaa cagatgggg                                       29

<210> SEQ ID NO 17
<211> LENGTH: 20
<212> TYPE: DNA
<213> ORGANISM: synthetic

<400> SEQUENCE: 17
cccagatcta atcatgcatg                                                 20

<210> SEQ ID NO 18
<211> LENGTH: 29
<212> TYPE: DNA
<213> ORGANISM: synthetic

<400> SEQUENCE: 18
ggggaagctt atcctgagaa cagatgggg                                       29

<210> SEQ ID NO 19
<211> LENGTH: 2172
<212> TYPE: DNA
<213> ORGANISM: human papillomavirus/Mycobacterium tuberculosis

<400> SEQUENCE: 19
atgcatggag atacacctac attgcatgaa tatatgttag atttgcaacc agagacaact     60
gatctctact gttatgagca attaaatgac agctcagagg aggaggatga aatagatggt    120
ccagctggac aagcagaacc ggacagagcc cattacaata ttgtaacctt ttgttgcaag    180
tgtgactcta cgcttcggtt gtgcgtacaa agcacacacg tagacattcg tactttggaa    240
gacctgttaa tgggcacact aggaattgtg tgccccatct gttctcaagg atccatggct    300
cgtgcggtcg ggatcgacct cgggaccacc aactccgtcg tctcggttct ggaaggtggc    360
gacccggtcg tcgtcgccaa ctccgagggc tccaggacca cccgtcaat tgtcgcgttc    420 gcccgcaacg gtgaggtgct ggtcggccag cccgccaaga accaggcagt gaccaacgtc    480
gatcgcaccg tgcgctcggt caagcgacac atgggcagcg actggtccat agagattgac    540
ggcaagaaat acaccgcgcc ggagatcagc gcccgcattc tgatgaagct gaagcgcgac    600
gccgaggcct acctcggtga ggacattacc gacgcggtta tcacgacgcc cgcctacttc    660
aatgacgccc agcgtcaggc caccaaggac gccggccaga tcgccggcct caacgtgctg    720
cggatcgtca acgagccgac cgcggccgcg ctggcctacg gcctcgacaa gggcgagaag    780
gagcagcgaa tcctggtctt cgacttgggt ggtggcactt tcgacgtttc cctgctggag    840
atcggcgagg gtgtggttga ggtccgtgcc acttcgggtg acaaccacct cggcggcgac    900
gactgggacc agcgggtcgt cgattggctg gtggacaagt tcaagggcac cagcggcatc    960
gatctgacca aggacaagat ggcgatgcag cggctgcggg aagccgccga aaggcaaag   1020 atcgagctga gttcgagtca gtccacctcg atcaacctgc cctacatcac cgtcgacgcc   1080
```

-continued

```
gacaagaacc cgttgttctt agacgagcag ctgacccgcg cggagttcca acggatcact   1140
caggacctgc tggaccgcac tcgcaagccg ttccagtcgg tgatcgctga caccggcatt   1200
tcggtgtcgg agatcgatca cgttgtgctc gtgggtggtt cgacccggat gcccgcggtg   1260
accgatctgg tcaaggaact caccggcggc aaggaaccca acaagggcgt caaccccgat   1320
gaggttgtcg cggtgggagc cgctctgcag gccggcgtcc tcaagggcga ggtgaaagac   1380
gttctgctgc ttgatgttac cccgctgagc ctgggtatcg agaccaaggg cggggtgatg   1440
accaggctca tcgagcgcaa caccacgatc cccaccaagc ggtcggagac tttcaccacc   1500
gccgacgaca accaaccgtc ggtgcagatc caggtctatc agggggagcg tgagatcgcc   1560
gcgcacaaca agttgctcgg gtccttcgag ctgaccggca tcccgccggc gccgcggggg   1620
attccgcaga tcgaggtcac tttcgacatc gacgccaacg gcattgtgca cgtcaccgcc   1680
aaggacaagg gcaccggcaa ggagaacacg atccgaatcc aggaaggctc gggcctgtcc   1740
aaggaagaca ttgaccgcat gatcaaggac gccgaagcgc acgccgagga ggatcgcaag   1800
cgtcgcgagg aggccgatgt tcgtaatcaa gccgagacat tggtctacca gacggagaag   1860
ttcgtcaaag aacagcgtga ggccgagggt ggttcgaagg tacctgaaga cacgctgaac   1920
aaggttgatg ccgcggtggc ggaagcgaag gcggcacttg gcggatcgga tatttcggcc   1980
atcaagtcgg cgatggagaa gctgggccag gagtcgcagg ctctggggca agcgatctac   2040
gaagcagctc aggctgcgtc acaggccact ggcgctgccc accccggcgg cgagccgggc   2100
ggtgcccacc ccggctcggc tgatgacgtt gtggacgcgg aggtggtcga cgacggccgg   2160
gaggccaagt ga                                                      2172
```

<210> SEQ ID NO 20
<211> LENGTH: 723
<212> TYPE: PRT
<213> ORGANISM: human papillomavirus/Mycobacterium tuberculosis

<400> SEQUENCE: 20

```
Met His Gly Asp Thr Pro Thr Leu His Glu Tyr Met Leu Asp Leu Gln
  1               5                  10                  15

Pro Glu Thr Thr Asp Leu Tyr Cys Tyr Glu Gln Leu Asn Asp Ser Ser
             20                  25                  30

Glu Glu Glu Asp Glu Ile Asp Gly Pro Ala Gly Gln Ala Glu Pro Asp
         35                  40                  45

Arg Ala His Tyr Asn Ile Val Thr Phe Cys Cys Lys Cys Asp Ser Thr
     50                  55                  60

Leu Arg Leu Cys Val Gln Ser Thr His Val Asp Ile Arg Thr Leu Glu
 65                  70                  75                  80

Asp Leu Leu Met Gly Thr Leu Gly Ile Val Cys Pro Ile Cys Ser Gln
                 85                  90                  95

Gly Ser Met Ala Arg Ala Val Gly Ile Asp Leu Gly Thr Thr Asn Ser
            100                 105                 110

Val Val Ser Val Leu Glu Gly Gly Asp Pro Val Val Ala Asn Ser
        115                 120                 125

Glu Gly Ser Arg Thr Thr Pro Ser Ile Val Ala Phe Ala Arg Asn Gly
    130                 135                 140

Glu Val Leu Val Gly Gln Pro Ala Lys Asn Gln Ala Val Thr Asn Val
145                 150                 155                 160

Asp Arg Thr Val Arg Ser Val Lys Arg His Met Gly Ser Asp Trp Ser
                165                 170                 175
```

-continued

```
Ile Glu Ile Asp Gly Lys Lys Tyr Thr Ala Pro Glu Ile Ser Ala Arg
            180                 185                 190
Ile Leu Met Lys Leu Lys Arg Asp Ala Glu Ala Tyr Leu Gly Glu Asp
        195                 200                 205
Ile Thr Asp Ala Val Ile Thr Thr Pro Ala Tyr Phe Asn Asp Ala Gln
    210                 215                 220
Arg Gln Ala Thr Lys Asp Ala Gly Gln Ile Ala Gly Leu Asn Val Leu
225                 230                 235                 240
Arg Ile Val Asn Glu Pro Thr Ala Ala Leu Ala Tyr Gly Leu Asp
                245                 250                 255
Lys Gly Glu Lys Glu Gln Arg Ile Leu Val Phe Asp Leu Gly Gly Gly
            260                 265                 270
Thr Phe Asp Val Ser Leu Leu Glu Ile Gly Glu Gly Val Val Glu Val
        275                 280                 285
Arg Ala Thr Ser Gly Asp Asn His Leu Gly Gly Asp Asp Trp Asp Gln
    290                 295                 300
Arg Val Val Asp Trp Leu Val Asp Lys Phe Lys Gly Thr Ser Gly Ile
305                 310                 315                 320
Asp Leu Thr Lys Asp Lys Met Ala Met Gln Arg Leu Arg Glu Ala Ala
                325                 330                 335
Glu Lys Ala Lys Ile Glu Leu Ser Ser Ser Gln Ser Thr Ser Ile Asn
            340                 345                 350
Leu Pro Tyr Ile Thr Val Asp Ala Asp Lys Asn Pro Leu Phe Leu Asp
        355                 360                 365
Glu Gln Leu Thr Arg Ala Glu Phe Gln Arg Ile Thr Gln Asp Leu Leu
    370                 375                 380
Asp Arg Thr Arg Lys Pro Phe Gln Ser Val Ile Ala Asp Thr Gly Ile
385                 390                 395                 400
Ser Val Ser Glu Ile Asp His Val Val Leu Val Gly Gly Ser Thr Arg
                405                 410                 415
Met Pro Ala Val Thr Asp Leu Val Lys Glu Leu Thr Gly Gly Lys Glu
            420                 425                 430
Pro Asn Lys Gly Val Asn Pro Asp Glu Val Val Ala Val Gly Ala Ala
        435                 440                 445
Leu Gln Ala Gly Val Leu Lys Gly Glu Val Lys Asp Val Leu Leu Leu
    450                 455                 460
Asp Val Thr Pro Leu Ser Leu Gly Ile Glu Thr Lys Gly Gly Val Met
465                 470                 475                 480
Thr Arg Leu Ile Glu Arg Asn Thr Thr Ile Pro Thr Lys Arg Ser Glu
                485                 490                 495
Thr Phe Thr Thr Ala Asp Asp Asn Gln Pro Ser Val Gln Ile Gln Val
            500                 505                 510
Tyr Gln Gly Glu Arg Glu Ile Ala Ala His Asn Lys Leu Leu Gly Ser
        515                 520                 525
Phe Glu Leu Thr Gly Ile Pro Pro Ala Pro Arg Gly Ile Pro Gln Ile
    530                 535                 540
Glu Val Thr Phe Asp Ile Asp Ala Asn Gly Ile Val His Val Thr Ala
545                 550                 555                 560
Lys Asp Lys Gly Thr Gly Lys Glu Asn Thr Ile Arg Ile Gln Glu Gly
                565                 570                 575
Ser Gly Leu Ser Lys Glu Asp Ile Asp Arg Met Ile Lys Asp Ala Glu
            580                 585                 590
```

Ala His Ala Glu Glu Asp Arg Lys Arg Glu Glu Ala Asp Val Arg
        595                 600                 605

Asn Gln Ala Glu Thr Leu Val Tyr Gln Thr Glu Lys Phe Val Lys Glu
    610                 615                 620

Gln Arg Glu Ala Glu Gly Gly Ser Lys Val Pro Glu Asp Thr Leu Asn
625                 630                 635                 640

Lys Val Asp Ala Ala Val Ala Glu Ala Lys Ala Leu Gly Gly Ser
                645                 650                 655

Asp Ile Ser Ala Ile Lys Ser Ala Met Glu Lys Leu Gly Gln Glu Ser
                660                 665                 670

Gln Ala Leu Gly Gln Ala Ile Tyr Glu Ala Gln Ala Ala Ser Gln
        675                 680                 685

Ala Thr Gly Ala Ala His Pro Gly Gly Glu Pro Gly Ala His Pro
    690                 695                 700

Gly Ser Ala Asp Asp Val Val Asp Ala Glu Val Val Asp Asp Gly Arg
705                 710                 715                 720

Glu Ala Lys

<210> SEQ ID NO 21
<211> LENGTH: 1263
<212> TYPE: DNA
<213> ORGANISM: Mouse/Pseudomonas

<400> SEQUENCE: 21

```
atgtggctgc agaatttact tttcctgggc attgtggtct acagcctctc agcacccacc      60
cgctcaccca tcactgtcac ccggccttgg aagcatgtag aggccatcaa agaagccctg     120
aacctcctgg atgacatgcc tgtcacattg aatgaagagg tagaagtcgt ctctaacgag     180
ttctccttca agaagctaac atgtgtgcag acccgcctga agatattcga gcagggtcta     240
cggggcaatt tcaccaaact caagggcgcc ttgaacatga cagccagcta ctaccagaca     300
tactgccccc caactccgga aacgactgt gaaacacaag ttaccaccta tgcggatttc     360
atagacagcc ttaaaaacctt tctgactgat atccccttg aatgcaaaaa accagtccaa     420
aagaattctc gcctgcactt tcccgagggc ggcagcctgg ccgcgctgac cgcgcaccag     480
gcttgccacc tgccgctgga gactttcacc cgtcatcgcc agccgcgcgg ctgggaacaa     540
ctggagcagt gcggctatcc ggtgcagcgg ctggtcgccc tctacctggc ggcgcggctg     600
tcgtggaacc aggtcgacca ggtgatccgc aacgccctgg ccagccccgg cagcggcggc     660
gacctgggcg aagcgatccg cgagcagccg gagcaggccc gtctggccct gaccctggcc     720
gccgccgaga gcgagcgctt cgtccggcag ggcaccggca acgacgaggc cggcgcggcc     780
aacgccgacg tggtgagcct gacctgcccg gtcgccgccg gtgaatgcgc gggcccggcg     840
gacagcggcg acgccctgct ggagcgcaac tatcccactg gcgcggagtt cctcggcgac     900
ggcggcgacg tcagcttcag cacccgcggc acgcagaact ggatcctcat gcatggagat     960
acacctacat tgcatgaata tgttagat ttgcaaccag agacaactga tctctactgt    1020
tatgagcaat taaatgacag ctcagaggag gaggatgaaa tagatggtcc agctggacaa    1080
gcagaaccgg acagagccca ttacaatatt gtaaccttt gttgcaagtg tgactctacg    1140
cttcggttgt gcgtacaaag cacacacgta gacattcgta cttggaaga cctgttaatg    1200
ggcacactag gaattgtgtg ccccatctgt tctcaggata agcttggctg ttttggcgga    1260
tga                                                                   1263
```

-continued

```
<210> SEQ ID NO 22
<211> LENGTH: 420
<212> TYPE: PRT
<213> ORGANISM: Mouse/Pseudomonas

<400> SEQUENCE: 22

Met Trp Leu Gln Asn Leu Leu Phe Leu Gly Ile Val Val Tyr Ser Leu
 1               5                  10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Glu Val Val Ser Asn Glu Phe Ser Phe Lys
50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Val Gln Lys Asn Ser Arg
130                 135                 140

Leu His Phe Pro Glu Gly Gly Ser Leu Ala Ala Leu Thr Ala His Gln
145                 150                 155                 160

Ala Cys His Leu Pro Leu Glu Thr Phe Thr Arg His Arg Gln Pro Arg
                165                 170                 175

Gly Trp Glu Gln Leu Glu Gln Cys Gly Tyr Pro Val Gln Arg Leu Val
            180                 185                 190

Ala Leu Tyr Leu Ala Ala Arg Leu Ser Trp Asn Gln Val Asp Gln Val
        195                 200                 205

Ile Arg Asn Ala Leu Ala Ser Pro Gly Ser Gly Gly Asp Leu Gly Glu
210                 215                 220

Ala Ile Arg Glu Gln Pro Glu Gln Ala Arg Leu Ala Leu Thr Leu Ala
225                 230                 235                 240

Ala Ala Glu Ser Glu Arg Phe Val Arg Gln Gly Thr Gly Asn Asp Glu
                245                 250                 255

Ala Gly Ala Ala Asn Ala Asp Val Val Ser Leu Thr Cys Pro Val Ala
            260                 265                 270

Ala Gly Glu Cys Ala Gly Pro Ala Asp Ser Gly Asp Ala Leu Leu Glu
        275                 280                 285

Arg Asn Tyr Pro Thr Gly Ala Glu Phe Leu Gly Asp Gly Gly Asp Val
290                 295                 300

Ser Phe Ser Thr Arg Gly Thr Gln Asn Trp Ile Leu Met His Gly Asp
305                 310                 315                 320

Thr Pro Thr Leu His Glu Tyr Met Leu Asp Leu Gln Pro Glu Thr Thr
                325                 330                 335

Asp Leu Tyr Cys Tyr Glu Gln Leu Asn Asp Ser Ser Glu Glu Glu Asp
            340                 345                 350

Glu Ile Asp Gly Pro Ala Gly Gln Ala Glu Pro Asp Arg Ala His Tyr
        355                 360                 365

Asn Ile Val Thr Phe Cys Cys Lys Cys Asp Ser Thr Leu Arg Leu Cys
370                 375                 380
```

Val Gln Ser Thr His Val Asp Ile Arg Thr Leu Glu Asp Leu Leu Met
385                 390                 395                 400

Gly Thr Leu Gly Ile Val Cys Pro Ile Cys Ser Gln Asp Lys Leu Gly
                405                 410                 415

Cys Phe Gly Gly
            420

<210> SEQ ID NO 23
<211> LENGTH: 1842
<212> TYPE: DNA
<213> ORGANISM: Pseudomonas

<400> SEQUENCE: 23

| | | | | | |
|---|---|---|---|---|---|
| gccgaggaag | ccttcgacct | ctggaacgaa | tgcgccaaag | cctgcgtgct | cgacctcaag | 60 |
| gacggcgtgc | gttccagccg | catgagcgtc | gacccggcca | tcgccgacac | caacggccag | 120 |
| ggcgtgctgc | actactccat | ggtcctggag | ggcggcaaca | acgcgctcaa | gctggccatc | 180 |
| gacaacgccc | tcagcatcac | cagcgacggc | ctgaccatcc | gcctcgaagg | cggcgtcgag | 240 |
| ccgaacaagc | cggtgcgcta | cagctacacg | cgccaggcgc | gcggcagttg | gtcgctgaac | 300 |
| tggctggtac | cgatcggcca | cgagaagccc | tcgaacatca | aggtgttcat | ccacgaactg | 360 |
| aacgccggca | accagctcag | ccacatgtcg | ccgatctaca | ccatcgagat | gggcgacgag | 420 |
| ttgctggcga | agctggcgcg | cgatgccacc | ttcttcgtca | gggcgcacga | gagcaacgag | 480 |
| atgcagccga | cgctcgccat | cagccatgcc | ggggtcagcg | tggtcatggc | ccagacccag | 540 |
| ccgcgccggg | aaaagcgctg | gagcgaatgg | gccagcggca | aggtgttgtg | cctgctcgac | 600 |
| ccgctggacg | gggtctacaa | ctacctcgcc | cagcaacgct | gcaacctcga | cgatacctgg | 660 |
| gaaggcaaga | tctaccgggt | gctcgccggc | aacccggcga | agcatgacct | ggacatcaaa | 720 |
| cccacggtca | tcagtcatcg | cctgcacttt | cccgagggcg | gcagcctggc | cgcgctgacc | 780 |
| gcgcaccagg | cttgccacct | gccgctggag | actttcaccc | gtcatcgcca | gccgcgcggc | 840 |
| tgggaacaac | tggagcagtg | cggctatccg | gtgcagcggc | tggtcgccct | ctacctggcg | 900 |
| gcgcggctgt | cgtggaacca | ggtcgaccag | gtgatccgca | acgccctggc | cagccccggc | 960 |
| agcggcggcg | acctgggcga | agcgatccgc | gagcagccgg | agcaggcccg | tctggccctg | 1020 |
| accctggccg | ccgccgagag | cgagcgcttc | gtccggcagg | gcaccggcaa | cgacgaggcc | 1080 |
| ggcgcggcca | acgccgacgt | ggtgagcctg | acctgcccgg | tcgccgccgg | tgaatgcgcg | 1140 |
| ggcccggcgg | acagcggcga | cgccctgctg | gagcgcaact | atcccactgg | cgcggagttc | 1200 |
| ctcggcgacg | gcggcgacgt | cagcttcagc | acccgcggca | cgcagaactg | gacggtggag | 1260 |
| cggctgctcc | aggcgcaccg | ccaactggag | gagcgcggct | atgtgttcgt | cggctaccac | 1320 |
| ggcaccttcc | tcgaagcggc | gcaaagcatc | gtcttcggcg | gggtgcgcgc | gcgcagccag | 1380 |
| gacctcgacg | cgatctggcg | cggtttctat | atcgccggcg | atccgcgcgct | ggcctacggc | 1440 |
| tacgcccagg | accaggaacc | cgacgcacgc | ggccggatcc | gcaacggtgc | cctgctgcgg | 1500 |
| gtctatgtgc | cgcgctcgag | cctgccgggc | ttctaccgca | ccagcctgac | cctggccgcg | 1560 |
| ccggaggcgg | cgggcgaggt | cgaacggctg | atcgccatc | cgctgccgct | cgcctggac | 1620 |
| gccatcaccg | gccccgagga | ggaaggcggg | cgcctggaga | ccattctcgg | ctggccgctg | 1680 |
| gccgagcgca | ccgtggtgat | ccctcggcg | atccccaccg | acccgcgcaa | cgtcggcggc | 1740 |
| gacctcgacc | cgtccagcat | ccccgacaag | gaacaggcga | tcagcgccct | gccggactac | 1800 |
| gccagccagc | ccggcaaacc | gccgcgcgag | gacctgaagt | aa | | 1842 |

```
<210> SEQ ID NO 24
<211> LENGTH: 613
<212> TYPE: PRT
<213> ORGANISM: Pseudomonas

<400> SEQUENCE: 24
```

| | | | | | | | | | | | | | | |
|---|---|---|---|---|---|---|---|---|---|---|---|---|---|---|
| Ala | Glu | Glu | Ala | Phe | Asp | Leu | Trp | Asn | Glu | Cys | Ala | Lys | Ala | Cys | Val |
| 1 | | | | 5 | | | | | 10 | | | | | 15 | |
| Leu | Asp | Leu | Lys | Asp | Gly | Val | Arg | Ser | Ser | Arg | Met | Ser | Val | Asp | Pro |
| | | | 20 | | | | | 25 | | | | | 30 | | |
| Ala | Ile | Ala | Asp | Thr | Asn | Gly | Gln | Gly | Val | Leu | His | Tyr | Ser | Met | Val |
| | | 35 | | | | | 40 | | | | | 45 | | | |
| Leu | Glu | Gly | Gly | Asn | Asp | Ala | Leu | Lys | Leu | Ala | Ile | Asp | Asn | Ala | Leu |
| | 50 | | | | | 55 | | | | | 60 | | | | |
| Ser | Ile | Thr | Ser | Asp | Gly | Leu | Thr | Ile | Arg | Leu | Glu | Gly | Gly | Val | Glu |
| 65 | | | | | 70 | | | | | 75 | | | | | 80 |
| Pro | Asn | Lys | Pro | Val | Arg | Tyr | Ser | Tyr | Thr | Arg | Gln | Ala | Arg | Gly | Ser |
| | | | | 85 | | | | | 90 | | | | | 95 | |
| Trp | Ser | Leu | Asn | Trp | Leu | Val | Pro | Ile | Gly | His | Glu | Lys | Pro | Ser | Asn |
| | | | 100 | | | | | 105 | | | | | 110 | | |
| Ile | Lys | Val | Phe | Ile | His | Glu | Leu | Asn | Ala | Gly | Asn | Gln | Leu | Ser | His |
| | | 115 | | | | | 120 | | | | | 125 | | | |
| Met | Ser | Pro | Ile | Tyr | Thr | Ile | Glu | Met | Gly | Asp | Glu | Leu | Leu | Ala | Lys |
| | 130 | | | | | 135 | | | | | 140 | | | | |
| Leu | Ala | Arg | Asp | Ala | Thr | Phe | Phe | Val | Arg | Ala | His | Glu | Ser | Asn | Glu |
| 145 | | | | | 150 | | | | | 155 | | | | | 160 |
| Met | Gln | Pro | Thr | Leu | Ala | Ile | Ser | His | Ala | Gly | Val | Ser | Val | Val | Met |
| | | | | 165 | | | | | 170 | | | | | 175 | |
| Ala | Gln | Thr | Gln | Pro | Arg | Arg | Glu | Lys | Arg | Trp | Ser | Glu | Trp | Ala | Ser |
| | | | 180 | | | | | 185 | | | | | 190 | | |
| Gly | Lys | Val | Leu | Cys | Leu | Leu | Asp | Pro | Leu | Asp | Gly | Val | Tyr | Asn | Tyr |
| | | 195 | | | | | 200 | | | | | 205 | | | |
| Leu | Ala | Gln | Gln | Arg | Cys | Asn | Leu | Asp | Asp | Thr | Trp | Glu | Gly | Lys | Ile |
| | 210 | | | | | 215 | | | | | 220 | | | | |
| Tyr | Arg | Val | Leu | Ala | Gly | Asn | Pro | Ala | Lys | His | Asp | Leu | Asp | Ile | Lys |
| 225 | | | | | 230 | | | | | 235 | | | | | 240 |
| Pro | Thr | Val | Ile | Ser | His | Arg | Leu | His | Phe | Pro | Glu | Gly | Gly | Ser | Leu |
| | | | | 245 | | | | | 250 | | | | | 255 | |
| Ala | Ala | Leu | Thr | Ala | His | Gln | Ala | Cys | His | Leu | Pro | Leu | Glu | Thr | Phe |
| | | | 260 | | | | | 265 | | | | | 270 | | |
| Thr | Arg | His | Arg | Gln | Pro | Arg | Gly | Trp | Glu | Gln | Leu | Glu | Gln | Cys | Gly |
| | | 275 | | | | | 280 | | | | | 285 | | | |
| Tyr | Pro | Val | Gln | Arg | Leu | Val | Ala | Leu | Tyr | Leu | Ala | Ala | Arg | Leu | Ser |
| | 290 | | | | | 295 | | | | | 300 | | | | |
| Trp | Asn | Gln | Val | Asp | Gln | Val | Ile | Arg | Asn | Ala | Leu | Ala | Ser | Pro | Gly |
| 305 | | | | | 310 | | | | | 315 | | | | | 320 |
| Ser | Gly | Gly | Asp | Leu | Gly | Glu | Ala | Ile | Arg | Glu | Gln | Pro | Glu | Gln | Ala |
| | | | | 325 | | | | | 330 | | | | | 335 | |
| Arg | Leu | Ala | Leu | Thr | Leu | Ala | Ala | Ala | Glu | Ser | Glu | Arg | Phe | Val | Arg |
| | | | 340 | | | | | 345 | | | | | 350 | | |
| Gln | Gly | Thr | Gly | Asn | Asp | Glu | Ala | Gly | Ala | Ala | Asn | Ala | Asp | Val | Val |
| | | 355 | | | | | 360 | | | | | 365 | | | |
| Ser | Leu | Thr | Cys | Pro | Val | Ala | Ala | Gly | Glu | Cys | Ala | Gly | Pro | Ala | Asp |
| | 370 | | | | | 375 | | | | | 380 | | | | |

-continued

```
Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
            405                 410                 415

Trp Thr Val Glu Arg Leu Leu Gln Ala His Arg Gln Leu Glu Glu Arg
                420                 425                 430

Gly Tyr Val Phe Val Gly Tyr His Gly Thr Phe Leu Glu Ala Ala Gln
            435                 440                 445

Ser Ile Val Phe Gly Val Arg Ala Arg Ser Gln Asp Leu Asp Ala
450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
                515                 520                 525

Arg Leu Ile Gly His Pro Leu Pro Leu Arg Leu Asp Ala Ile Thr Gly
530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
                595                 600                 605

Arg Glu Asp Leu Lys
        610

<210> SEQ ID NO 25
<211> LENGTH: 287
<212> TYPE: PRT
<213> ORGANISM: Human papillomavirus/Mouse

<400> SEQUENCE: 25

Met Thr Val Leu Ala Pro Ala Trp Ser Pro Asn Ser Ser Leu Leu Leu
1               5                   10                  15

Leu Leu Leu Leu Ser Pro Cys Leu Arg Gly Thr Pro Asp Cys Tyr
            20                  25                  30

Phe Ser His Ser Pro Ile Ser Ser Asn Phe Lys Val Lys Phe Arg Glu
        35                  40                  45

Leu Thr Asp His Leu Leu Lys Asp Tyr Pro Val Thr Val Ala Val Asn
    50                  55                  60

Leu Gln Asp Glu Lys His Cys Lys Ala Leu Trp Ser Leu Phe Leu Ala
65                  70                  75                  80

Gln Arg Trp Ile Glu Gln Leu Lys Thr Val Ala Gly Ser Lys Met Gln
                85                  90                  95

Thr Leu Leu Glu Asp Val Asn Thr Glu Ile His Phe Val Thr Ser Cys
            100                 105                 110

Thr Phe Gln Pro Leu Pro Glu Cys Leu Arg Phe Val Gln Thr Asn Ile
        115                 120                 125

Ser His Leu Leu Lys Asp Thr Cys Thr Gln Leu Leu Ala Leu Lys Pro
    130                 135                 140
```

-continued

```
Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Pro Arg Ser Pro Ile Ala
                165                 170                 175

Leu Glu Ala Thr Glu Leu Pro Glu Pro Arg Pro Arg Gln Met His Gly
            180                 185                 190

Asp Thr Pro Thr Leu His Glu Tyr Met Leu Asp Leu Gln Pro Glu Thr
        195                 200                 205

Thr Asp Leu Tyr Cys Tyr Glu Gln Leu Asn Asp Ser Ser Glu Glu Glu
    210                 215                 220

Asp Glu Ile Asp Gly Pro Ala Gly Gln Ala Glu Pro Asp Arg Ala His
225                 230                 235                 240

Tyr Asn Ile Val Thr Phe Cys Cys Lys Cys Asp Ser Thr Leu Arg Leu
                245                 250                 255

Cys Val Gln Ser Thr His Val Asp Ile Arg Thr Leu Glu Asp Leu Leu
                260                 265                 270

Met Gly Thr Leu Gly Ile Val Cys Pro Ile Cys Ser Gln Lys Pro
            275                 280                 285
```